(12) United States Patent
McAllister et al.

(10) Patent No.: US 11,596,517 B2
(45) Date of Patent: Mar. 7, 2023

(54) MODIFIED DEMINERALIZED CORTICAL BONE FIBERS

(71) Applicant: Musculoskeletal Transplant Foundation, Edison, NJ (US)

(72) Inventors: Michele McAllister, Freehold, NJ (US); David Wang, Rockville, MD (US); Michelle Bubear, Newton, NJ (US); Joed Canales, Harrison, NJ (US); Amy Chang, Kaneohe, HI (US); Roman Shikhanovich, Edison, NJ (US); Mark Spilker, Plainsboro, NJ (US); Eric Semler, Morganville, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 638 days.

(21) Appl. No.: 16/598,354

(22) Filed: Oct. 10, 2019

(65) Prior Publication Data
US 2020/0046501 A1 Feb. 13, 2020

Related U.S. Application Data

(62) Division of application No. 15/159,406, filed on May 19, 2016, now Pat. No. 10,531,957.
(Continued)

(51) Int. Cl.
*A61F 2/28* (2006.01)
*A61L 27/36* (2006.01)

(52) U.S. Cl.
CPC ............ *A61F 2/28* (2013.01); *A61L 27/3604* (2013.01); *A61L 27/365* (2013.01); *A61L 27/3608* (2013.01); *A61L 27/3683* (2013.01); *A61F 2240/001* (2013.01); *A61L 2400/18* (2013.01); *A61L 2430/02* (2013.01); *A61L 2430/38* (2013.01)

(58) Field of Classification Search
CPC combination set(s) only.
See application file for complete search history.

(56) References Cited

U.S. PATENT DOCUMENTS

| | | | |
|---|---|---|---|
| 753,155 | A | 2/1904 | MacFarlane |
| 2,446,573 | A | 8/1948 | Cameron |

(Continued)

FOREIGN PATENT DOCUMENTS

| | | |
|---|---|---|
| CA | 2177017 | 6/1995 |
| CA | 250737 | 6/2004 |

(Continued)

OTHER PUBLICATIONS

Office Action dated Feb. 1, 2021 for corresponding Canadian Patent Application No. 2986702.
(Continued)

*Primary Examiner* — Ernst V Arnold
(74) *Attorney, Agent, or Firm* — Marcella M. Bodner; Cole Schotz, P.C.

(57) ABSTRACT

Methods for making surgical implants (or grafts) for the repair of bone defects, and more particularly, surgical implants that include demineralized bone fibers, are disclosed. Also disclosed are methods for increasing the wettability and ensuring uniform density of such implants. The surgical implants have a wettability time of less than 5 minutes and a residual moisture content of less than 6% by weight, and they remain cohesive and retain their shape upon complete rehydration.

16 Claims, 5 Drawing Sheets

Related U.S. Application Data

(60) Provisional application No. 62/331,071, filed on May 3, 2016, provisional application No. 62/164,827, filed on May 21, 2015.

(56) References Cited

U.S. PATENT DOCUMENTS

| | | |
|---|---|---|
| 3,856,219 A | 12/1974 | Stayton et al. |
| 4,294,753 A | 10/1981 | Urist |
| 4,361,552 A | 11/1982 | Baur |
| 4,394,370 A | 7/1983 | Jefferies |
| 4,627,853 A | 12/1986 | Campbell |
| 4,820,626 A | 4/1989 | Williams et al. |
| 5,002,071 A | 3/1991 | Harrell |
| 5,035,708 A | 7/1991 | Alchas |
| 5,061,286 A | 10/1991 | Lyle |
| 5,073,373 A | 12/1991 | O'Leary |
| 5,079,160 A | 1/1992 | Lacy |
| 5,112,354 A | 5/1992 | Sires |
| 5,131,907 A | 7/1992 | Williams |
| 5,204,319 A | 4/1993 | Enomoto |
| 5,219,576 A | 6/1993 | Chu |
| 5,230,693 A | 7/1993 | Williams |
| 5,236,456 A | 8/1993 | O'Leary |
| 5,275,954 A | 1/1994 | Wolfinbarger et al. |
| 5,284,655 A | 2/1994 | Bogdansky et al. |
| 5,290,558 A | 3/1994 | O'Leary |
| 5,298,254 A | 3/1994 | Prewell |
| 5,314,476 A | 5/1994 | Prewett et al. |
| 5,333,626 A | 8/1994 | Morse |
| 5,356,629 A | 10/1994 | Sander et al. |
| 5,405,390 A | 4/1995 | O'Leary et al. |
| 5,439,684 A | 8/1995 | Prewell |
| 5,484,601 A | 1/1996 | O'Leary et al. |
| 5,486,359 A | 1/1996 | Caplan |
| 5,507,813 A | 4/1996 | Dowd |
| 5,510,396 A | 4/1996 | Prewett et al. |
| 5,513,662 A | 5/1996 | Morse |
| 5,556,379 A | 9/1996 | Wolfinbarger |
| 5,573,771 A | 11/1996 | Geistlich et al. |
| 5,607,269 A | 3/1997 | Dowd et al. |
| 5,612,028 A | 3/1997 | Sackler |
| 5,628,781 A | 5/1997 | Williams |
| 5,676,146 A | 10/1997 | Scarborough |
| 5,700,289 A | 12/1997 | Breibart |
| 5,702,677 A | 12/1997 | Shimp et al. |
| 5,707,962 A | 1/1998 | Chen et al. |
| 5,744,360 A | 4/1998 | Hu |
| 5,797,871 A | 8/1998 | Wolfinbarger |
| 5,804,366 A | 9/1998 | Hu |
| 5,807,275 A | 9/1998 | Jamshidi |
| 5,824,078 A | 10/1998 | Nelson |
| 5,824,084 A | 10/1998 | Muschler |
| 5,830,493 A | 11/1998 | Yokota et al. |
| 5,837,235 A | 11/1998 | Mueller |
| 5,842,477 A | 12/1998 | Naughton |
| 5,869,037 A | 2/1999 | Crystal |
| 5,895,426 A | 4/1999 | Scarborough et al. |
| 5,899,939 A | 5/1999 | Boyce |
| 5,904,718 A | 5/1999 | Jeffries |
| 5,918,821 A | 7/1999 | Grooms et al. |
| 5,968,556 A | 10/1999 | Atala et al. |
| 5,980,948 A | 11/1999 | Goedemoed et al. |
| 6,020,196 A | 2/2000 | Hu |
| 6,030,635 A | 2/2000 | Gertzman et al. |
| 6,045,580 A | 4/2000 | Scarborough et al. |
| 6,049,026 A | 4/2000 | Muschler |
| 6,051,750 A | 4/2000 | Bell |
| 6,077,987 A | 6/2000 | Breitbart |
| 6,123,731 A | 9/2000 | Boyce |
| 6,149,906 A | 11/2000 | Mosca |
| 6,152,142 A | 11/2000 | Tseng |
| 6,162,258 A | 12/2000 | Scarborough et al. |
| 6,180,605 B1 | 1/2001 | Chen et al. |
| 6,180,606 B1 | 1/2001 | Chen et al. |
| 6,187,053 B1 | 2/2001 | Minuth |
| 6,189,537 B1 | 2/2001 | Wolfinbarger |
| 6,326,019 B1 | 2/2001 | Tseng |
| 6,284,284 B1 | 9/2001 | Naughton |
| 6,293,970 B1 | 9/2001 | Wolfinbarger et al. |
| 6,294,041 B1 | 9/2001 | Boyce et al. |
| 6,294,187 B1 | 9/2001 | Boyce |
| 6,305,379 B1 | 10/2001 | Wolfinbarger |
| 6,309,659 B1 | 10/2001 | Clokie |
| 6,311,690 B1 | 11/2001 | Jefferies |
| 6,312,952 B1 | 11/2001 | Hicks |
| 6,315,795 B1 | 11/2001 | Scarborough et al. |
| 6,316,247 B1 | 11/2001 | Katz |
| 6,326,018 B1 | 12/2001 | Gertzman |
| 6,332,779 B1 | 12/2001 | Boyce |
| 6,340,477 B1 | 1/2002 | Anderson |
| 6,348,069 B1 | 2/2002 | Vacanti |
| 6,350,283 B1 | 2/2002 | Michelson |
| 6,355,239 B1 | 3/2002 | Bruder |
| 6,372,257 B1 | 4/2002 | Marchosky |
| 6,375,663 B1 | 4/2002 | Ebner |
| 6,376,244 B1 | 4/2002 | Atala |
| 6,379,371 B1 | 4/2002 | Novak |
| 6,387,693 B2 | 5/2002 | Reiser |
| 6,391,297 B1 | 5/2002 | Halvorsen |
| 6,398,819 B1 | 6/2002 | Bell |
| 6,413,278 B1 | 7/2002 | Marchosky |
| 6,425,949 B1 | 7/2002 | Lemaire et al. |
| 6,429,013 B1 | 8/2002 | Halvorsen |
| 6,432,436 B1 | 8/2002 | Gertzman et al. |
| 6,436,138 B1 | 8/2002 | Dowd |
| 6,437,018 B1 | 8/2002 | Gertzman et al. |
| 6,440,444 B2 | 8/2002 | Boyce |
| 6,458,375 B1 | 10/2002 | Gertzman |
| 6,461,632 B1 | 10/2002 | Gogolewski |
| 6,465,205 B2 | 10/2002 | Hicks, Jr. |
| 6,478,825 B1 | 11/2002 | Winterbottom |
| 6,484,954 B2 | 11/2002 | Lenox |
| 6,534,095 B1 | 3/2003 | Moore-Smith |
| 6,548,080 B1 | 4/2003 | Gertzman et al. |
| 6,565,884 B2 | 5/2003 | Nimmi |
| 6,569,200 B2 | 5/2003 | Wolfinbarger et al. |
| 6,576,015 B2 | 6/2003 | Geistlich et al. |
| 6,576,249 B1 | 6/2003 | Gendler |
| 6,596,274 B1 | 7/2003 | Abatangelo |
| 6,599,520 B2 | 7/2003 | Scarborough |
| 6,616,698 B2 | 9/2003 | Scarborough |
| 6,620,196 B1 | 9/2003 | Trieu |
| 6,623,748 B2 | 9/2003 | Clokie |
| 6,630,153 B2 | 10/2003 | Long et al. |
| 6,625,593 B1 | 11/2003 | Boyer |
| 6,652,592 B1 | 11/2003 | Grooms et al. |
| 6,652,872 B2 | 11/2003 | Nevo |
| 6,652,887 B1 | 11/2003 | Richelsophe et al. |
| 6,660,038 B2 | 12/2003 | Boyer |
| 6,685,626 B2 | 2/2004 | Wironen |
| 6,696,073 B2 | 2/2004 | Boyce |
| 6,706,067 B2 | 3/2004 | Shimp |
| 6,723,131 B2 | 4/2004 | Muschler |
| RE38,522 E | 5/2004 | Gertman et al. |
| 6,749,636 B2 | 6/2004 | Michelson |
| 6,752,831 B2 | 6/2004 | Sybert |
| 6,755,365 B1 | 6/2004 | Meredith et al. |
| 6,776,800 B2 | 8/2004 | Boyer |
| 6,777,231 B1 | 8/2004 | Katz |
| 6,808,585 B2 | 10/2004 | Boyce |
| 6,830,763 B2 | 12/2004 | O'Leary et al. |
| 6,837,907 B2 | 1/2005 | Wolfinbarger et al. |
| 6,841,150 B2 | 1/2005 | Halvorsen |
| 6,843,807 B1 | 1/2005 | Boyce et al. |
| 6,846,853 B2 | 1/2005 | Shimp |
| 6,855,169 B2 | 2/2005 | Boyer, II et al. |
| 6,863,694 B1 | 3/2005 | Boyce |
| 6,893,466 B2 | 5/2005 | Trieu |
| 6,899,107 B2 | 5/2005 | Lewandrowski |
| 6,911,212 B2 | 6/2005 | Gertzman et al. |
| 6,974,862 B2 | 12/2005 | Ringeisen et al. |
| 6,979,307 B2 | 12/2005 | Beretta |
| 6,979,679 B2 | 12/2005 | Marcum |

(56) References Cited

U.S. PATENT DOCUMENTS

| | | |
|---|---|---|
| 6,991,652 B2 | 1/2006 | Burg |
| 6,998,135 B1 | 2/2006 | Sunwoo et al. |
| 7,004,977 B2 | 2/2006 | Ashman |
| 7,005,136 B2 | 2/2006 | Nathan et al. |
| 7,008,591 B2 | 3/2006 | Kafesjian |
| 7,008,763 B2 | 3/2006 | Cheung |
| 7,019,192 B2 | 3/2006 | Gertzman et al. |
| 7,029,666 B2 | 4/2006 | Bruder |
| 7,029,689 B2 | 4/2006 | Berglund |
| 7,029,838 B2 | 4/2006 | Williams |
| 7,033,587 B2 | 4/2006 | Halvorsen |
| 7,045,141 B2 | 5/2006 | Merboth et al. |
| 7,052,829 B2 | 5/2006 | Williams |
| 7,052,907 B2 | 5/2006 | Shi |
| 7,063,726 B2 | 6/2006 | Crouch et al. |
| 7,067,123 B2 | 6/2006 | Gomes et al. |
| 7,078,230 B2 | 7/2006 | Wilkison |
| 7,078,232 B2 | 7/2006 | Konkle |
| 7,148,036 B2 | 12/2006 | Luyten |
| 7,153,518 B2 | 12/2006 | Wironen et al. |
| 7,163,691 B2 | 1/2007 | Knaack |
| 7,166,133 B2 | 1/2007 | Evans |
| 7,172,629 B2 | 2/2007 | McKay |
| 7,179,299 B2 | 2/2007 | Edwards |
| 7,186,557 B2 | 3/2007 | Marko |
| 7,189,392 B1 | 3/2007 | Kim et al. |
| RE39,587 E | 4/2007 | Gertzman et al. |
| 7,201,917 B2 | 4/2007 | Malaviya |
| 7,214,765 B2 | 5/2007 | Ringeisen et al. |
| 7,241,316 B2 | 7/2007 | Evans |
| 7,244,444 B2 | 7/2007 | Bales |
| 7,250,550 B2 | 7/2007 | Overby et al. |
| 7,255,879 B2 | 8/2007 | Hariri |
| 7,270,813 B2 | 9/2007 | Shimp et al. |
| 7,273,756 B2 | 9/2007 | Adkisson |
| 7,291,179 B2 | 11/2007 | Miller et al. |
| 7,291,345 B2 | 11/2007 | Winterbottom et al. |
| 7,294,509 B2 | 11/2007 | Darimont |
| 7,297,540 B2 | 11/2007 | Miltrani |
| 7,311,904 B2 | 12/2007 | Haran |
| 7,311,905 B2 | 12/2007 | Hariri |
| 7,323,190 B2 | 1/2008 | Chu |
| 7,323,193 B2 | 1/2008 | Morris |
| 7,326,571 B2 | 2/2008 | Freyman |
| 7,335,381 B2 | 2/2008 | Malinin |
| 7,347,876 B2 | 3/2008 | Tsai |
| 7,390,484 B2 | 6/2008 | Fraser |
| 7,413,576 B2 | 8/2008 | Sybert |
| 7,413,734 B2 | 8/2008 | Mistry |
| 7,416,889 B2 | 8/2008 | Ciombor |
| 7,429,488 B2 | 9/2008 | Fraser |
| 7,445,793 B2 | 11/2008 | Niwa |
| 7,459,307 B2 | 12/2008 | Ha |
| 7,468,242 B2 | 12/2008 | Bellomo |
| 7,468,276 B2 | 12/2008 | Harin |
| 7,470,537 B2 | 12/2008 | Hedrick |
| 7,473,420 B2 | 1/2009 | Fraser |
| 7,473,678 B2 | 1/2009 | Lynch |
| 7,476,257 B2 | 1/2009 | Sah |
| 7,485,629 B2 | 2/2009 | Marcum |
| 7,488,348 B2 | 2/2009 | Truncale |
| 7,494,802 B2 | 2/2009 | Tseng |
| 7,494,811 B2 | 2/2009 | Wolfinbarger et al. |
| 7,494,950 B2 | 2/2009 | Armiage et al. |
| 7,498,040 B2 | 3/2009 | Masinaei |
| 7,498,041 B2 | 3/2009 | Masinaei |
| 7,498,171 B2 | 3/2009 | Hariri et al. |
| 7,501,115 B2 | 3/2009 | Fraser |
| 7,503,936 B2 | 3/2009 | Trieu |
| 7,504,387 B2 | 3/2009 | Marcum |
| 7,514,075 B2 | 4/2009 | Hedrick |
| 7,524,489 B2 | 4/2009 | Messina |
| 7,531,355 B2 | 5/2009 | Rodriquez et al. |
| 7,537,617 B2 | 5/2009 | Bindsell |
| 7,560,276 B2 | 7/2009 | Harmon |
| 7,563,455 B2 | 7/2009 | McKay |
| 7,575,743 B2 | 8/2009 | Hunziker |
| 7,582,292 B2 | 9/2009 | Wilkison et al. |
| 7,582,309 B2 | 9/2009 | Rosenberg et al. |
| 7,585,670 B2 | 9/2009 | Hedrick |
| 7,592,174 B2 | 9/2009 | Sylvester |
| 7,595,043 B2 | 9/2009 | Hedrick |
| 7,595,062 B2 | 9/2009 | Pedrozo |
| 7,608,113 B2 | 10/2009 | Boyer |
| 7,608,580 B2 | 10/2009 | Kim et al. |
| 7,618,461 B2 | 11/2009 | Trieu |
| 7,621,963 B2 | 11/2009 | Simon |
| 7,628,851 B2 | 12/2009 | Armitage et al. |
| 7,637,872 B1 | 12/2009 | Fox |
| 7,651,684 B2 | 1/2010 | Hedrick |
| 2,042,010 A1 | 2/2010 | Clarke |
| 7,655,010 B2 | 2/2010 | Serhan et al. |
| 7,658,768 B2 | 2/2010 | Miller et al. |
| 7,662,184 B2 | 2/2010 | Edwards |
| 7,670,384 B2 | 3/2010 | Kumar |
| 7,675,272 B2 | 3/2010 | Michallick et al. |
| 7,678,385 B2 | 3/2010 | Reddi |
| 7,682,803 B2 | 3/2010 | Paludan |
| 7,687,059 B2 | 3/2010 | Fraser |
| 7,709,018 B2 | 5/2010 | Pastorello |
| 7,726,319 B1 | 6/2010 | Boyce |
| 7,732,126 B2 | 6/2010 | Zhang |
| 7,744,597 B2 | 6/2010 | Gaskins |
| 7,745,106 B2 | 6/2010 | Beretta |
| 7,753,963 B2 | 7/2010 | Boyce |
| 7,766,972 B2 | 8/2010 | Overby et al. |
| 7,767,452 B2 | 8/2010 | Kleinsek |
| 7,771,716 B2 | 8/2010 | Hedrick |
| 7,772,209 B2 | 8/2010 | Niyikiza |
| 7,775,965 B2 | 8/2010 | McFedrige |
| 7,776,596 B2 | 8/2010 | Badylak |
| 7,785,582 B2 | 8/2010 | Johnson |
| 7,785,634 B2 | 8/2010 | Borden |
| 7,795,022 B2 | 9/2010 | Badylak |
| 7,795,027 B2 | 9/2010 | Miles |
| 7,799,076 B2 | 9/2010 | Sybert |
| 7,799,767 B2 | 9/2010 | Lamberti et al. |
| 7,807,461 B2 | 10/2010 | Kang |
| 7,815,686 B2 | 10/2010 | Badylak |
| 7,824,671 B2 | 11/2010 | Binder |
| 7,824,702 B2 | 11/2010 | Wironen et al. |
| 7,824,703 B2 | 11/2010 | Scifert et al. |
| 7,833,278 B2 | 11/2010 | Evans |
| 7,833,968 B2 | 11/2010 | Soo et al. |
| 7,837,708 B2 | 11/2010 | Schmieding |
| 7,842,300 B2 | 11/2010 | Atkinson et al. |
| 7,846,728 B2 | 12/2010 | Brooks |
| 7,854,923 B2 | 12/2010 | Chen et al. |
| 7,858,296 B2 | 12/2010 | Sowmino-Coker |
| 7,871,646 B2 | 1/2011 | Ghinelli |
| 7,875,272 B2 | 1/2011 | Messina |
| 7,875,273 B2 | 1/2011 | Messina |
| 7,875,296 B2 | 1/2011 | Binette |
| 7,887,795 B2 | 2/2011 | Fraser |
| 7,888,119 B2 | 2/2011 | Sugaya |
| 7,892,577 B2 | 2/2011 | Borden |
| RE42,208 E | 3/2011 | Truncale et al. |
| 7,901,457 B2 | 3/2011 | Truncale et al. |
| 7,901,461 B2 | 3/2011 | Harmon |
| 7,901,672 B2 | 3/2011 | Fraser |
| 7,906,110 B2 | 3/2011 | Chancellor |
| 7,910,690 B2 | 3/2011 | Ringeisen et al. |
| 7,914,779 B2 | 3/2011 | Hariri |
| 7,915,039 B2 | 3/2011 | Teplyashin |
| 7,923,246 B2 | 4/2011 | Sasai |
| 7,931,687 B2 | 4/2011 | Masuda |
| 7,931,692 B2 | 4/2011 | Sybert et al. |
| 7,932,084 B2 | 4/2011 | Katz |
| 7,939,092 B2 | 5/2011 | McKay et al. |
| 7,939,108 B2 | 5/2011 | Morris |
| 7,947,266 B2 | 5/2011 | Grothos |
| 7,951,200 B2 | 5/2011 | Heinz |
| 7,955,616 B2 | 6/2011 | Kroenentha |
| 7,959,683 B2 | 6/2011 | Semler et al. |

(56) References Cited

U.S. PATENT DOCUMENTS

| | | |
|---|---|---|
| 7,959,941 B2 | 6/2011 | Knaack |
| 7,968,329 B2 | 6/2011 | Dancu |
| 7,977,094 B2 | 7/2011 | Masinaei |
| 7,998,472 B2 | 8/2011 | Huss |
| 7,998,735 B2 | 8/2011 | Morrison |
| 8,002,813 B2 | 8/2011 | Scarborough |
| 8,002,843 B2 | 8/2011 | Knacck |
| 8,039,016 B2 | 10/2011 | Drapeau |
| 8,053,423 B2 | 11/2011 | Lamberti et al. |
| 8,057,595 B2 | 11/2011 | Armitage et al. |
| 8,101,676 B2 | 1/2012 | McKay |
| 8,105,383 B2 | 1/2012 | Michelson |
| 8,106,008 B2 | 1/2012 | Lynch |
| RE43,258 E | 3/2012 | Truncale et al. |
| 8,133,421 B2 | 3/2012 | Boyce |
| 8,133,500 B2 | 3/2012 | Ringeisen |
| 8,137,403 B2 | 3/2012 | Michelson |
| 8,137,408 B2 | 3/2012 | Kadiyala |
| 8,137,686 B2 | 3/2012 | Kladakis |
| 8,147,862 B2 | 4/2012 | McKay |
| 8,153,612 B2 | 4/2012 | Ben-Shalom et al. |
| 8,182,532 B2 | 5/2012 | Anderson et al. |
| 8,183,229 B2 | 5/2012 | Hahn et al. |
| 8,188,229 B2 | 5/2012 | Ringeisen et al. |
| 8,197,474 B2 | 6/2012 | Scarborough |
| 8,202,539 B2 | 6/2012 | Benham |
| 8,221,500 B2 | 7/2012 | Truncale et al. |
| 8,221,781 B2 | 7/2012 | Rosenberg et al. |
| 8,268,008 B2 | 9/2012 | Betz |
| 8,282,953 B2 | 10/2012 | Drapeau |
| 8,292,957 B2 | 10/2012 | Michelson |
| 8,292,968 B2 | 10/2012 | Truncale |
| 8,309,106 B2 | 11/2012 | Masinaei |
| 8,309,131 B2 | 11/2012 | Kronenthal |
| 8,313,742 B2 | 11/2012 | Kadiyala et al. |
| 8,323,700 B2 | 12/2012 | Morris et al. |
| 8,328,876 B2 | 12/2012 | Behnam et al. |
| 8,333,985 B2 | 12/2012 | Knaack et al. |
| 8,357,384 B2 | 1/2013 | Behnam |
| 8,399,010 B2 | 3/2013 | McKay |
| 8,399,409 B2 | 3/2013 | Lynch et al. |
| 8,419,802 B2 | 4/2013 | Evans |
| 8,425,619 B2 | 4/2013 | Evans et al. |
| 8,454,988 B2 | 6/2013 | Rosenberg |
| 8,455,458 B2 | 6/2013 | Marcum |
| 8,460,680 B2 | 6/2013 | Williams |
| 8,470,369 B2 | 6/2013 | Marchosky |
| 8,475,824 B2 | 7/2013 | McKay |
| 8,496,970 B2 | 7/2013 | Binette |
| 8,513,217 B2 | 8/2013 | Chen et al. |
| 8,524,253 B2 | 9/2013 | Kinnane |
| 8,529,862 B2 | 9/2013 | Tennent |
| 8,529,962 B2 | 9/2013 | Morris et al. |
| 8,545,864 B2 | 10/2013 | Morris et al. |
| 8,551,170 B2 | 10/2013 | Lacza et al. |
| 8,563,040 B2 | 10/2013 | Marchosky |
| 8,574,825 B2 | 11/2013 | Shelby et al. |
| 8,603,184 B2 | 12/2013 | Rizzoli et al. |
| 8,623,094 B2 | 1/2014 | Evans |
| 8,633,299 B2 | 1/2014 | Ringeisen et al. |
| 8,642,061 B2 | 2/2014 | Shimp et al. |
| 8,652,503 B2 | 2/2014 | Wironen et al. |
| 8,658,197 B2 | 2/2014 | Scifert |
| 8,658,217 B2 | 2/2014 | McKay |
| 8,663,672 B2 | 3/2014 | Manrique |
| 8,664,202 B2 | 3/2014 | Lamberti et al. |
| 8,697,107 B2 | 4/2014 | Drapeau et al. |
| 8,697,114 B2 | 4/2014 | Scifert |
| 8,734,525 B2 | 5/2014 | Behnam |
| 8,734,835 B2 | 5/2014 | McKay et al. |
| 8,740,987 B2 | 6/2014 | Geremakis et al. |
| 8,747,467 B2 | 6/2014 | Mills et al. |
| 8,753,689 B2 | 6/2014 | Morris et al. |
| 8,758,792 B2 | 6/2014 | Behnam et al. |
| 8,790,920 B2 | 6/2014 | Freyman |
| 8,771,368 B2 | 7/2014 | McKay |
| 8,784,499 B2 | 7/2014 | Owens et al. |
| 8,790,681 B2 | 7/2014 | Altschuler |
| 8,834,928 B1 | 9/2014 | Truncale et al. |
| 8,871,742 B2 | 10/2014 | Marcum et al. |
| 8,876,532 B2 | 11/2014 | Atkinso et al. |
| 8,877,221 B2 | 11/2014 | McKay |
| 8,883,210 B1 | 11/2014 | Truncale et al. |
| 8,926,710 B2 | 1/2015 | McKay |
| 8,957,050 B2 | 2/2015 | Lamberti et al. |
| 8,992,628 B2 | 3/2015 | Drapeau et al. |
| 9,005,646 B2 | 4/2015 | Masinaei et al. |
| 9,034,348 B2 | 5/2015 | Shalom et al. |
| 9,034,644 B2 | 5/2015 | Masinei et al. |
| 9,050,390 B2 | 6/2015 | Rizzoli et al. |
| 9,056,151 B2 | 6/2015 | Lauritzen et al. |
| 9,080,141 B2 | 7/2015 | Wolfingarger et al. |
| 9,101,606 B2 | 8/2015 | Drapeau et al. |
| 9,107,983 B2 | 8/2015 | McKay |
| 9,132,208 B2 | 9/2015 | Chen et al. |
| 9,138,509 B2 | 9/2015 | Sunwoo et al. |
| 9,162,012 B2 | 10/2015 | Benham et al. |
| 9,211,359 B2 | 12/2015 | McKay et al. |
| 9,254,301 B2 | 2/2016 | Marchosky |
| 9,259,434 B2 | 2/2016 | Chen et al. |
| 9,265,830 B2 | 2/2016 | Mossaad et al. |
| 9,283,074 B2 | 3/2016 | Evans et al. |
| 9,289,452 B2 | 3/2016 | Shi |
| 9,314,545 B2 | 4/2016 | Tofighi et al. |
| 9,320,708 B2 | 4/2016 | Scifert |
| 9,333,276 B2 | 5/2016 | Guelcher et al. |
| 9,352,003 B1 | 5/2016 | Semler et al. |
| 9,364,583 B2 | 6/2016 | McKay |
| 9,375,315 B2 | 6/2016 | Forsell |
| 9,387,094 B2 | 6/2016 | Manrique et al. |
| 9,381,211 B2 | 7/2016 | Marcum et al. |
| 9,393,116 B2 | 7/2016 | Betz |
| 9,408,875 B2 | 8/2016 | Masinaei et al. |
| 9,415,139 B2 | 8/2016 | Benedict et al. |
| 9,480,567 B2 | 11/2016 | McKay |
| 9,486,500 B2 | 11/2016 | McKay |
| 9,486,556 B2 | 11/2016 | Shi |
| 9,486,557 B2 | 11/2016 | Carter et al. |
| 9,511,115 B2 | 12/2016 | Soo et al. |
| 9,554,920 B2 | 1/2017 | Wei et al. |
| 9,572,911 B2 | 2/2017 | Muir |
| 9,572,912 B2 | 2/2017 | Scarborough et al. |
| 9,579,416 B2 | 2/2017 | Ringeisen et al. |
| 9,579,421 B2 | 2/2017 | Bhat et al. |
| 9,623,146 B2 | 4/2017 | Lamberti et al. |
| 9,623,153 B2 | 4/2017 | McKay |
| 9,636,436 B2 | 5/2017 | Carter et al. |
| 9,682,172 B2 | 6/2017 | Drapeau et al. |
| 9,717,822 B2 | 8/2017 | Behnam et al. |
| 9,730,801 B2 | 8/2017 | McKay |
| 9,731,044 B2 | 8/2017 | Chen et al. |
| 9,775,862 B2 | 10/2017 | Wei et al. |
| 9,801,946 B2 | 10/2017 | Guelcher et al. |
| 9,839,722 B2 | 12/2017 | McKay |
| 9,849,215 B2 | 12/2017 | Mossaad et al. |
| 9,907,882 B2 | 3/2018 | McKay |
| 9,913,676 B2 | 3/2018 | Schlacter et al. |
| 9,956,313 B2 | 5/2018 | Tofighi et al. |
| 9,962,467 B2 | 5/2018 | Masinaei et al. |
| 9,981,061 B2 | 5/2018 | Evans et al. |
| 9,987,138 B2 | 6/2018 | McKay |
| 9,999,520 B2 | 6/2018 | Manrique et al. |
| 10,130,736 B1 | 11/2018 | Semler et al. |
| 10,194,964 B2 | 2/2019 | Schlachter et al. |
| 2001/0016703 A1 | 8/2001 | Wironen et al. |
| 2001/0033834 A1 | 10/2001 | Wilkison |
| 2001/0037091 A1 | 11/2001 | Wironen et al. |
| 2001/0041792 A1 | 11/2001 | Donda |
| 2002/0029045 A1 | 3/2002 | Bonutti |
| 2002/0076395 A1 | 6/2002 | Crystal |
| 2002/0076400 A1 | 6/2002 | Katz |
| 2002/0091447 A1 | 7/2002 | Shimp |
| 2002/0106393 A1 | 8/2002 | Bianchi et al. |
| 2002/0107429 A1 | 8/2002 | Wironen |

(56) References Cited

U.S. PATENT DOCUMENTS

| | | |
|---|---|---|
| 2002/0110544 A1 | 8/2002 | Goldberg |
| 2002/0122790 A1 | 9/2002 | Hunziker |
| 2002/0159982 A1 | 10/2002 | Bonassar |
| 2002/0192263 A1 | 12/2002 | Merboth et al. |
| 2003/0009235 A1 | 1/2003 | Manrique et al. |
| 2003/0054331 A1 | 3/2003 | Fraser |
| 2003/0055511 A1 | 3/2003 | Schryer et al. |
| 2003/0077825 A1 | 4/2003 | Bhatnagar |
| 2003/0082152 A1 | 5/2003 | Hedrick |
| 2003/0091543 A1 | 5/2003 | Klein |
| 2003/0113813 A1 | 6/2003 | Heidaran |
| 2003/0147860 A1 | 8/2003 | Marchosky |
| 2003/0148510 A1 | 8/2003 | Mitrani |
| 2003/0152558 A1 | 8/2003 | Luft |
| 2003/0161816 A1 | 8/2003 | Fraser |
| 2003/0162707 A1 | 8/2003 | Fraser |
| 2003/0180262 A1 | 9/2003 | Wiroenen et al. |
| 2003/0180269 A1 | 9/2003 | Hariri |
| 2003/0180344 A1 | 9/2003 | Wise et al. |
| 2003/0181978 A1 | 9/2003 | Brown |
| 2003/0187515 A1 | 10/2003 | Hariri |
| 2003/0206937 A1 | 11/2003 | Gertzman |
| 2003/0224518 A1 | 12/2003 | Adkisson |
| 2003/0228288 A1 | 12/2003 | Scarborough et al. |
| 2003/0235580 A1 | 12/2003 | Zhang |
| 2003/0236573 A1 | 12/2003 | Evans et al. |
| 2004/0002558 A1 | 1/2004 | McKay |
| 2004/0010320 A1 | 1/2004 | Huckle |
| 2004/0028660 A1 | 2/2004 | Hariri |
| 2004/0030406 A1 | 2/2004 | Ochi |
| 2004/0048375 A1 | 3/2004 | Alt |
| 2004/0048796 A1 | 3/2004 | Hariri |
| 2004/0052768 A1 | 3/2004 | Morrison |
| 2004/0057938 A1 | 3/2004 | Ghinelli |
| 2004/0059364 A1 | 3/2004 | Gaskin |
| 2004/0064193 A1 | 4/2004 | Evans et al. |
| 2004/0067218 A1 | 4/2004 | Casteilla |
| 2004/0077079 A1 | 4/2004 | Storgaard |
| 2004/0078077 A1 | 4/2004 | Binette |
| 2004/0078090 A1 | 4/2004 | Binette |
| 2004/0082063 A1 | 4/2004 | Deshpande |
| 2004/0091462 A1 | 5/2004 | Lin |
| 2004/0092011 A1 | 5/2004 | Wilkison |
| 2004/0096430 A1 | 5/2004 | Bauer |
| 2004/0096431 A1 | 5/2004 | Fraser |
| 2004/0097867 A1 | 5/2004 | Fraser |
| 2004/0115172 A1 | 6/2004 | Bianchi |
| 2004/0126878 A1 | 7/2004 | Ramos |
| 2004/0127987 A1 | 7/2004 | Evans |
| 2004/0166096 A1 | 8/2004 | Kolkin |
| 2004/0171146 A1 | 9/2004 | Katz |
| 2004/0181240 A1 | 9/2004 | Tseng |
| 2004/0191226 A1 | 9/2004 | Badylak |
| 2004/0197367 A1 | 10/2004 | Rezania |
| 2004/0197373 A1 | 10/2004 | Gertzman et al. |
| 2004/0229351 A1 | 11/2004 | Rodriguez |
| 2004/0230303 A1 | 11/2004 | Truncale et al. |
| 2004/0230309 A1 | 11/2004 | DiMauro et al. |
| 2004/0241146 A1 | 12/2004 | Biscup |
| 2004/0249463 A1 | 12/2004 | Bindsell |
| 2004/0265971 A1 | 12/2004 | Sato |
| 2004/0267362 A1 | 12/2004 | Hwang |
| 2005/0002910 A1 | 1/2005 | Wolfingarger |
| 2005/0003532 A1 | 1/2005 | Nakamura |
| 2005/0008626 A1 | 1/2005 | Fraser |
| 2005/0009000 A1 | 1/2005 | Wilhelm |
| 2005/0019908 A1 | 1/2005 | Hariri |
| 2005/0025755 A1 | 2/2005 | Hedrick |
| 2005/0026279 A1 | 2/2005 | Tsent |
| 2005/0033449 A1 | 2/2005 | Ashman |
| 2005/0048033 A1 | 3/2005 | Fraser |
| 2005/0048034 A1 | 3/2005 | Fraser |
| 2005/0048035 A1 | 3/2005 | Fraser |
| 2005/0048036 A1 | 3/2005 | Hedrick |
| 2005/0048644 A1 | 3/2005 | Hedrick |
| 2005/0058360 A1 | 3/2005 | Harris |
| 2005/0058629 A1 | 3/2005 | Harmon |
| 2005/0058631 A1 | 3/2005 | Kihm |
| 2005/0058632 A1 | 3/2005 | Hedrick |
| 2005/0064041 A1 | 3/2005 | O'leary |
| 2005/0074436 A1 | 4/2005 | Fraser |
| 2005/0076396 A1 | 4/2005 | Katz |
| 2005/0084961 A1 | 4/2005 | Hedrick |
| 2005/0095228 A1 | 5/2005 | Fraser |
| 2005/0100555 A1 | 5/2005 | Pitzalis |
| 2005/0112761 A1 | 5/2005 | Halvorsen |
| 2005/0118228 A1 | 6/2005 | Trieu |
| 2005/0125077 A1 | 6/2005 | Harmon |
| 2005/0136042 A1 | 6/2005 | Betz |
| 2005/0147642 A1 | 7/2005 | Laredo |
| 2005/0147959 A1 | 7/2005 | Frondoza |
| 2005/0152941 A1 | 7/2005 | Hunter |
| 2005/0152944 A1 | 7/2005 | Hunter |
| 2005/0152945 A1 | 7/2005 | Hunter |
| 2005/0152947 A1 | 7/2005 | Hunter |
| 2005/0152948 A1 | 7/2005 | Hunter |
| 2005/0153441 A1 | 7/2005 | Hedrick |
| 2005/0153442 A1 | 7/2005 | Katz |
| 2005/0154463 A1 | 7/2005 | Trieu |
| 2005/0181973 A1 | 8/2005 | Genove |
| 2005/0182463 A1 | 8/2005 | Hunter |
| 2005/0182496 A1 | 8/2005 | Hunter |
| 2005/0187639 A1 | 8/2005 | Hunter |
| 2005/0203635 A1 | 9/2005 | Hunter |
| 2005/0209705 A1 | 9/2005 | Niederauer |
| 2005/0214259 A1 | 9/2005 | Sano |
| 2005/0244239 A1 | 11/2005 | Shimp |
| 2005/0250202 A1 | 11/2005 | March |
| 2005/0255588 A1 | 11/2005 | Young |
| 2005/0260174 A1 | 11/2005 | Fraser |
| 2005/0260175 A1 | 11/2005 | Hedrick |
| 2005/0260748 A1 | 11/2005 | Chang |
| 2005/0281788 A1 | 12/2005 | De Bari |
| 2005/0281856 A1 | 12/2005 | McGlohorn et al. |
| 2005/0282275 A1 | 12/2005 | Katz |
| 2005/0283255 A1 | 12/2005 | Geremakis et al. |
| 2005/0288796 A1 | 12/2005 | Awad |
| 2006/0002900 A1 | 1/2006 | Binder |
| 2006/0018887 A1 | 1/2006 | Kadiyala |
| 2006/0030948 A1 | 2/2006 | Manrique |
| 2006/0041033 A1 | 2/2006 | Bisig et al. |
| 2006/0045872 A1 | 3/2006 | Miguel |
| 2006/0051327 A1 | 3/2006 | Johnson |
| 2006/0051865 A1 | 3/2006 | Higgins |
| 2006/0058881 A1 | 3/2006 | Trieu |
| 2006/0073124 A1 | 4/2006 | Garcia |
| 2006/0078993 A1 | 4/2006 | Phan |
| 2006/0083720 A1 | 4/2006 | Fraser |
| 2006/0084602 A1 | 4/2006 | Lynch |
| 2006/0121004 A1 | 6/2006 | Echeland |
| 2006/0136068 A1 | 6/2006 | de Brujin |
| 2006/0147424 A1 | 7/2006 | Sakuragawwa |
| 2006/0147430 A1 | 7/2006 | Sayre |
| 2006/0147433 A1 | 7/2006 | Hiles |
| 2006/0147545 A1 | 7/2006 | Scarborough |
| 2006/0153815 A1 | 7/2006 | Seyda |
| 2006/0153816 A1 | 7/2006 | Brown et al. |
| 2006/0153817 A1 | 7/2006 | Kihm |
| 2006/0153818 A1 | 7/2006 | Ohanaraj |
| 2006/0153928 A1 | 7/2006 | Kinoshita |
| 2006/0171930 A1 | 8/2006 | Seyda |
| 2006/0171932 A1 | 8/2006 | Hendricks |
| 2006/0198863 A1 | 9/2006 | De Paula |
| 2006/0204544 A1 | 9/2006 | Sunwoo et al. |
| 2006/0204556 A1 | 9/2006 | Daniels |
| 2006/0222634 A1 | 10/2006 | Clarke |
| 2006/0228339 A1 | 10/2006 | Wang |
| 2006/0228796 A1 | 10/2006 | Kolkin |
| 2006/0240555 A1 | 10/2006 | Ronfard |
| 2006/0263335 A1 | 11/2006 | France |
| 2007/0003593 A1 | 1/2007 | Wironen |
| 2007/0025973 A1 | 2/2007 | Fitzsimmons |
| 2007/0026518 A1 | 2/2007 | Healy |
| 2007/0027543 A1 | 2/2007 | Gimble |

(56) References Cited

U.S. PATENT DOCUMENTS

| | | |
|---|---|---|
| 2007/0036768 A1 | 2/2007 | Fraser |
| 2007/0048292 A1 | 3/2007 | Morita |
| 2007/0056597 A1 | 3/2007 | Fitzsimmons |
| 2007/0065938 A1 | 3/2007 | Gronthos |
| 2007/0071740 A1 | 3/2007 | Tseng |
| 2007/0071828 A1 | 3/2007 | Tseng |
| 2007/0077649 A1 | 4/2007 | Sammak |
| 2007/0082057 A1 | 4/2007 | Masinaei et al. |
| 2007/0082058 A1 | 4/2007 | Masinaei et al. |
| 2007/0083270 A1 | 4/2007 | Masinaei |
| 2007/0088437 A1 | 4/2007 | Betz et al. |
| 2007/0090101 A1 | 4/2007 | Yamazaki et al. |
| 2007/0092492 A1 | 4/2007 | Matsuda |
| 2007/0098756 A1 | 5/2007 | Behnam |
| 2007/0104692 A1 | 5/2007 | Quijano |
| 2007/0104693 A1 | 5/2007 | Quijano |
| 2007/0110732 A1 | 5/2007 | Johnson |
| 2007/0110820 A1 | 5/2007 | Behnam |
| 2007/0128171 A1 | 6/2007 | Tranquillo |
| 2007/0128173 A1 | 6/2007 | Verbruggen |
| 2007/0134210 A1 | 6/2007 | Heida |
| 2007/0134211 A1 | 6/2007 | Halvorsen |
| 2007/0148766 A1 | 6/2007 | Yoshimura |
| 2007/0154515 A1 | 7/2007 | Johnson |
| 2007/0154563 A1 | 7/2007 | Benham |
| 2007/0168038 A1 | 7/2007 | Trieu |
| 2007/0172812 A1 | 7/2007 | Ochi |
| 2007/0185585 A1 | 8/2007 | Bracy |
| 2007/0190034 A1 | 8/2007 | Paludan et al. |
| 2007/0190101 A1 | 8/2007 | McKay |
| 2007/0196421 A1 | 8/2007 | Hunter |
| 2007/0202592 A1 | 8/2007 | Kitagawa et al. |
| 2007/0207127 A1 | 9/2007 | Kato |
| 2007/0212336 A1 | 9/2007 | Fulkerson et al. |
| 2007/0212396 A1 | 9/2007 | Zheng |
| 2007/0212676 A1 | 9/2007 | Takakura |
| 2007/0213822 A1 | 9/2007 | Trieu |
| 2007/0213823 A1 | 9/2007 | Trieu |
| 2007/0213824 A1 | 9/2007 | Trieu |
| 2007/0218039 A1 | 9/2007 | Devi |
| 2007/0023272 A1 | 10/2007 | Boyce |
| 2007/0231297 A1 | 10/2007 | Smith |
| 2007/0231305 A1 | 10/2007 | Noll |
| 2007/0231401 A1 | 10/2007 | Tseng |
| 2007/0233272 A1 | 10/2007 | Boyce |
| 2007/0243130 A1 | 10/2007 | Chen et al. |
| 2007/0243131 A1 | 10/2007 | Chen et al. |
| 2007/0243172 A1 | 10/2007 | Ra |
| 2007/0248580 A1 | 10/2007 | Garcia |
| 2007/0248998 A1 | 10/2007 | Zhang |
| 2007/0249044 A1 | 10/2007 | Desai |
| 2007/0249045 A1 | 10/2007 | Gimble |
| 2007/0254041 A1 | 11/2007 | Drapeau et al. |
| 2007/0258956 A1 | 11/2007 | Higgins |
| 2007/0264239 A1 | 11/2007 | Huard |
| 2007/0264240 A1 | 11/2007 | Slavin |
| 2007/0269518 A1 | 11/2007 | Walline et al. |
| 2007/0275362 A1 | 11/2007 | Edinger |
| 2007/0276489 A1 | 11/2007 | Bindsell |
| 2007/0282456 A1 | 12/2007 | Geng |
| 2007/0292401 A1 | 12/2007 | Harmon |
| 2007/0292872 A1 | 12/2007 | Sylvester |
| 2007/0299508 A1 | 12/2007 | Morrison |
| 2008/0004713 A1 | 1/2008 | Nakamura |
| 2008/0014179 A1 | 1/2008 | Ferree |
| 2008/0015709 A1 | 1/2008 | Evans |
| 2008/0025957 A1 | 1/2008 | Lapidol |
| 2008/0026461 A1 | 1/2008 | Desphpande |
| 2008/0027546 A1 | 1/2008 | Semler |
| 2008/0030399 A1 | 2/2008 | Hunziker |
| 2008/0031858 A1 | 2/2008 | Chan |
| 2008/0033572 A1 | 2/2008 | D'Antonio |
| 2008/0038314 A1 | 2/2008 | Hunziker |
| 2008/0039940 A1 | 2/2008 | Hashimoto |
| 2008/0039955 A1 | 2/2008 | Hunziker |
| 2008/0046095 A1 | 2/2008 | Daniel |
| 2008/0050814 A1 | 2/2008 | Allickson |
| 2008/0057578 A1 | 3/2008 | Kuwabara |
| 2008/0058953 A1 | 3/2008 | Scarborough |
| 2008/0071385 A1 | 3/2008 | Binette |
| 2008/0075657 A1 | 3/2008 | Abrahams et al. |
| 2008/0075699 A1 | 3/2008 | Buhring |
| 2008/0077251 A1 | 3/2008 | Chen |
| 2008/0081369 A1 | 4/2008 | Adkisson |
| 2008/0089871 A1 | 4/2008 | Hunziker |
| 2008/0091270 A1 | 4/2008 | Miller |
| 2008/0095748 A1 | 4/2008 | Khariz |
| 2008/0108045 A1 | 5/2008 | Ghinelli |
| 2008/0112837 A1 | 5/2008 | Yoshizawa |
| 2008/0113007 A1 | 5/2008 | Kurihara |
| 2008/0131522 A1 | 6/2008 | Liu |
| 2008/0152624 A1 | 6/2008 | Paludan |
| 2008/0152629 A1 | 6/2008 | Edinger |
| 2008/0153157 A1 | 6/2008 | Yao |
| 2008/0154386 A1 | 6/2008 | Morris et al. |
| 2008/0160085 A1 | 7/2008 | Boland |
| 2008/0161410 A1 | 7/2008 | Kusters |
| 2008/0175824 A1 | 7/2008 | Heidaran |
| 2008/0175825 A1 | 7/2008 | Hampson |
| 2008/0181967 A1 | 7/2008 | Liu |
| 2008/0187518 A1 | 8/2008 | Ogle |
| 2008/0188945 A1 | 8/2008 | Boyce |
| 2008/0193554 A1 | 8/2008 | Dua |
| 2008/0199443 A1 | 8/2008 | Moos |
| 2008/0206208 A1 | 8/2008 | Casteilla |
| 2008/0206343 A1 | 8/2008 | Edinger |
| 2008/0213228 A1 | 9/2008 | Edinger |
| 2008/0213230 A1 | 9/2008 | Phillips |
| 2008/0213235 A1 | 9/2008 | Katz |
| 2008/0220569 A1 | 9/2008 | Previtali |
| 2008/0221527 A1 | 9/2008 | Bradley |
| 2008/0226595 A1 | 9/2008 | Edinger |
| 2008/0226612 A1 | 9/2008 | Treves |
| 2008/0226692 A1 | 9/2008 | Sato |
| 2008/0233088 A1 | 9/2008 | Guha |
| 2008/0233203 A1 | 9/2008 | Woodell-May |
| 2008/0248003 A1 | 10/2008 | Katz |
| 2008/0248005 A1 | 10/2008 | Phan |
| 2008/0248481 A1 | 10/2008 | Rapko |
| 2008/0254092 A1 | 10/2008 | McDevitt |
| 2008/0260703 A1 | 10/2008 | Riordan |
| 2008/0260794 A1 | 10/2008 | Lauritzen et al. |
| 2008/0269762 A1 | 10/2008 | Simon |
| 2008/0274185 A1 | 11/2008 | Mao |
| 2008/0286241 A1 | 11/2008 | Lee |
| 2008/0286267 A1 | 11/2008 | Sing |
| 2008/0286324 A1 | 11/2008 | Stolen |
| 2008/0288085 A1 | 11/2008 | Mao |
| 2008/0299087 A1 | 12/2008 | Tseng |
| 2008/0305145 A1 | 12/2008 | Shelby |
| 2008/0317718 A1 | 12/2008 | Youshimura |
| 2008/0318317 A1 | 12/2008 | Roche |
| 2009/0004161 A1 | 1/2009 | Palladino |
| 2009/0010899 A1 | 1/2009 | Palladino |
| 2009/0010982 A1 | 1/2009 | Abrahams et al. |
| 2009/0012629 A1 | 1/2009 | Yao |
| 2009/0017438 A1 | 1/2009 | Roy |
| 2009/0017439 A1 | 1/2009 | Shimko |
| 2009/0022698 A1 | 1/2009 | Ha |
| 2009/0024223 A1 | 1/2009 | Chen |
| 2009/0024224 A1 | 1/2009 | Chen |
| 2009/0024229 A1 | 1/2009 | Chen |
| 2009/0028834 A1 | 1/2009 | Siegel |
| 2009/0028919 A1 | 1/2009 | Dancu |
| 2009/0028954 A1 | 1/2009 | Bohner et al. |
| 2009/0035282 A1 | 2/2009 | Schierhotz |
| 2009/0041825 A1 | 2/2009 | Kotov |
| 2009/0043400 A1 | 2/2009 | Evans et al. |
| 2009/0053277 A1 | 2/2009 | Nagaya |
| 2009/0054983 A1 | 2/2009 | Wuisman |
| 2009/0060974 A1 | 3/2009 | Schmieding |
| 2009/0062870 A1 | 3/2009 | Milano |
| 2009/0068154 A1 | 3/2009 | Ueda |
| 2009/0074728 A1 | 3/2009 | Gronthos |

(56) References Cited

U.S. PATENT DOCUMENTS

| | | |
|---|---|---|
| 2009/0074753 A1 | 3/2009 | Lynch |
| 2009/0075381 A1 | 3/2009 | Clarke |
| 2009/0075863 A1 | 3/2009 | O'Driscoll |
| 2009/0082717 A1 | 3/2009 | Bellomo |
| 2009/0093056 A1 | 4/2009 | Iskovitz-Eldor |
| 2009/0104164 A1 | 4/2009 | Zhang |
| 2009/0130067 A1 | 5/2009 | Buscher |
| 2009/0130173 A1 | 5/2009 | Behnam et al. |
| 2009/0130756 A1 | 5/2009 | Klann |
| 2009/0136457 A1 | 5/2009 | Sing |
| 2009/0136471 A1 | 5/2009 | Heidaran |
| 2009/0136988 A1 | 5/2009 | Reschiglian |
| 2009/0142311 A1 | 6/2009 | Masuda |
| 2009/0142835 A1 | 6/2009 | Kobayashi |
| 2009/0143716 A1 | 6/2009 | Lowry |
| 2009/0143830 A1 | 6/2009 | Bourgeois |
| 2009/0149893 A1 | 6/2009 | Semler et al. |
| 2009/0155340 A1 | 6/2009 | Chu |
| 2009/0162445 A1 | 6/2009 | Masinaei |
| 2009/0163990 A1 | 6/2009 | Yang |
| 2009/0169642 A1 | 7/2009 | Fradette |
| 2009/0170059 A1 | 7/2009 | Klingerman |
| 2009/0175954 A1 | 7/2009 | Kinoshita |
| 2009/0181104 A1 | 7/2009 | Rigotti |
| 2009/0181456 A1 | 7/2009 | Hedrick |
| 2009/0185978 A1 | 7/2009 | Lundgren-Akerlund |
| 2009/0191160 A1 | 7/2009 | Hong |
| 2009/0196901 A1 | 8/2009 | Guilak |
| 2009/0202977 A1 | 8/2009 | Ott |
| 2009/0206313 A1 | 8/2009 | Beretta |
| 2009/0209020 A1 | 8/2009 | Park |
| 2009/0214649 A1 | 8/2009 | Gazit |
| 2009/0022086 A1 | 9/2009 | Lui |
| 2009/0022605 A1 | 9/2009 | Wei |
| 2009/0022704 A1 | 9/2009 | Troxel |
| 2009/0220605 A1 | 9/2009 | Wei et al. |
| 2009/0221075 A1 | 9/2009 | Dorian |
| 2009/0222086 A1 | 9/2009 | Lui |
| 2009/0228105 A1 | 9/2009 | Son |
| 2009/0232772 A1 | 9/2009 | Amano |
| 2009/0238801 A1 | 9/2009 | Woodbury |
| 2009/0239299 A1 | 9/2009 | Buss |
| 2009/0246182 A1 | 10/2009 | Castella |
| 2009/0252710 A1 | 10/2009 | Zhang |
| 2009/0252711 A1 | 10/2009 | Boquest |
| 2009/0258082 A1 | 10/2009 | Nikaido |
| 2009/0258337 A1 | 10/2009 | Yagi |
| 2009/0269315 A1 | 10/2009 | Fraser |
| 2009/0269388 A1 | 10/2009 | Sunwoo et al. |
| 2009/0274665 A1 | 11/2009 | Akabutu |
| 2009/0275011 A1 | 11/2009 | Eibl |
| 2009/0291112 A1 | 11/2009 | Truncale et al. |
| 2009/0292311 A1 | 11/2009 | Garcia |
| 2009/0297488 A1 | 12/2009 | Fraser |
| 2009/0304643 A1 | 12/2009 | Khurgei |
| 2009/0304644 A1 | 12/2009 | Hadrick |
| 2009/0304646 A1 | 12/2009 | Sakurada |
| 2009/0304654 A1 | 12/2009 | Lue |
| 2009/0311223 A1 | 12/2009 | Ichim |
| 2010/0003299 A1 | 1/2010 | Tseng |
| 2010/0008967 A1 | 1/2010 | Grande |
| 2010/0015104 A1 | 1/2010 | Fraser |
| 2010/0015204 A1 | 1/2010 | Hedrick |
| 2010/0015712 A1 | 1/2010 | Sakuragawa |
| 2010/0022005 A1 | 1/2010 | March |
| 2010/0003488 A1 | 2/2010 | Walline et al. |
| 2010/0028306 A1 | 2/2010 | Clarke |
| 2010/0028308 A1 | 2/2010 | Knipper |
| 2010/0028407 A1 | 2/2010 | Del |
| 2010/0036503 A1 | 2/2010 | Chen |
| 2010/0047213 A1 | 2/2010 | Zeitlin |
| 2010/0047214 A1 | 2/2010 | Abramson |
| 2010/0047351 A1 | 2/2010 | Zeitlin |
| 2010/0049322 A1 | 2/2010 | McKay |
| 2010/0055757 A1 | 3/2010 | Lin |
| 2010/0068180 A1 | 3/2010 | Marshall |
| 2010/0069975 A1 | 3/2010 | Auge |
| 2010/0080779 A1 | 4/2010 | Smith |
| 2010/0082113 A1 | 4/2010 | Gingras |
| 2010/0098669 A1 | 4/2010 | Fernandez |
| 2010/0098673 A1 | 4/2010 | D'Antonio |
| 2010/0098739 A1 | 4/2010 | Katz |
| 2010/0098743 A1 | 4/2010 | Nikaido |
| 2010/0104539 A1 | 4/2010 | Daniel |
| 2010/0104542 A1 | 4/2010 | Austen, Jr. |
| 2010/0105100 A1 | 4/2010 | Sakurada |
| 2010/0106233 A1 | 4/2010 | Grant |
| 2010/0111897 A1 | 5/2010 | Katz et al. |
| 2010/0111906 A1 | 5/2010 | Scarborough et al. |
| 2010/0112031 A1 | 5/2010 | Katz |
| 2010/0112084 A1 | 5/2010 | Wu |
| 2010/0112543 A1 | 5/2010 | Ngo |
| 2010/0112695 A1 | 5/2010 | Min |
| 2010/0112696 A1 | 5/2010 | Min |
| 2010/0114013 A1 | 5/2010 | Boyden |
| 2010/0119492 A1 | 5/2010 | Hans |
| 2010/0119496 A1 | 5/2010 | Wilkison |
| 2010/0120069 A1 | 5/2010 | Sakurada |
| 2010/0124563 A1 | 5/2010 | Coleman |
| 2010/0124569 A1 | 5/2010 | Abbot |
| 2010/0124776 A1 | 5/2010 | Shi |
| 2010/0129328 A1 | 5/2010 | Sing |
| 2010/0129330 A1 | 5/2010 | Wilkison |
| 2010/0050878 A1 | 6/2010 | Bellomo |
| 2010/0136114 A1 | 6/2010 | Mao |
| 2010/0136668 A1 | 6/2010 | Hedrick |
| 2010/0143312 A1 | 6/2010 | Hariri |
| 2010/0143477 A1 | 6/2010 | Siegel |
| 2010/0145473 A1 | 6/2010 | Yannas |
| 2010/0150878 A1 | 6/2010 | Bellomo |
| 2010/0151435 A1 | 6/2010 | Thatte |
| 2010/0151574 A1 | 6/2010 | Matsuyama |
| 2010/0158876 A1 | 6/2010 | Alessandri |
| 2010/0158975 A1 | 6/2010 | Naughton |
| 2010/0166716 A1 | 7/2010 | Serikov |
| 2010/0166824 A1 | 7/2010 | Naughton |
| 2010/0166879 A1 | 7/2010 | Shim |
| 2010/0168022 A1 | 7/2010 | Centeno |
| 2010/0173352 A1 | 7/2010 | Blanc-Brude |
| 2010/0173411 A1 | 7/2010 | Katz |
| 2010/0178274 A1 | 7/2010 | Sekiya |
| 2010/0178861 A1 | 7/2010 | Lee |
| 2010/0183568 A1 | 7/2010 | Matuyama |
| 2010/0183571 A1 | 7/2010 | Paludan |
| 2010/0196333 A1 | 8/2010 | Gaskins |
| 2010/0196439 A1 | 8/2010 | Beck |
| 2010/0196480 A1 | 8/2010 | Hiles |
| 2010/0209387 A1 | 8/2010 | Wasielewski |
| 2010/0209408 A1 | 8/2010 | Stepen |
| 2010/0209470 A1 | 8/2010 | Mohan |
| 2010/0215714 A1 | 8/2010 | Messina |
| 2010/0215717 A1 | 8/2010 | Soker |
| 2010/0027399 A1 | 9/2010 | Funaki |
| 2010/0221231 A1 | 9/2010 | Smith |
| 2010/0221268 A1 | 9/2010 | Parolini |
| 2010/0233131 A1 | 9/2010 | Kang |
| 2010/0233139 A1 | 9/2010 | Hedrick |
| 2010/0239539 A1 | 9/2010 | Sing |
| 2010/0239540 A1 | 9/2010 | Brinchmann |
| 2010/0239542 A1 | 9/2010 | Young |
| 2010/0239543 A1 | 9/2010 | Young |
| 2010/0249758 A1 | 9/2010 | Sengun |
| 2010/0254954 A1 | 10/2010 | Sakuragawa |
| 2010/0255115 A1 | 10/2010 | Mohan |
| 2010/0256774 A1 | 10/2010 | Wang |
| 2010/0260843 A1 | 10/2010 | Messina |
| 2010/0261276 A1 | 10/2010 | Park |
| 2010/0266553 A1 | 10/2010 | Ra |
| 2010/0267107 A1 | 10/2010 | Zuba-Surma |
| 2010/0272694 A1 | 10/2010 | Yang |
| 2010/0272803 A1 | 10/2010 | Mistry |
| 2010/0278783 A1 | 11/2010 | Rouy |
| 2010/0279405 A1 | 11/2010 | Peterson |
| 2010/0285521 A1 | 11/2010 | Vossman |

(56) References Cited

U.S. PATENT DOCUMENTS

| | | |
|---|---|---|
| 2010/0285580 A1 | 11/2010 | Evans |
| 2010/0285582 A1 | 11/2010 | Choung |
| 2010/0285588 A1 | 11/2010 | Stubbers |
| 2010/0291042 A1 | 11/2010 | Crawford |
| 2010/0291219 A1 | 11/2010 | Karp |
| 2010/0291679 A1 | 11/2010 | Edinger |
| 2010/0292791 A1 | 11/2010 | Lu |
| 2010/0297082 A1 | 11/2010 | Guelcher |
| 2010/0297089 A1 | 11/2010 | Oh |
| 2010/0297689 A1 | 11/2010 | Edinger |
| 2010/0030774 A1 | 12/2010 | Hedrick |
| 2010/0303766 A1 | 12/2010 | Miyaji |
| 2010/0303773 A1 | 12/2010 | Yang |
| 2010/0303774 A1 | 12/2010 | Hedrick |
| 2010/0304477 A1 | 12/2010 | Buscher |
| 2010/0305696 A1 | 12/2010 | Mao |
| 2010/0310527 A1 | 12/2010 | Alt |
| 2010/0312355 A1 | 12/2010 | Yahav |
| 2010/0330047 A1 | 12/2010 | Valorani |
| 2010/0330182 A1 | 12/2010 | Young |
| 2010/0330672 A1 | 12/2010 | Sakuragawa |
| 2010/0330673 A1 | 12/2010 | Fraser |
| 2011/0002904 A1 | 1/2011 | Johnson |
| 2011/0003387 A1 | 1/2011 | Abbot |
| 2011/0003388 A1 | 1/2011 | Fraser |
| 2011/0008300 A1 | 1/2011 | Wouters |
| 2011/0008397 A1 | 1/2011 | Cohen |
| 2011/0008763 A1 | 1/2011 | Lee |
| 2011/0009963 A1 | 1/2011 | Binnette |
| 2011/0014701 A1 | 1/2011 | Ghosh |
| 2011/0020196 A1 | 1/2011 | Grippi |
| 2011/0020293 A1 | 1/2011 | Woda |
| 2011/0027871 A1 | 2/2011 | Gaskins |
| 2011/0027879 A1 | 2/2011 | Katz |
| 2011/0028903 A1 | 2/2011 | Schmieding |
| 2011/0038903 A1 | 2/2011 | Singh |
| 2011/0039332 A1 | 2/2011 | Sakurada |
| 2011/0040388 A1 | 2/2011 | Alini |
| 2011/0045044 A1 | 2/2011 | Masinaei |
| 2011/0045084 A1 | 2/2011 | Walline et al. |
| 2011/0045588 A1 | 2/2011 | Kawase |
| 2011/0045949 A1 | 2/2011 | Kunihara |
| 2011/0046628 A1 | 2/2011 | Jamali |
| 2011/0046758 A1 | 2/2011 | Soo et al. |
| 2011/0059178 A1 | 3/2011 | Semler et al. |
| 2011/0064701 A1 | 3/2011 | Young |
| 2011/0064705 A1 | 3/2011 | Lanza |
| 2011/0064810 A1 | 3/2011 | Ghanawi |
| 2011/0065083 A1 | 3/2011 | Shimko |
| 2011/0070205 A1 | 3/2011 | Crawford |
| 2011/0070312 A1 | 3/2011 | Wei et al. |
| 2011/0070647 A1 | 3/2011 | Oezawa |
| 2011/0077679 A1 | 3/2011 | Moran |
| 2011/0081326 A1 | 4/2011 | Hantash |
| 2011/0086008 A1 | 4/2011 | Hoemann |
| 2011/0086068 A1 | 4/2011 | Gourdie |
| 2011/0086426 A1 | 4/2011 | Freund |
| 2011/0087338 A1 | 4/2011 | Seimionow |
| 2011/0091517 A1 | 4/2011 | Ginette |
| 2011/0097381 A1 | 4/2011 | Binette |
| 2011/0098826 A1 | 4/2011 | Mauck |
| 2011/0104133 A1 | 5/2011 | Tseng |
| 2011/0104735 A1 | 5/2011 | Bueher |
| 2011/0108644 A1 | 5/2011 | Morris et al. |
| 2011/0110896 A1 | 5/2011 | Kleinsek |
| 2011/0110898 A1 | 5/2011 | Kleinsek |
| 2011/0111497 A1 | 5/2011 | Tamai |
| 2011/0111499 A1 | 5/2011 | Torihashi |
| 2011/0117167 A1 | 5/2011 | Sanford |
| 2011/0117171 A1 | 5/2011 | Melican |
| 2011/0117650 A1 | 5/2011 | Riodan |
| 2011/0124105 A1 | 5/2011 | Hampson |
| 2011/0129447 A1 | 6/2011 | Meretzki |
| 2011/0143331 A1 | 6/2011 | Roy |
| 2011/0143429 A1 | 6/2011 | Chun |
| 2011/0150845 A1 | 6/2011 | Parekkadan |
| 2011/0150846 A1 | 6/2011 | Van |
| 2011/0151005 A1 | 6/2011 | Ylikomi |
| 2011/0151011 A1 | 6/2011 | Flynn |
| 2011/0158959 A1 | 6/2011 | Mcintosh |
| 2011/0158966 A1 | 6/2011 | Seilgman |
| 2011/0158968 A1 | 6/2011 | Fraser |
| 2011/0158995 A1 | 6/2011 | Mcintosh |
| 2011/0171726 A1 | 7/2011 | Kang |
| 2011/0172777 A1 | 7/2011 | Sybert et al. |
| 2011/0177132 A1 | 7/2011 | Allon |
| 2011/0177134 A1 | 7/2011 | Harmon |
| 2011/0177593 A1 | 7/2011 | Funaki |
| 2011/0182962 A1 | 7/2011 | McKay |
| 2011/0182963 A1 | 7/2011 | McKay |
| 2011/0183001 A1 | 7/2011 | Rosson |
| 2011/0184381 A1 | 7/2011 | Shintani |
| 2011/0189140 A1 | 8/2011 | Christman |
| 2011/0189254 A1 | 8/2011 | Liu |
| 2011/0189696 A1 | 8/2011 | Gronthos |
| 2011/0195052 A1 | 8/2011 | Benham et al. |
| 2011/0262554 A1 | 10/2011 | Masinaei et al. |
| 2011/0274668 A1 | 11/2011 | Scarborough et al. |
| 2012/0009230 A1 | 1/2012 | Orapeu |
| 2012/0046758 A1 | 2/2012 | Evans |
| 2012/0053692 A1 | 3/2012 | Voor |
| 2012/0088721 A1 | 4/2012 | Shiedlin et al. |
| 2012/0093895 A1 | 4/2012 | Song |
| 2012/0100225 A1 | 4/2012 | McKay |
| 2012/0116515 A1 | 5/2012 | Semler |
| 2012/0121660 A1 | 5/2012 | Akella |
| 2012/0212913 A1 | 5/2012 | Walline et al. |
| 2012/0143334 A1 | 6/2012 | Boyce |
| 2012/0156265 A1 | 6/2012 | Binette |
| 2012/0189704 A1 | 7/2012 | Ben-Shalom et al. |
| 2012/0195952 A1 | 8/2012 | King |
| 2012/0205274 A1 | 8/2012 | Sunwoo et al. |
| 2012/0213859 A1 | 8/2012 | Shelby |
| 2012/0251609 A1 | 10/2012 | Huang |
| 2012/0258178 A1 | 10/2012 | Behnam et al. |
| 2012/0259425 A1 | 10/2012 | Brahm |
| 2012/0269892 A1 | 10/2012 | Mussand |
| 2012/0294896 A1 | 11/2012 | Roper |
| 2012/0294898 A1 | 11/2012 | Hubbard et al. |
| 2012/0330423 A1 | 12/2012 | Lin |
| 2013/0013071 A1 | 1/2013 | Betz et al. |
| 2013/0073041 A1 | 3/2013 | Seifert |
| 2013/0115255 A1 | 5/2013 | Bosley |
| 2013/0136777 A1 | 5/2013 | Behnam |
| 2013/0149356 A1 | 6/2013 | Mills |
| 2013/0158676 A1 | 6/2013 | Hayzlett |
| 2013/0189338 A1 | 7/2013 | Drapeau |
| 2013/0190891 A1 | 7/2013 | Drapeau et al. |
| 2013/0190893 A1 | 7/2013 | Roock |
| 2013/0195805 A1 | 8/2013 | Wei et al. |
| 2013/0261634 A1 | 10/2013 | McKay |
| 2013/0273121 A1 | 10/2013 | Mizuno |
| 2013/0287741 A1 | 10/2013 | Stillwell |
| 2013/0287753 A1 | 10/2013 | Centeno |
| 2013/0295081 A1 | 11/2013 | Guelcher et al. |
| 2013/0297038 A1 | 11/2013 | McKay |
| 2013/0316012 A1 | 11/2013 | Gaskins et al. |
| 2013/0331898 A1 | 12/2013 | Nyemsceck |
| 2014/0010891 A1 | 1/2014 | Morris et al. |
| 2014/0031937 A1 | 1/2014 | McKay |
| 2014/0065238 A1 | 3/2014 | Wolfinbarger |
| 2014/0121771 A1 | 5/2014 | Chitre |
| 2014/0195005 A1 | 7/2014 | McKay |
| 2014/0205674 A1 | 7/2014 | Wei |
| 2014/0207235 A1 | 7/2014 | Drapeau |
| 2014/0208980 A1 | 7/2014 | Song et al. |
| 2014/0212471 A1 | 7/2014 | Drapeau et al. |
| 2014/0212499 A1 | 7/2014 | Cooper et al. |
| 2014/0220142 A1 | 8/2014 | Song et al. |
| 2014/0242044 A1 | 8/2014 | Evans et al. |
| 2014/0261855 A1 | 9/2014 | Shimko et al. |
| 2014/0277569 A1 | 9/2014 | Lange |
| 2014/0277570 A1 | 9/2014 | Behnam et al. |
| 2014/0287017 A1 | 9/2014 | Altschuler |

(56) References Cited

U.S. PATENT DOCUMENTS

| | | |
|---|---|---|
| 2014/0296623 A1 | 10/2014 | Owens et al. |
| 2014/0302112 A1 | 10/2014 | Behnam et al. |
| 2014/0314821 A1 | 10/2014 | Scifert et al. |
| 2014/0314822 A1 | 10/2014 | Carter et al. |
| 2014/0341964 A1 | 11/2014 | McKay et al. |
| 2015/0010642 A1 | 1/2015 | Anderson et al. |
| 2015/0030684 A1 | 1/2015 | Pomrink et al. |
| 2015/0037386 A1 | 2/2015 | Shimp et al. |
| 2015/0110747 A1 | 4/2015 | Bhat et al. |
| 2015/0110748 A1 | 4/2015 | Shat et al. |
| 2015/0140096 A1 | 5/2015 | Malinin |
| 2015/0224227 A1 | 8/2015 | Bhat et al. |
| 2015/0251361 A1 | 9/2015 | Meyer et al. |
| 2015/0258243 A1 | 9/2015 | Malinin |
| 2015/0283168 A1 | 10/2015 | Ben-Shalom et al. |
| 2015/0283182 A1 | 10/2015 | Guelcher et al. |
| 2015/0283296 A1 | 10/2015 | Cao et al. |
| 2015/0297793 A1 | 10/2015 | McKay |
| 2016/0331554 A1 | 1/2016 | Manrique et al. |
| 2016/0038639 A1 | 2/2016 | Carter et al. |
| 2016/0081803 A1 | 3/2016 | McKay |
| 2016/0082155 A1 | 3/2016 | Uveges et al. |
| 2016/0115451 A1 | 4/2016 | Wolfinbarger et al. |
| 2016/0135954 A1 | 5/2016 | Schlachter |
| 2016/0136329 A1 | 5/2016 | Schlachter |
| 2016/0144075 A1 | 5/2016 | Behnam |
| 2016/0158408 A1 | 6/2016 | Pomrink et al. |
| 2016/0166303 A1 | 6/2016 | Schlacter |
| 2016/0166729 A1 | 6/2016 | Mossaad |
| 2016/0175480 A1 | 6/2016 | Altschuler et al. |
| 2016/0213811 A1 | 7/2016 | Chen et al. |
| 2016/0256607 A1 | 9/2016 | Francis et al. |
| 2016/0302931 A1 | 10/2016 | Forsell |
| 2016/0310636 A1 | 10/2016 | Scifert et al. |
| 2016/0361171 A1 | 12/2016 | Wang et al. |
| 2017/0000624 A1 | 1/2017 | Schallenberger et al. |
| 2017/0106119 A1 | 4/2017 | Skinner et al. |
| 2017/0119927 A1 | 5/2017 | Cooper et al. |
| 2017/0119929 A1 | 5/2017 | Bhat et al. |
| 2017/0119933 A1 | 5/2017 | McKay |
| 2017/0128624 A1 | 5/2017 | Muir |
| 2017/0136149 A1 | 5/2017 | Wei et al. |
| 2017/0165323 A1 | 6/2017 | Soo et al. |
| 2017/0203006 A1 | 7/2017 | Carter et al. |
| 2017/0203007 A1 | 7/2017 | Ringeisen et al. |
| 2017/0216491 A1 | 8/2017 | Schlachter et al. |
| 2017/0266348 A1 | 9/2017 | Gaskins et al. |
| 2017/0296357 A1 | 10/2017 | McKay et al. |
| 2017/0296581 A1 | 10/2017 | Behnam et al. |
| 2017/0312079 A1 | 11/2017 | Schlacter et al. |
| 2017/0319626 A1 | 11/2017 | Wei |
| 2017/0326162 A1 | 11/2017 | DiMauro |
| 2017/0326180 A1 | 11/2017 | DiMauro |
| 2017/0333485 A1 | 11/2017 | Marchosky |
| 2018/0000595 A1 | 1/2018 | Carter et al. |
| 2018/0021382 A1 | 1/2018 | Wei et al. |
| 2018/0028317 A1 | 1/2018 | Schlachter |
| 2018/0093014 A1 | 4/2018 | McKay |
| 2018/0104381 A1 | 4/2018 | Southard et al. |
| 2018/0133363 A1 | 5/2018 | Chen et al. |
| 2018/0177916 A1 | 6/2018 | Masinei et al. |
| 2018/0185548 A1 | 7/2018 | McKay |
| 2018/0193077 A1 | 7/2018 | Schlachter et al. |
| 2019/0091942 A1 | 3/2019 | Meyer et al. |

FOREIGN PATENT DOCUMENTS

| | | |
|---|---|---|
| CA | 25415061 | 11/2010 |
| CA | 2986702 | 11/2016 |
| EP | 0333328 | 9/1989 |
| EP | 0518389 | 12/1992 |
| EP | 0669138 | 8/1995 |
| EP | 1127581 | 8/2001 |
| EP | 1263365 | 12/2002 |
| EP | 1283693 | 2/2003 |
| EP | 1477176 | 11/2004 |
| EP | 1505943 | 2/2005 |
| EP | 1549358 | 7/2005 |
| EP | 1847277 | 10/2007 |
| EP | 2032071 | 3/2009 |
| EP | 2129406 | 9/2009 |
| EP | 3297694 | 3/2018 |
| JP | 2004210713 | 7/2004 |
| JP | 2006230749 | 9/2006 |
| JP | 2007054015 | 3/2007 |
| KR | 20040020413 | 3/2004 |
| WO | 1989/004646 | 6/1989 |
| WO | 1989/007425 | 8/1989 |
| WO | 1995/15776 | 6/1995 |
| WO | 1998/037903 | 9/1998 |
| WO | 1999/039757 | 2/1999 |
| WO | 2000/045871 | 8/2000 |
| WO | 2000/073421 | 12/2000 |
| WO | 2001/023532 | 4/2001 |
| WO | 2002/005750 | 1/2002 |
| WO | 2002002156 | 1/2002 |
| WO | 2002005750 A2 | 1/2002 |
| WO | 2002/005750 | 2/2002 |
| WO | 2002/028322 | 4/2002 |
| WO | 2002/032348 | 4/2002 |
| WO | 2002/036049 | 8/2002 |
| WO | 2002/068010 | 9/2002 |
| WO | 2003/077794 | 9/2003 |
| WO | 2004/000164 | 12/2003 |
| WO | 2003099236 | 12/2003 |
| WO | 20030099236 | 12/2003 |
| WO | 2004016196 | 2/2004 |
| WO | 2004016297 | 2/2004 |
| WO | 20040016297 | 2/2004 |
| WO | 2004/033635 | 4/2004 |
| WO | 2004026244 | 4/2004 |
| WO | 2004/045372 | 6/2004 |
| WO | 2004045372 A2 | 6/2004 |
| WO | 20040045372 | 6/2004 |
| WO | 2004/071543 | 8/2004 |
| WO | 2004/078225 | 9/2004 |
| WO | 2004/112854 | 12/2004 |
| WO | 2005/009498 | 2/2005 |
| WO | 2005/032435 | 4/2005 |
| WO | 2005/051446 | 6/2005 |
| WO | 2005/072656 | 8/2005 |
| WO | 2006/076712 | 7/2006 |
| WO | 2006/089023 | 8/2006 |
| WO | 2006/094247 | 9/2006 |
| WO | 2007/090180 | 2/2007 |
| WO | 2007/037572 | 4/2007 |
| WO | 2007/038686 | 4/2007 |
| WO | 2007/124198 | 11/2007 |
| WO | 2007133722 | 11/2007 |
| WO | 20070133722 | 11/2007 |
| WO | 2008/003042 | 1/2008 |
| WO | 2008/026858 | 3/2008 |
| WO | 2008/072230 | 6/2008 |
| WO | 2008/073628 | 6/2008 |
| WO | 2009/036279 | 3/2009 |
| WO | 2009/038676 | 3/2009 |
| WO | 2009/082554 | 7/2009 |
| WO | 2009/102452 | 8/2009 |
| WO | 2009/102792 | 8/2009 |
| WO | 2010/016942 | 2/2010 |
| WO | 2010/146577 | 12/2010 |
| WO | 2011/005200 | 1/2011 |
| WO | 2009/036279 | 5/2012 |
| WO | 2012/058042 | 5/2012 |
| WO | 2012/060964 | 5/2012 |
| WO | 2012/060991 | 5/2012 |
| WO | 2012/061024 | 5/2012 |
| WO | 2012/135205 | 10/2012 |
| WO | 2012/0135205 | 10/2012 |
| WO | 2013/047937 | 4/2013 |
| WO | 2013/109663 | 7/2013 |
| WO | 2013/188336 | 12/2013 |
| WO | 2014/145854 | 9/2014 |
| WO | 2014/151091 | 9/2014 |

(56) References Cited

FOREIGN PATENT DOCUMENTS

| WO | 2015054547 | 9/2014 |
|---|---|---|
| WO | 2015/054547 | 4/2015 |
| WO | 2015/120221 | 8/2015 |
| WO | 2016/048657 | 3/2016 |
| WO | 2016/123583 | 8/2016 |
| WO | 2016/187413 | 11/2016 |
| WO | 2017/218545 | 2/2017 |
| WO | 2017/070036 | 4/2017 |
| WO | 2017/074894 | 5/2017 |
| WO | 2017/132038 | 8/2017 |
| WO | 2017/189721 | 11/2017 |
| WO | 2017/196595 | 11/2017 |

OTHER PUBLICATIONS

Benjamin, "The Fascia of the limbs and back—a review", Journal of Anatomy, vol. 214, (2009), pp. 1-18.
Final Office Action for U.S. Appl. No. 13/108,856, dated May 14, 2013.
Adipose Tissue, http://users.rcn.com/jkimball.ma.ultranet!BiologyPages/A/AdiposeTissue.html, dated Dec. 1, 2009, printedApr. 15, 2011, 1 page.
Alsalameh et al., "Identification of Mesenchymal Progenitor Cells in Normal and Osteoarthritic Human Articular cartilage", Arthritis & Rheumatism, vol. 50, No. 5, May 2004, pp. 1522-1532.
Alvarez-Buylla et al., "For the Long Run: Maintaining Germinal Niches in the Adult Brain", Neuron, vol. 41, Mar. 4, 2004 pp. 683-686.
Amir et al., "Harvesting Large Fascia Lala Sheaths: A Rational Approach", Skull Base Surgery, vol. 10, No. 1, (2000), pp. 29-34.
Anderson et al., "The performance of human mesenchymal stem cells encapsulated in cell-degradable polymer-peptide hydrogels", Biomaterials, vol. 32, (2011 ), pp. 3564-3574.
Antuna-Puente et al., "Adipokines: The missing link between insulin resistance and obesity", Diabetes & Metabolism, vol. 34, (2008), pp. 2-11.
Bacterin International, Inc.: OsteoSponge®, dated Mar. 2006, from http://odev.com/health_professional/pdfs/spine/Osteosponge%20Brochure.pdf. 5 pages.
Badylak et al., "The extracellular matrix as a biologic scaffold material", Biomaterials, vol. 28, (2007), pp. 3587-3593.
Bakopoulou et al., "Comparative Analysis of in vitro osteo/odontogenic differentiation potential of human dental pulp stem cells (DPSCs) and stem cells from the apical papilla (SCAP)", Archives of Oral Biology, vol. 56, Jan. 10, 2011, pp. 709-721.
Bakopoulou et al., "Effects of HEMA and TEDGMA on the in vitro odontogenic differentiation potential of human pulp stern/progenitor cells derived from decidous teeth", Dental Materials, vol. 27, Apr. 11, 2011, pp. 608-617.
Barker et al., "Leucine-rich repeat-containing G-protein-coupled receptors as markers of adult stem cells", Gastroenterology, vol. 138, No. 5, May 2010, pp. 1681-1696.
Becher et al., "Regeneration of the vascular compartment", Herz, vol. 35, (2010), pp. 342-351.
Bi et al., "Identification of tendon stem/progenitor cells and the role of the extracellular matrix in their niche", Nature Medicine, vol. 13, No. 10, Oct. 2007, pp. 1219-1227.
Bieliauskas et al.; "Isoform-selective histone deacetylas inhibitors". Chemical Society Reviews. vol. 37, (2008), pp. 1402-1412.
Bigham et al., "Xengogenic Demineralized bone matrix and fresh autogenous cortical bone effects on experimental bone healing: radiological, histopathological and biomechanical evaluation", Journal of Orthopaed Traumatol, vol. 9, ( 2008), pp. 73-80.
Blanpain et al., "Epidermal homeostasis: a balancing act of stem cells in the skin", Nat. Rev. Mol. Cell Bioi., vol. 10, No. 3, Mar. 2009, pp. 207-217.
Blanpain, "Skin regeneration and repair", Nature, vol. 464, Apr. 11, 2010, pp. 686-687.

Boonen et al., "The Muscle Stem Cell Niche: Regulation of Satellite Cells During Regeneration", Tissue Engineering: Part B, vol. 14, No. 4, (2008) pp. 419-431.
Brachium to Hand Musculature, http://www.ptcentral.com/muscles/musclearms.html, printed Apr. 15, 2011, 12 pages.
Bradner et al., "Chemical phylogenetics of histone deacetylases", Nature Chemical Biology, vol. 6, Mar. 2010, pp. 238-240.
Breitling et al., "Robust signaling networks of the adipose secretome", Trends in Endocrinology and Metabolism, vol. 20, No. 1, (2008), pp. 1-7.
Brochhausen et al., "Signalling molecules and growth factors for tissue engineering of cartilage—what can we learn frorr the growth plate?", Journal of Tissue Engineering and Regenerative Medicine, vol. 3, (2009), pp. 416-429.
Brown et al., "Basic Science Review on Adipose Tissue for Clinicians", Plastic and Reconstructive Surgery, vol. 126, No. 6, Dec. 2010, pp. 1936-1946.
Brown et al., "Comparison of Three Methods for the Derivation of a Biologic Scaffold Composed of Adipose Tissue Extracellular Matrix", Tissue Engineering: Part C, vol. 17, No. 4 (2011), pp. 411-421.
Butler et al., "Dentin Extracellular Matrix (ECM) Proteins: Comparison to Bone ECM and Contribution to Dynamics of Dentinogenesis", Connective Tissue Research, vol. 44 (Suppl. 1), (2003), pp. 171-178.
Chapman, "Toward Lung Regeneration", The New England Journal of Medicine, vol. 364, No. 19, May 12, 2011, pp. 1867-1868.
Chen, "Extracellular Matrix Provides an Optimal Niche for the Maintenance and Propagation of Mesenchymal Stem Cells", Birth Defects Research {Part C), vol. 90, {2010), pp. 45-54.
Cheng, et al., "Chondrogenic Differentiation of Adipose-Derived Adult Stem Cells by a Porous Scaffold Derived from Native Articular Cartilage Extracellular Matrix", Tissue Engineering: Part A, vol. 15, No. 2, {2009), pp. 231-241.
Cheng, et al., "Comparison of Potentials Between Stem Cells Isolated from Human Anterior Cruciate Ligament and Bone Marrow for Ligament Tissue Engineering", Tissue Engineering: Part A, vol. 16, No. 7, {2010), pp. 2237-2253.
Choi et al., "Decellularized extracellular matrix derived from human adipose tissue as a potential scaffold for allograft issue engineering", J Biomed Mater Res A., Mar. 29, 2011, 1 page http://www.ncbi.nlm.hih.gov/pubmed printed Apr. 5, 2011 {abstract only.
Choi et al., "Fabrication of Porous Extracellular Matrix Scaffolds from Human Adipose Tissue", Tissue Engineering: Part C, vol. 16, No. 3, {2010), pp. 387-396.
Chun et al., "Analysis of the Soluble Human Tooth Proteome and Its Ability to Induce Dentin/Tooth Regeneration", issue Engineering: Part A, vol. 17, Nos. 1 & 2, {2011 }, pp. 181-191.
Cinti, "The Adipose Organ", Prostaglandins Leukotrienes Essential Fatty Acids, vol. 73, No. 1, Jul. 2005, pp. 9-15.
Cosgrove et al., "A home away from home: Challenges and opportunities in engineering in vitro muscle satellite cell niches", Differentiation, vol. 78, {2009), pp. 184-194.
Cowin, ed., "Bone Mechanics", CRC Press, Inc., 1989, pp. 1-13.
Davisson et al., "Novel Allograft Sponge Supports Fill of Osteochondral Defects in Caprine Model," 55th Annual Meeting of the Orthopaedic Research Society (Feb. 2009), Paper No. 57, 1 page.
Diaz-Prado et al., "Isolation and Characterization of Mesenchymal Stem Cells from Human Amniotic Membrane", Tissue Engineering: Part C, vol. 17, No. 1, (2011 ), pp. 49-59.
DiBella et al., "Injection of Demineralized Bone Matrix with Bone Marrow Concentrate Improves Healing in Unicameral Bone Cyst," Clinical Orthopaedics and Related Research, Symposium: Highlights of the ISOLS/MSTS, 2009 Meeting, 2009), 9 pages.
Discher et al., "Growth factors, matrices, and forces combine and control stem cells", Science, vol. 324, No. 5935, Jun. 26, 2009, pp. 1673-1677.
Fascia, Wikipedia, http://en.wikipedia.org/wiki/Fascia, printed May 16, 2011,3 pages.
Feng et al., "Extracellular Matrix in Disc Degeneration", The Journal of Bone & Joint Surgery, vol. 88, (2006), pp. 25-2S.

(56) References Cited

OTHER PUBLICATIONS

Fernandez-Tresguerres Hernandez-Gil, et al., "Physiological bases of bone regeneration I. Histology and physiology o bone tissue", Med. Oral Patel Oral Cir. Bucal, vol. 11, (2006), pp. E47-E51.
Final Office Action for U.S. Appl. No. 13/690,542, dated Jul. 2, 2015.
Final Office Action for U.S. Appl. No. 13/828,525, dated Jul. 1, 2016.
Final Office Action for U.S. Appl. No. 13/828,525, dated Jul. 24, 2015.
Final Office Action for U.S. Appl. No. 13/948,798, dated Mar. 14, 2014.
Final Office Action for U.S. Appl. No. 13/828,525, dated May 12, 2017.
Final Office Action for U.S. Appl. No. 15/159,406, dated May 9, 2018.
Risau et al., "Vasculogenesis", Annual Review of Cell and Developmental Biology, vol. 11, {1995), pp. 73-91.
Sandberg, "Matrix in Cartilage and Bone Development: Current Views on the Function and Regulation of Major Organic Components", Annals of Medicine, vol. 23, {1991), pp. 207-217.
Sandjeu et al.,"Desmosealin and other Components of the Epidermal Extracellular Matrix", Journal of Physiology and Pharmacology, vol. 60, Suppl. 4, {2009), pp. 23-30.
Schwam et al., Human Amniotic Membrane Transplantation for the Treatment of Ocular Surface Disease, DCMS Northeast Florida Medicine Journal, http://www.dmcsonline.org/jax-medicine/2002journals/augsept2002/amniotic.htm, Aug.-Sep. 2002 (printed Aug. 30, 2010), 6 pages.
Shamji et al., "Proinflammatory Cytokine Expression Profile in Degenerated and Herniated Human Intervertebral Disc Tissues", Arthritis & Rheumatism, vol. 62, No. 7, Jul. 2010, pp. 1974-1982.
Sheikh et al., "Cell-Cell Connection to Cardiac Disease", TCM, vol. 19, No. 6, {2009), pp. 182-190.
Shoulders et al, "Collagen Structure and Stability", Annu Rev Biochem., vol. 78, {2009), pp. 927-958.
Smith et al., "Degeneration and regeneration of the intervertebral disc: lessons from development", Dis. Model Mech., vol. 4, No. 1, Jan. 2011, pp. 31-41.
Som et al., "Fascia and Spaces of the Neck", Head and Neck Imaging, 4th Ed., Chapter 34, Mosby, Inc., {2003), pp. 1805-1827.
Somerman et al., "Human Dentin Matrix Induces Cartilage Formation in vitro Mesenchymal Cells Derived from embryonic Muscle", J Den Res, vol. 66, No. 10, Oct. 1987, pp. 1551-1558.
Steiner et al., "Mesenchymal Stem Cell Characteristics of Human Anterior Cruciate Ligament Outgrowth cells", Tissue Eng., Part A, vol. 17, No. 9 and 10, pp. 1375-1388, 2011.
Stem Cell Basics, U.S. Department of Health and Human Services, National Institutes of Health, http://stemcells.hih/gov/info/basics/, last updated: Apr. 28, 2009, 26 pages.
The Hosford Muscle Tables: Skeletal Muscles of the Human Body, http://www.ptcentral.com/muscles/, printed Apr. 15, 2011, 3 pages.
Thesleff et al., "Cell-matrix interactions in tooth development", Int. J. Dev. Bioi., vol. 33, (1989), pp. 91-97.
Tilki et al., "Emerging biology of vascular wall progenitor cells in health and disease", Trends in Molecular Medicine, vol. 15, No. 11, (2009), pp. 501-509.
Trombi et al., "Human Autologous Plasma-Derived Clot as a Biological Scaffold for Mesenchymal Stem Cells in Treatment of Orthopedic Healing," Journal of Orthopaedic Research (Feb. 2009), pp. 176-183.
Trujillo et al., "Adipose Tissue-Derived Factors: Impact on Health and Disease", Endocrine Reviews, vol. 27, No. 7, 2006), pp. 762-778.
U.S. Appl. No. 09/517,981, filed Mar. 3, 2000.
U.S. Appl. No. 15/159,406, filed May 19, 2016.
U.S. Appl. No. 13/828,525, filed Mar. 14, 2013.
U.S. Appl. No. 14/537,253, filed Nov. 10, 2014.
U.S. Appl. No. 14/933,176, filed Nov. 5, 2015.
U.S. Appl. No. 14/942,292, filed Nov. 16, 2015.
U.S. Appl. No. 15/288,539, filed Oct. 7, 2016.
U.S. Appl. No. 60/219,198, filed Jul. 19, 2000.
U.S. Appl. No. 60/288,212, filed May 2, 2001.
U.S. Appl. No. 60/970,721, filed Sep. 7, 2007.
U.S. Appl. No. 61/814,192, filed Apr. 19, 2013.
U.S. Appl. No. 61/864,499, filed Aug. 9, 2013.
U.S. Appl. No. 61/952,128, filed Mar. 12, 2014.
U.S. Appl. No. 62/079,916, filed Nov. 14, 2014.
U.S. Appl. No. 62/079,931, filed Nov. 14, 2014.
U.S. Appl. No. 62/079,939, filed Nov. 14, 2014.
Ulmer et al., "Stem Cells—Prospects in Dentistry", Schweiz Monatsschr Zahnmed, vol. 120, Oct. 2010, pp. 860-872.
Umlauf et al., "Cartilage biology, pathology, and repair", Cell. Mol. Life Sci., vol. 67, (2010), pp. 4197-4211.
Uriel et al., "The role of adipose protein derived hydrogels in adipogenesis", Biomaterials, vol. 29, (2008), pp. 3712-3719.
Van der Donk, "Rinsing Morselized Allografts Improves Bone and Tissue Ingrowth", Clinical Orthopaedics and Related Research, 2003, 408:302-310.
Voskerician et al., "Human Peritoneal Membrane Reduces the Formation of Intra-Abdominal Adhesions in Ventral Hernia Repair: Experimental Study in a Chronic Hernia Rat Model", J. Surg. Res., vol. 157, pp. 108-114, 2011.
Wilson et al., "Adipose-derived stem cells for clinical applications: a review", Cell Proliferation, vol. 44, (2011}, pp. 6-98.
Wilson et al., "Proteomic analysis of cartilage proteins", Methods, vol. 45, (2008), pp. 22-31.
Wu et al., "Muscle-derived stem cells: isolation, characterization, differentiation, and application in cell and gene therapy", Cell Tissue Res., vol. 340, (2010), pp. 549-567.
Xiao et al., "Clonal Characterization of Bone Marrow Derived Stem Cells and Their Application for Bone Regeneration" Int. J. Oral Sci., vol. 2, No. 3, (2010), pp. 127-135.
Xu, et al., "Umbilical Cord-Derived Mesenchymal Stem Cells Isolated by a Novel Explantation Technique Can Differentiate into Functional Endothelial Cells and Promote Revascularization", Stem Cells and Development, vol. 19, No. 10, Oct. 2010, pp. 1511-1523.
Yoder et al., "Redefining endothelial progenitor cells via clonal analysis and hematopoetic stem/progenitor cell principals", Blood, vol. 109, No. 5, Mar. 1, 2007, pp. 1801-1809.
Young et al., "Bone matrix proteins: their function, regulation, and relationship to osteoporosis", Osteoporos Int., vol. 14 (Suppl 3), (2003), pp. S35-S42.
Young et al., "Injectable hydrogel scaffold from decellularized human lipoaspirate", Acta Biomaterialia, vol. 7, (2011}, pp. 1040-1049.
Yun et al.. "Transcriptional Regulatory Networks Associated with Self-Renewal and Differentiation of Neural Stem Cells", Journal of Cellular Physiology, vol. 225, published on line in Wiley Online Library (wileyonlinelibrary.com) Jul. 2010, pp. 337-347.
Zengin et al., Vascular wall resident progenitor cells: a source for postnatal vasculogenesis, Development, vol. 133, No. 8, (2006), pp. 1543-1551.
Zhang et al., "A nerve graft constructed with xenogeneic acellular nerve matrix and autologous adipose-derived mesenchymal stem cells", Biomaterials, vol. 31, (2010), pp. 5312-5324.
Zouboulis et al., "Human skin stem cells and the ageing process", Experimental Gerontology, vol. 43, (2008), pp. 986-997.
Communication Pursuant to Article 94(3) dated Sep. 4, 2020, for corresponding European Patent Application No. 16728155.9.
Mariman et al., "Adipocyte extracellular matrix composition, dynamics and role in obesity", Cell. Mol. Life Sci., vol. 67, 2010), pp. 1277-1292.
Massirer et al., "Maintenance and differentiation of neural stem cells", WIREs Systems Biology and Medicine, vol. 3, Jan./Feb. 2011, pp. 107-114.
Masuda, "Biological repair of the degenerated intervertebral disc by the injection of growth factors", Eur. Spine J., vol. 7 (Suppl. 4), (2008), pp. S441-S451.
Mauney et al., "In vitro and in vivo evaluation of differentially demineralized cancellous bone scaffolds combined with human bone marrow stromal cells for tissue engineering", Biomaterials, 26, 2005, pp. 3173-3185., 13 pages.

(56) References Cited

OTHER PUBLICATIONS

McNally et al., "Plantar Fascia: Imaging Diagnosis and Guided Treatment", Seminars in Musculoskeletal Radiology, vol. 14, No. 3, {2010), pp. 334-343.
Meinel et al., "Bone Tissue Engineering Using Human Mesenchymal Stem Cells: Effects of Scaffold Material and Medium Flow," Annals of Biomedical Engineering, vol. 32, No. 1, {Jan. 2004) pp. 112-122.
Meinel et al., "Engineering bone-like tissue in vitro using human bone marrow stem cells and silk scaffolds," Journal of Biomedical Materials Research; 71A, pp. 25-34, {2004).
Meisel et al.; "Clinical experience in cell-based therapeutics: Disc chondrocyte transplantation A treatment for degenerated or damaged intervertebral disc", Biomolecular Engineering, vol. 24, {2007), pp. 5-21.
Melero-Martin et al., "Concise Review: Vascular Stem Cells and Tumor Angiogeneses", Stem Cells, vol. 29, {2011) pp. 163-168.
Mercuri, et al., "Novel tissue-derived biomimetic scaffold for regenerating the human nucleus pulposus", J. Biomed. Mater. Res. A, vol. 96, No. 2, Feb. 2011, p. 35.
Metcalf, "Stem Cells, Pre-Progenitor Cells and Lineage-Committed Cells: Are Our Dogmas Correct?", Annals New York Academy of Sciences, Feb. 6, 2006, pp. 289.
Miki et al., "Stem Cell Characteristics of Amniotic Epithelial Cells", Stem Cells, vol. 23, {2005), pp. 1549-1559.
Minguell et al., "Mesenchymal Stem Cells", Exp. Bioi. Med., vol. 226, No. 6, {2001), pp. 507-520.
Miyamoto et al., "Intradiscal transplantation of synovial mesenchymal stem cells prevents intervertebral disc degeneration through suppression of matrix metalloproteinase-related genes in nucleus pulposus cells in rabbits", Arthritis Research & Therapy, vol. 12, {2010), pp. 1-13.
Mizuno, "Adipose-derived Stem Cells for Tissue Repair and Regeneration: Ten Years of Research and a Literature Review", Journal of Nippon Medical School, vol. 76, No. 2, {2009), pp. 56-66.
Mulliken et al., "Use of Demineralized Allogeneic Bone Implants for the Correction of Maxillocraniofacial Deformities", Annual Meeting of the American Surgical Association, 194 {3), 1981, pp. 366-372. 7 pages.
Murakami et al., "Quantitative differences in intervertebral discmatrix composition with age-related degeneration", Med. Bioi. Eng. Comput., vol. 48, {2010), pp. 469-474.
Murtuza et al., "Micro- and Nanoscale Control of the Cardiac Stem Cell Niche for Tissue Fabrication", Tissue Engineering: Part B; vol. 15, No. 4, {2009), pp. 443-454.
Nilsen et al., "Cytokine profiles of cultured microvascular endothelial cells from the human intestine", downloaded from gut.bmj.com on Dec. 18, 2012, pp. 635-642.
Rabie et al., The Effect of Demineralized Bone Matrix on the Healing of Intramembranous Bone Grafts in Rabbit Skull Defects, J. Dent. Res, vol. 75, No. 4, {Apr. 1996), pp. 1045-1051.
Non-Final Office Action for U.S. Appl. No. 13/108,856, dated Dec. 31, 2012.
Non-final Office Action for U.S. Appl. No. 13/108,856, dated Feb. 27, 2014.
Non-Final Office Action for U.S. Appl. No. 13/690,542, dated Nov. 24, 2014.
Non-Final Office Action for U.S. Appl. No. 13/828,525, dated Dec. 19, 2014.
Non-final Office Action for U.S. Appl. No. 13/828,525, dated Jan. 7, 2016.
Non-Final Office Action for U.S. Appl. No. 13/828,525, dated Oct. 7, 2016.
Non-Final Office Action for U.S. Appl. No. 13/948,798, dated Nov. 27, 2013.
Non-Final Office Action for U.S. Appl. No. 14/537,253, dated Nov. 25, 2015.
Non-Final Office Action for U.S. Appl. No. 14/933,176, dated Jul. 12, 2016.
Non-Final Office Action for U.S. Appl. No. 14/942,292, dated Nov. 2, 2016.
Office Action for European Patent Application No. 16 728 155, dated Jul. 11, 2019.
Office Action for U.S. Appl. No. 15/159,406, dated Aug. 7, 2017.
Oh et al., a new bone banking technique to maintain osteoblast viability in frozen human iliac cancellous bone; Cryobiology, vol. 44, {2002), pp. 279-287.
OPTP,The Anatomy of Fascia-Revealed! a discovery of 3-D continuity for MFR therapists, Feb. 2006, 2 pages.
Osathanon et al., "Basic fibroblast growth inhibits mineralization but induces neuronal differentiation by human dental pulp stem cells through a FGFR and PLCy signaling pathway", Journal of Cellular Biochemistry, Mar. 4, 2011, pp. 807-1816.
Osteotech, Inc.: Xpanse® R Bone Insert—Introduction, web page printed Jun. 23, 2011, from http://osteotech.com/prodxpanseR.shtm, 1 page.
Pacifici et al., Mechanisms of Synovial Joint and Articular Cartilage Formation: Recent Advances, but Many Lingering Mysteries, Birth Defects Research {Part C), vol. 75, {2005), pp. 237-248 D.
Pacilli,"Vascular wall resident progenitor cells, A review", Experimental Cell Research, vol. 315, {2009) pp. 901-914.
Pantou et al., "The effect of platelet-rich plasma {PRP) combined with a bone allograft on human periodontal ligament POL) cells," Cell Tissue Bank, vol. 13, {2012), pp. 81-88.
Paterson et al.. "Dental tissue engineering products in the U.S. market to double by 2015", Dental Tribune, Dec. 2009,p. 5A.
PCT Patent Application No. PCT/US2016/033246, Modified Demineralized Cortal Bone Fibers, filed May 19, 2016.
Peng et al., "Comparative Analysis of Mesenchymal Stem Cells from Bone Marrow, Cartilage,and Adipose Tissue", StemCells and Development, vol. 17, {2008), pp. 761-774.
Peng et al., "Mesenchymal Stem Cells and Tooth Engineering", Int J Oral Sci, vol. 1, No. 1, {2009), pp. 6-12.
Peroni et al., "Stem molecular signature of adipose-derived stromal cells", Experimental Cell Research, vol. 314, 2008), pp. 603-615.
Piekarz et al., "Phase II Multi-Institutional Trial of the Histone Deacetylase Inhibitor Romidepsin as Monotherapy for Patients with Cutaneous T-Cell Tymphoma", American Society of Clinical Oncology, vol. 27, No. 32, Nov. 10, 2009, pp. 5410-5412.
Pollen et al., "Stem Cells: attributes, cycles, spirals, pitfalls and uncertainties—Lessons for and from the Crypt", Development, vol. 110, {1990), pp. 1001-1020.
Pretzel et al., "Relative percentage and zonal distribution of mesenchymal progenitor cells in human osteoarthritic and normal cartilage", Arthritis Research & Therapy, vol. 13, R64, {2011 ), 37 pages, http://arthritis-research.com/content/13/2/R65.
Puetzer et al., "Comparative Review of Growth Factors for Induction of Three-Dimensional In Vitro Chondrogenesis in Human Mesenchymal Stem Cells Isolated from Bone Marrow and Adipose Tissue", Tissue Engineering: Part B, vol. , No. 4, {2010), pp. 435-444.
Finnin et al., "Structures of a histone deacetylase homologue bound to the TSA and SAHA inhibitors", Nature, vol. 401, Sep. 9, 1999, pp. 188-190.
Flynn et al., "Adipose tissue engineering with cells in engineered matrices", Organogenesis, vol. 4, No. 4, {2008), pp. 228-235.
Flynn, "The use of decellularized adipose tissue to provide an inductive microenvironment for the adipogenic differentiation of human adipose-derived stem cells", Biomaterials, vol. 31, {2010) pp. 4715-4724.
Fong et al., "The Crowning Achievement: Getting to the Root of the Problem", Journal of Dental Education, vol. 69, No. 5, May 2005, pp. 555-570.
Fraser et al., "Fat tissue: an underappreciated source of stem cells for biotechnology", Trends in Biotechnology, vol. 24,No. 4,Apr. 2006,pp. 150-154.
Fuchs et al., "Building Epithelial Tissues from Skin Stem Cells", Cold Spring Harb Symp Quant Bioi., vol. 73, {2008), pp. 333-350.
Gaissmaier et al., "Growth and differentiation factors for cartilage healing and repair", Injury, Int. J. Care Injured, vol. 3951, {2008), pp. 588-596.
Gopinath et al., "Stem Cell Review Series: Aging of the skeletal muscle stem cell niche", Aging Cell, vol. 7, {2008), pp. 590-598.

(56) References Cited

OTHER PUBLICATIONS

Gray's Anatomy of the Human Body, "Tendons, Aponeuroses, and Fasciae", http://education.yahoo.com/reference/gray/subjects/subject/104, printed May 16, 2011, 2 pages.
Gregoire et al., "Understanding Adipocyte Ditferentiation", Physiological Reviews, vol. 78, No. 3, Jul. 1998, pp. 783-809.
Grogan et al., "Mesenchymal progenitor cell markers in human articular cartilage: normal distribution and changes in osteoarthrtis", Arthritis Research & Therapy, vol. 11, No. 3, Jun. 5, 2009, pp. 1-13.
Gronthos et al., "Surface Protein Characterization of Human Adipose Tissue-Derived Stromal Cells", Journal of Cellular Physiology, vol. 189, {2001 }, pp. 54-63.
Guilak et al., "The Pericellular Matrix as a Transducer of Biomechanical and Biochemical Signals in Articular Cartilage", Ann. N.Y. Acad. Sci., vol. 1068, {2006), pp. 498-512.
Guimberteau, et al., "The Microvacuolar System: How Connective Tissue Sliding Works", The Journal of Hand Surgery European Volume), vol. 35E, No. 8, {2010), pp. 614-622.
Halberg et al., "The Adipocyte as an Endocrine Cell", Endocrinol Metab. Clin. North Amer., vol. 37, No. 3, Sep. 2008, pp. 753-767.
Han et al., "The Effect of Thrombin Activation of Platelet-Rich Plasma on Demineralized bone Matrix Osteoinductivity," The Jounral of Bone and Joint Surgery, vol. 91, {2009), pp. 1459-1470.
Hardingham, "Extracellular Matrix and Pathogenic Mechanisms in Osteoarthritis", Current Rheumatology Reports, vol. 10, {2008), pp. 30-36.
Heinegard et al., "The role of the cartilage matrix in osteoarthritis", www.nature.com/nrrheum, Nat. Rev. Rheumatol., vol. 7, Jan. 2011, pp. 50-56.
Heller, "Soft Tissue, Fascia and the Adjustment", http://chiroweb.com/mpacms/dc/article.php?=39&id=18250&no_paginate=true&p_friendly=true&no_b=true, printed Jun. 28, 2011.
Henriksson et al.. "Identification of Cell Proliferation Zones, Progenitor Cells and a Potential Stem Cell Niche in the intervertebral Disc Region", Spine, vol. 34, No. 21, {2009), pp. 2278-2287.
Hidaka et al., "Regulatory Mechanisms of Chondrogenesis and Implications for Understanding Articular Cartilage Homeostasis", Current Rheumatology Reviews, vol. 4, No. 3, {2008), pp. 1-12.
Hiraoka et al., "Mesenchymal progenitor cells in adult human articular cartilage", Biorheology, vol. 43, {2006), pp. 147-454.
Hirschi et al., "Smooth Muscle Stem Cells", The Anatomical Record Part A, vol. 276A, {2004), pp. 22-33.
Hodde et al. "Extracellular Matrix as a Strategy for Treating Chronic Wounds" Am J. Clin Dermatol, vol. 8, No. 2, 2007), pp. 61-66.
Hoell, et al.; "Auto ftuorescence of intervertebral disc tissue: a new diagnostic tool", Eur Spine J, vol. 15 {Suppl. 3), 2006), pp. S345-S353.
Hollander et al., "Stem Cells and Cartilage Development: Complexities of a Simple Tissue", Stem Cells, vol. 28, 2010), pp. 1992-1996.
Honda et al., "Dental follicle stem cells and tissue engineering", Journal of Oral Science, vol. 52, No. 4, {2010), pp. 541-552.
Hsieh et al., "Cellular Mechanobiology of the Intervertebral Disc: New Directions and Approaches", J. Biomech., vol. 43, No. 1, Jan. 5, 2010, 20 pages.
Huang et al., "Mesenchymal Stem Cells Derived from Dental Tissues vs. Those from other Sources: Their Biology and Role in Regenerative Medicine", J. Dent. Res., vol. 88, No. 9, Sep. 2009, pp. 792-806.

Huntsman et al., "Lumbar Interbody Fusion With Osteosponge® Demineralized Allograft in a PEEK Cage as Compared to Fusion with rhBMP-2: 1 Year Post Operative Assessment," dated Feb. 2009, from Bacterin International, Inc. website: www.bacterin.com, 4 pages.
Ingram et al., "Vessel wall-derived endothelial cells rapidly proliferate because they contain a complete hierarchy of endothelial progenitor cells", Blood, vol. 105, No. 7, Apr. 11, 2005, pp. 2783-2786.
International Search Report and Written Opinion for PCT/US2016/033246, dated Sep. 5, 2016.
Isolation of Stromal Stem Cells from Human Adipose Tissue, http://www.collaslab.com/UserFiles/File/Adipose%20stem%20cell%20isolation.pdf; article not dated, printed Jul. 20, 2011.
Jin et al., Human Amniotic Membrane as a Delivery Matrix for Articular Cartilage Repair, Tissue Engineering, vol. 13, No. 4,2007, pp. 693-702.
Jones et al.. "No place like home: anatomy and function of the stem cell niche", Nature Reviews/Molecular Cell Biology, vol. 9, Jan. 2008, pp. 11-13.
Kajstura et al., "Evidence for Human Lung Stem Cells", The New England Journal of Medicine, vol. 364, No. 19, May 12, 2011,pp. 1795-1806.
Karlsson et al., "Articular cartilage stem cell signalling", Arthritis Research & Therapy, vol. 11, No. 4, Jul. 24, 2009, pp. 1-2.
Kilroy et al., "Cytokine Profile of Human Adiopose-Derived Stem Cells: Expression of Angiogenic, Hematopoietic, and Pro-Inflammatory Factors", Journal of Cellular Physiology, vol. 212, {2007), pp. 702-709.
Koga et al., "Comparison of mesenchymal tissues-derived stem cells for in vivo chondrogenesis: suitable conditions fo cell therapy of cartilage defects in rabbit", Cell Tissue Res., vol. 333, {2008), pp. 207-215.
Kondo, et al. "Intervertebral Disc Development is Regulated by Wnt!JI-catenin Signaling", Spine, vol. 36, No. 8, 2011 ), pp. E513-E518.
Kuhbier et al., "Stem cells from fatty tissue. A new resource for regenerative medicine?", Chirug, vol. 81, {2010), pp. 826-832.
Kurth et al., "Functional Mesenchymal Stem Cell Niches in Adult Mouse Knee Joint Synovium In Vivo", Arthritis & Rheumatism, vol. 63, No. 5, May 2011, pp. 1289-1300.
LaBarge et al., "Of Microenvironments and Mammary Stem Cells", Stem Cell Reviews, vol. 3, No. 2, {2007) pp. 137-146.
Lahm et al., "Unraveling the hidden catalytic activity of vertebrate class IIa histone deacetylases", PNAS, vol. 104, No. 14, Oct. 30, 2007, pp. 17335-17340.
Lee, et al., "Mesenchymal Progenitor Cells Derived from Synovium and Infrapatellar Fat Pad as a Source for Superficial Zone Cartilage Tissue Engineering: Analysis of Superficial Zone Protein/Lubricin Expression", Tissue Engineering: Part A, vol. 16, No. 1, {2010), pp. 317-325.
Li et al., "Human treated dentin matrix as a natural scaffold for complete human dentin tissue regeneration", Biomaterials {2011), pp. 1-14.
Lin et al., "The Chondrocyte: Biology and Clinical Application", Tissue Engineering, vol. 12, No. 7, {2006), pp. 1971-1984.
Lozito et al., "Mesenchymal Stem Cell Modification of Endothelial Matrix Regulates Their Vascular Differentiation", Journal of Cellular Biochemistry, vol. 107, {2009), pp. 706-713.
Lyngstadaas et al., "Enamel matrix proteins; old molecules for new applications", Orthod Craniofac Res., vol. 12, No. 3, Aug. 2009, pp. 243-253.
Lynn, et al., "Antigenicity and Immunogenicity of Collagen", published online Jul. 16, 2004 in Wiley InterScience {www.Interscience.wiley.com), pp. 343-354.

MODIFIED DEMINERALIZED CORTICAL BONE FIBERS

CROSS-REFERENCE TO RELATED APPLICATIONS

This application is a divisional of U.S. patent application Ser. No. 15/159,406 filed on May 19, 2016, now allowed and which claims the benefit of U.S. Provisional Application No. 62/331,071, filed May 3, 2016, and U.S. Provisional Application No. 62/164,827, filed May 21, 2015, the entire disclosures of all of which are incorporated by reference herein. This application also relates to commonly owned International Application No. PCT/US16/33246, filed May 19, 2016 and entitled "Modified Demineralized Cortical Bone Fibers," the entire disclosure of which is incorporated by reference herein.

FIELD OF THE INVENTION

The disclosed invention relates to the field of surgical grafts for the repair of bone defects, more particularly, surgical grafts that include demineralized bone particles.

BACKGROUND OF THE INVENTION

Cohesive masses of demineralized cortical bone fibers have been used as bone void fillers or implants for use in general orthopaedic applications, trauma applications, and spinal applications, as well as for repair of craniomaxial defects, dental defects, and other bony defects. Such bone void fillers and implants absorb liquids, such as saline, blood, or bone marrow aspirate, but are slow to wet upon initial contact with a liquid. Further, the hydrated mass of fibers in such implants tends to lack structural strength such that it breaks apart when manipulated or irrigated.

SUMMARY OF THE INVENTION

Demineralized cortical bone fibers may be modified to improve certain properties of cohesive masses of such fibers that affect their usefulness as surgical grafts for bone repair. Such properties include wettability (i.e., surface tension or hydrophilicity), structural stability after compression, reduced swelling upon hydration, resistance to wash-out of fibers during irrigation, and ease of molding the fiber masses in their hydrated form. In a process according to an embodiment of the present invention, the wettability of the demineralized cortical bone fibers is increased by treating them with a biocompatible polar molecule. In an embodiment, the polar molecule comprises one or more of an alcohol, a polyol (e.g., a glycol or a glycerol), a sugar, a ketone, an aldehyde, an organic acid, or another biocompatible polar organic compound. In a process according to an embodiment of the present invention, the wettability of the demineralized cortical bone fibers is increased by treating them with a salt solution, such as saline solution or phosphate buffer. In a process according to an embodiment of the present invention, the wettability of the demineralized cortical bone fibers and/or masses of cortical bone fibers are modified by exposing them to an energetic source such as ultraviolet (UV) radiation. Embodiments of the present invention also include demineralized cortical bone fibers prepared by the aforementioned processes, masses of such demineralized cortical bone fibers, and surgical grafts and implants that include such demineralized cortical bone fibers.

Other embodiments of the present invention include chemical cross-linking of the demineralized cortical bone fibers. Still other embodiments include modifying the surface tension of the fibers by increasing their surface roughness or by drying at least one surface of the implant in contact with an appropriate solid or mesh material.

In embodiments of the present invention, any of the aforesaid methods may be used to treat other forms of demineralized bone matrix, such as demineralized cancellous bone pieces, demineralized cortical bone pieces, or fragments of demineralized bone. The aforesaid methods may also be used to increase the wettability of fibers or other graft materials that include tissue types derived from suitable organs or other tissue sources, or the wettability and/or mechanical properties of masses of such tissue particles.

Embodiments of the present invention include UV containment chambers which enable optimal exposure of the implant to UV radiation, while protecting an operator from exposure to potentially harmful UV radiation. Such containment chambers are specially designed for specific embodiments of the energetic cross-linking process.

BRIEF DESCRIPTION OF THE FIGURES

For a more complete understanding of the present invention, reference is made to the following detailed description of exemplary embodiments considered in conjunction with the accompanying figures, in which.

DETAILED DESCRIPTION OF THE INVENTION

Figure 1:
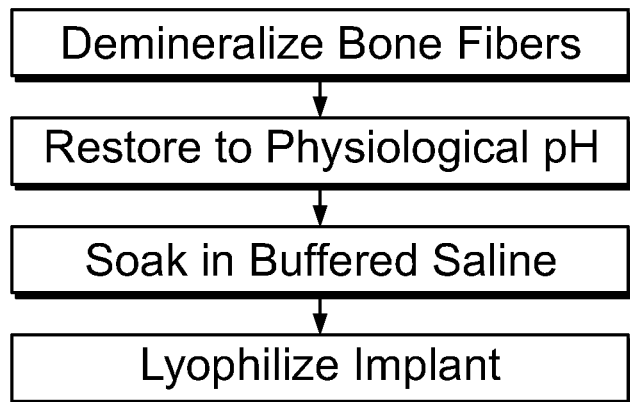
FIG. 1 is a block diagram of a process for modifying demineralized bone particles by a chemical treatment according to an embodiment of the present invention.

Embodiments of the present invention include methods of treating demineralized bone particles to increase the wettability (i.e., surface tension or hydrophilicity) of the particles and modify the wettability and structural properties of implants including such particles. Although the exemplary embodiments presented herein describe the treatment of demineralized cortical bone fibers, the methods may be extended to the treatment of other demineralized bone matrix particles, such as demineralized cortical bone pieces, demineralized cancellous bone pieces, or corticocancellous bone pieces. The methods discussed herein may also be used to treat particles and implants derived from other tissue types. It is noted that the demineralized bone matrix particles and/or other tissue types may be used to make autografts, allografts or xenografts. All such options are within the contemplation of the methods and articles described hereinafter.

I. Demineralized Bone Matrix Particles and Implants Comprising Such Particles "Demineralized bone matrix" (DBM) refers to a bone-derived material that has osteoconductive and osteoinductive activity. DBM may be prepared by acid extraction of allograft bone, resulting in loss of most of the mineralized component but retention of collagen and noncollagenous proteins, including growth factors. Calcium can also be extracted from bone using such compounds as guanidine, ethylenediaminetetraacetatic acid (EDTA), urea, or other compounds that can form soluble complexes with calcium. DBM can be prepared in batch processes (e.g., in a flask, beaker, or other container), by a static or agitated soak, or in a flow-through apparatus whereby the bone is maintained in the apparatus while the demineralizing solution flows through. In agitated soaks, the bone is agitated in the demineralizing solution using methods that employ shaking, stirring, vibration, or ultrasonic techniques. Methods for preparing demineralized bone matrix from bone are known in the art, as disclosed, for example, in U.S. Pat. Nos. 5,073,373; 5,484,601; and 5,284,655, which are incorporated by reference herein. DBM may be prepared from autologous bone, allogeneic (or "allograft") bone, or xenogeneic bone. DBM may be prepared from cancellous bone, cortical bone, corticocancellous bone, or combinations of cancellous, cortical and corticocancellous bone.

"Demineralized cortical bone fibers" ("DCBF") refers to elongated particles of DBM derived from cortical bone, which have a length that is at least twice as great as the thickness and width of the fiber. Elongated particles of other tissue types discussed in this disclosure are also "fibers" for the purpose of this disclosure when they have respective lengths that are at least twice as great as their respective thicknesses and widths.

DCBF, according to embodiments of the present invention, may be derived from the cortical component of the long bones of the femur, tibia, humerus, radius, ulna, and fibula, or other suitable long bones of a mammal. Suitable mammal sources for DCBF include, without limitation, human, bovine, ovine, caprine, and porcine sources. The cortical bone is first stripped of all soft tissue elements and then cleaned using detergents/surfactants to remove residual blood and lipids from the bone surface. The cleaned cortical bone is then processed into elongated particles using a milling process that results in fibers that range in size from about 10 µm to about 1000 µm in thickness, about 20 µm to about 20 cm in length and about 5 µm to about 1 cm in width. The cortical fibers are demineralized in dilute acid resulting in a residual calcium content ranging from less than 15% w/w for partially demineralized fibers, less than 8% w/w for demineralized fibers, and less than 1% w/w for substantially or fully demineralized fibers. The calcium content of the fully demineralized fibers may be negligibly small, such that the fibers consist essentially of collagen, non-collagen protein, including glycoproteins, growth factors, and other non-mineral substances found in the original bone, although not necessarily in their original quantities. In other embodiments of the present invention, blocks of cortical bone are demineralized, and the fibers are subsequently produced by crushing or shredding the demineralized blocks.

The demineralization process is carefully controlled via the concentration of acid and duration of soak time in order to enhance the mechanical properties of the fibers while retaining the osteoinductive components that are exposed by the dilute acid reagents. Following demineralization, the tissue goes through a pH restoration process where the residual acid is neutralized by buffering reagents thereby returning the tissue to near physiological pH of between 6-8 pH. Subsequently, the demineralized cortical bone fibers may be stored in a wet state or dried using lyophilization or other drying techniques. The DCBF may be stored at various temperatures including but not limited to ambient room temperature (e.g., at about 23° C.), refrigerated (e.g., at about 4° C.), frozen (e.g., at about −20° C.), or cryogenically preserved (e.g., at about −196° C.) using controlled rate or uncontrolled rate freezing.

The DCBF may be placed into an implant forming container, such as a jar or a mold, and formed into a variety of shapes including, but not limited to, thin sheets, cubes, discs and strips. More intricate geometries may also be formed including, but not limited to, curves, cutouts, compartments and patterning which can be determined by the shape of the implant forming container. DCBF stored in a wet state may be placed, for example, into molds directly, whereas dried DCBF will need to be rehydrated prior to being placed in molds. For example, when dried DCBF are used they are first disbursed into a liquid carrier to form a solution and then agitated to ensure even distribution of the DCBF in the solution in the mold. As also discussed hereinbelow, the liquid carrier used to form the solution may be, for example without limitation, water, aqueous saline solution, Sorensen's buffer, or phosphate buffered saline solution. In some embodiments, excess liquid from the wet or rehydrated tissue may be separated from the DCBF, drained and removed from the mold. In some embodiments, additional liquids (e.g. water, buffer, or saline) may be added to the tissue before and during the molding process. The liquids added to tissue before and during the molding process could optionally contain therapeutic factors, cytokines, growth factors, pharmaceuticals, antibiotics, free-radical scavengers, sugars, vitamins including, but not limited to, riboflavin and ascorbic acid, surfactants, DMEM medium, human or animal serum, or other additives. The addition or removal of liquid from the tissue also allows the density of the final implant to be controlled and production of an implant of uniform density. The mold may be composed of a single or multiple types of materials, including but not limited to metals, glass, plastics, silicone, Teflon®, and ceramics. In an embodiment, the vessel or package in which the demineralized cortical bone fibers are stored serves as the mold.

In an embodiment, the mold is micro-porous or meshed with pore sizes ranging up to 5 mm. In an embodiment, the mold includes a non-uniform material. In an embodiment, the mold has varying pore sizes or mesh sizes, with the pores or meshes having different sizes at different locations in the mold. In an embodiment, the mold may include a layer of material placed on the top of the DCBF, the layer being of the same material used elsewhere in the mold or of a different material. In embodiments, the layer is solid, porous, or meshed, or has another geometry appropriate to the intended use of the mold and implant to be produced therefrom.

In an embodiment, DCBF are in the form of a mass of DCBF, which are then used to prepare implants that may be used as bone void filler or bone graft extender in bony voids and gaps which have been surgically created or caused by traumatic injury to the bone. Implants and grafts, as used herein, refer to tissues, organs or components thereof that are transplanted from a donor to a recipient and include those transplanted between individuals of the same species ("allograft"), those donated and transplanted into the same individual ("autograft"), and those transplanted between individuals of different species ("xenograft"). Such implants may be used as a standalone treatment device or be applied in combination with one or more of a variety of bioactive osteogenic materials or cells that facilitate the reconstruction and healing of bone. Such implants may include particles of cortical, cancellous, or corticocancellous bone. Such particles may be partially demineralized, demineralized, fully demineralized, or may have most or all of their original mineral or calcium content.

In an embodiment, the DCBF are pre-hydrated in an aqueous buffer, or combined with a carrier, such as, but not necessarily limited to, the following: an isotonic solution; a sodium chloride solution at a concentration of about 0.1% to about 1%, more particularly, about 0.9%; a lactated Ringer's solution, with or without DSLR; phosphate buffered saline ("PBS"); platelet rich plasma (PRP); glycerin; lecithin; alginate; hyaluronic acid (HA); a derivative of HA; or sodium hyaluronate; or other suitable carriers known in the art. The term "carrier" as used herein refers to a pharmaceutically acceptable inert agent or vehicle for delivering one or more active agents to a subject, and often is referred to as "excipient." The carrier must be of sufficiently high purity and of sufficiently low toxicity to render it suitable for administration to the subject being treated. The carrier may also comprise "biological components" added to the carrier, such as, but not limited to, DNA, RNA, short hairpin RNA (shRNA), small interfering RNA (siRNA), micro RNA (mRNA), polysaccharides, peptides, matrix proteins, glycosaminoglycans (e.g, hyaluronic acid), viral vectors, and liposomes. The carrier further should maintain the stability and bioavailability of an active agent added to the carrier.

In an embodiment, a mass of DCBF fibers (e.g., an implant) are provided to a surgeon, who can then add one or more of a carrier, bone marrow, blood, non-demineralized bone chips, etc., and then mold or reshape the mass into a preferred configuration according to anatomical or surgical needs in the operating room. The final form should be cohesive, moldable, and provide some resistance to irrigation when in the defect site, and leave minimal residue on the gloves of those handling it. When the mass is thus prepared, the surgeon can place it in a bone defect site, a site with two adjacent bone defects, or any non-bony defect where it is desired to form new bone or repair bone.

II. Chemical and Surface Treatment of Demineralized Cortical Bone Fibers

Figure 5:
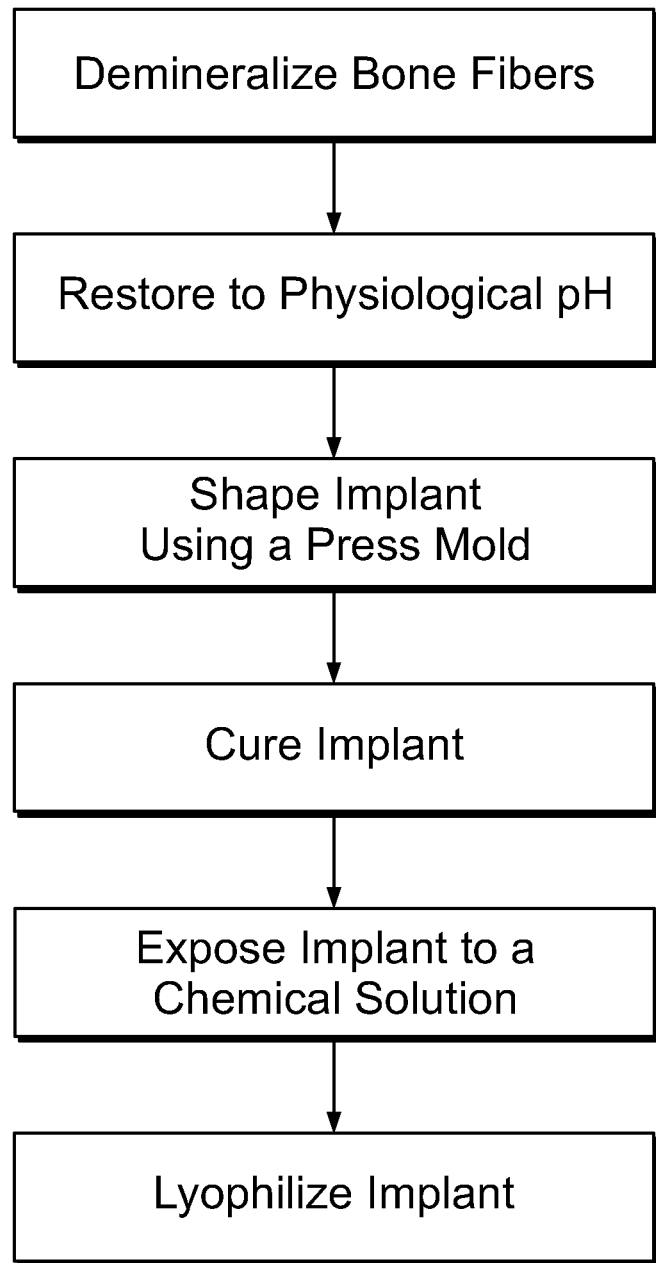
FIG. 5 is a block diagram of a process for modifying demineralized bone particles by a chemical treatment and a curing step according to another embodiment of the present invention.

In an embodiment of the present invention, DCBF are prepared as described in Section I, above, and subjected to treatment with one or more chemical solutions to improve the wettability of the individual fibers and of the fibrous mass. The increased wettability can be obtained by changing the surface charge of the DCBF or changing the surface morphology and/or micro-geometry of the DCBF. The fibers or fibrous mass may be treated with such chemical solutions immediately before the pH restoration step, after the pH restoration step, or before the fibers or fibrous mass are dried. In an embodiment, the fibers or fibrous mass may be dried, then rehydrated prior to treatment with the chemical solution. Furthermore, the DCBF may be treated with such chemical solutions after formation of the implant and before any final drying or lyophilizing step, where applicable. Simplified flow charts of representative chemical treatment processes are shown in FIGS. 1 and 5.

The chemical treatment is performed by contacting the DCBF with one or more chemical solutions selected to improve the wettability of dried or lyophilized DCBF. In an embodiment, the DCBF are soaked in the chemical solution for a period of time from about 6 hours to about 48 hours, for example from about 12 hours to about 36 hours, for example from about 20 hours to about 28 hours. In an embodiment, the soak is a static soak. In an embodiment, the DCBF are agitated during the soak.

In an embodiment, the chemical solution is isotonic with blood. In an embodiment, the chemical solution includes a dissolved salt. In an embodiment, the chemical solution is a physiologically-balanced solution that includes a salt. In an embodiment, the chemical solution is a saline solution. In an embodiment, the solute in the chemical solution consists of sodium chloride (e.g., a 1M NaCl solution). In an embodiment, the chemical solution is Ringer's solution. In an embodiment, the chemical solution is a buffer solution containing a buffering salt. In an embodiment, the chemical solution includes a phosphate salt. In an embodiment, the buffer solution is a standard buffering solution containing a buffering salt. In an embodiment, the buffer solution is a standard phosphate buffered solution (e.g., PBS). In an embodiment, the chemical solution is Sorenson's Buffer. In an embodiment, the chemical solution is Hanks Buffered Salt Solution. In an embodiment, the chemical solution is a HEPES-buffered solution.

In an embodiment, the chemical solution includes a biologically-compatible polar organic compound. In an embodiment, the chemical solution includes an alcohol. In an embodiment, the chemical solution includes ethanol. In an embodiment, the chemical solution includes a polyol. In an embodiment, the chemical solution includes a glycol. In an embodiment, the chemical solution includes glycerol. In an embodiment, the chemical solution includes polyethylene glycol. In an embodiment, the chemical solution includes a sugar. In an embodiment, the chemical solution includes dextrose. In an embodiment, the chemical solution includes mannitol-D. In an embodiment, the chemical solution includes sodium ascorbate. In an embodiment, the chemical solution includes one or more of a ketone, an aldehyde, an organic acid, or another biocompatible polar organic compound. In an embodiment, the chemical solution includes an additive to inhibit proteolytic activity of proteinases (e.g., matrix metalloproteinases, "MMP"). In an embodiment, the additive is chlorhexidine gluconate. In an embodiment, the additive is galardin. In an embodiment, the chemical solution includes a combination of one or more biologically-compatible polar organic compounds and one or more dissolved salts. In an embodiment, the chemical solution is a non-aqueous solution. In an embodiment, a polar organic liquid is used in place of the chemical solution.

In an embodiment, the chemical solution includes a biologically-compatible polar organic compound and/or a dissolved salt, and an additive. In an embodiment, the additive is a therapeutic agent for administration to a mammal. In an embodiment, the additive is a cytokine. In an embodiment, the additive is a pharmaceutical. In an embodiment, the additive is an antibiotic. In an embodiment, the additive is a nutrient. In an embodiment, the additive is a trace element. In an embodiment, the additive is a free-radical scavenger. In an embodiment, the additive is a growth factor. In an embodiment, the additive is a biologically-active compound.

In an embodiment, the ratio of DCBF to the chemical solution is in a range of about 1:10 g/ml to about 1:1 g/ml. In an embodiment, the ratio of the DCBF to the chemical solution are selected to provide a desired fiber density and fractional void volume in the dried implant. In such an embodiment, lower ratios of DCBF to chemical solution result in less dense implants with higher void volumes.

In some embodiments, the implants produced by the methods described and contemplated herein have uniform density. An implant may be tested for uniform density by various methods. One suitable method, for example without limitation, for determining whether an implant has uniform density is to measure the overall density of the implant, then divide or cut the implant into at least three portions and measure the density of each portion, to produce at least four measured density values for that single implant. The average density for that implant is calculated by dividing the sum of all densities (whole implant and all pieces) by the total number of pieces plus 1 (for the whole implant density). Next, the percent relative standard deviation (% RSD) for that implant is determined as a percentage by first determining the standard deviation of all the measured density values using conventional statistical analysis methods, and then dividing that standard deviation by the average density and multiplying by 100. As the term "uniform density" is used herein, an implant is considered to have uniform density when the % RSD is less than about 30%, such as less than about 25%, or less than about 20%, or less than about 15%, or less than 10%. Example 26 provides an example of such calculations.

Following treatment with the chemical solution, the treated DCBF are dried. In an embodiment, the treated DCBF are dried by air drying. In an embodiment, the treated DCBF are dried by vacuum filtration. In an embodiment, the treated DCBF are dried by heat-drying. In an embodiment, the treated DCBF are dried by solvent-drying. In an embodiment, the treated DCBF have a residual moisture content of less than 80% after drying. In an embodiment, the treated DCBF have a residual moisture content in a range of about 60% to about 80% after drying.

In an embodiment, the treated DCBF are dried by lyophilization. In an embodiment, the treated DCBF are frozen before being lyophilized. In an embodiment, the treated DCBF are refrigerated before being lyophilized. In an embodiment, the treated DCBF are staged at room temperature before being lyophilized. In an embodiment, the treated DCBF are dried to a residual moisture content of less than 80% before being lyophilized. In an embodiment, a quantity of a chemical solution is added to the dried DCBF, and the solvent is removed from the DCBF fibers by lyophilization. In an embodiment, the ratio of treated DCBF to chemical solution is in a range of about 1:0.8 (g/ml) to about 1:10 (g/ml) before lyophilization. In an embodiment, the treated DCBF have a residual moisture content of less than 6% after lyophilization.

In an embodiment, wet-treated DCBF (i.e., DCBF treated with a chemical solution) are placed in an implant forming container, such as a mold, prior to lyophilization, such that the lyophilized DCBF mass takes the shape of the mold. In an embodiment, wet treated DCBF are placed in a jar or other container, then lyophilized. The final tissue form, or implant comprising treated dried DCBF, may then be provided to medical personnel for use as discussed in Section I, above.

As shown FIG. 5, in another embodiment, following treatment with a chemical solution and prior to drying or lyophilizing, the treated DCBF may be subjected to a curing step which involves warming the treated DCBF for a period of time. For example, curing may be accomplished, without limitation, by warming the treated DCBF using ambient air, warm air, radiant heat, or energy such as UV light or microwaves. In such an embodiment, the treated DCBF may be warmed to a temperature of from about 20° C. to about 50° C., such as from about 25° C. to about 45° C., or from about 30° C. to about 45° C., or from about 35° C. to about 45° C. In such an embodiment, the treated DCBF may be warmed for a period of time of from about 30 minutes to about 24 hours, such as from about 4 hours to about 20 hours, or from about 4 hours to about 16 hours, or from about 6 hours to about 12 hours. Without intending to be limited by theory, it is believed that performing a warming step as described above produces an implant comprising treated DCBF that retains its shape after rehydration prior to use.

In an embodiment of the present invention, lyophilized DCBF treated using the methods described above are rehydrated prior to use. In an embodiment, lyophilized DCBR treated according to the methods described above are rehydrated prior to being packaged. In embodiments of such rehydration, the lyophilized DCBF are mixed with PBS, with or without other of the substances described above with respect to chemical solutions. In an embodiment, ratio of DCBF/PBS is selected to generate a cohesive, moldable composition that includes completely hydrated DCBF. In an embodiment, the mixture is in a range of about 20:80 DCBF/PBS (g/ml) to about 34/66 DCBF/PBS (g/ml).

In an embodiment of the present invention, the surface roughness of the DCBF is modified using a surface modification technique known in the art or to be discovered. Known suitable techniques include, without limitation, overcoating, surface gradient modification, surface-active bulk additives, surface chemical reactions, etching, roughening, conversion coatings, ion beam implantation, Langmuir-Blodgett deposition, laser roughening, parylene coatings, photografting, radiation grafting, radiofrequency glow discharge plasma deposition, radiofrequency glow discharge treatment, self-assembled monolayers, silanization, surface-modifying additives, and other means of modifying surfaces of fibers. In an embodiment, one or more of the aforesaid techniques creates surface features on the micron scale, sub-micron scale, nano-scale, or other scales.

In an embodiment of the present invention, the wettability of an implant comprising modified or non-modified DCBF can be measured using standard methods for assessing surface tension, including but not limited to static and dynamic contact angle measurement techniques. Suitable contact angle measurement techniques include, but are not limited to, optical tensiometry, force tensiometry, Wilhelmy plate methods, sessile drop methods, captive air bubble methods, capillary air methods, the du Nouy ring method, or other measurement techniques for determining contact angles of liquid substances. In certain embodiments, DCBF implants prepared according to methods of the present invention may have at least one surface where the contact angle is less than 90 degrees, or less than 60 degrees, or less than 45 degrees. Another suitable method for measuring the wettability of an implant is, for example without limitation, by observing the rate at which a DCBF implant absorbs an amount of liquid. In an embodiment, the amount of liquid is a measured volume deposited on a surface of the implant and the measured value is known as wettability time. Implants produced according to the methods described and contemplated herein have a wettability time of less than about 5 minutes, such as less than about 4 minutes, or less than about 3 minutes, or less than about 2 minutes, or less than about 1 minute. Still another suitable method for measuring the wettability of an implant is, for example without limitation, submerging the implant in an excess amount of liquid and measuring the time required for the implant to absorb enough of the liquid to completely submerge the implant and the measured value is known as complete rehydration time. Implants produced according to the methods described and contemplated herein have a complete rehydration time of less than about 30 minutes, such as less than about 20 minutes, or less than about 15 minutes, or less than about 10 minutes, or less than about 5 minutes.

III. Energetic, Physical, and Chemical Cross-Linking of Demineralized Cortical Bone Fibers In an embodiment, the present invention includes an implant that is comprised of DCBF that have been either fully or partially cross-linked using energetic sources. Suitable energetic sources include ultraviolet (UV) radiation, ozone, plasma, (e.g., RF plasma), coronal discharge, or other means that provide the energy needed to form cross-links between proteins. Suitable plasma media include, but are not limited to, air plasma, oxygen plasma, and ammonium plasma. In an embodiment, energetic cross-linking binds proteins such as albumin or other blood adsorption proteins to the DCBF, otherwise affects the adsorption of the proteins to the DCBF, before lyophilization to increase the wettability of the DCBF implant. The wettability of the energetically cross-linked DCBF implants is measured using the same techniques described in Section II with regard to the chemical and surface treatment of DCBF.

Figure 2:
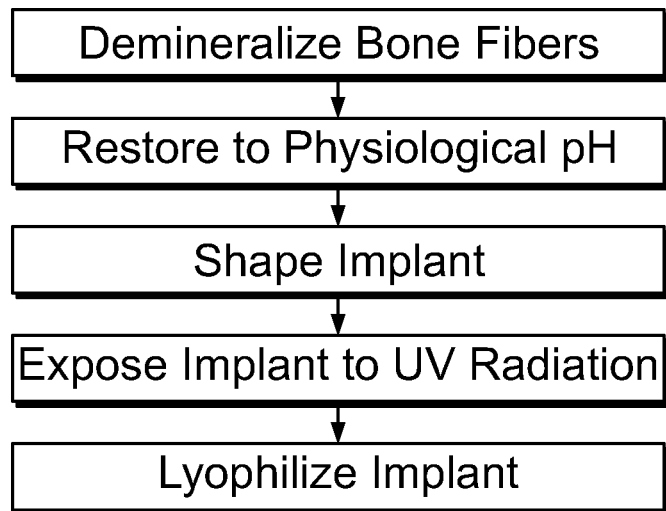
FIG. 2 is a block diagram of a process for modifying demineralized bone particles by exposure to ultraviolet radiation according to an embodiment of the present invention.

Cross-linking imparts a variety of unique properties to the DCBF implant that a non-cross-linked implant would otherwise not possess. Such properties include increased wettability, shape retention under compression, and resistance to fiber washout. A simplified flow chart of a representative energetic cross-linking treatment process is shown in FIG. 2.

In an embodiment of the present invention, DCBF are cross-linked by exposing a mass of DCBF to UV radiation. In an embodiment, wet DCBF are placed into a mold and formed into one of a variety of possibly desirable shapes. Such shapes include, but are not limited to, thin sheets, cubes, discs and strips. More intricate geometries may also be formed including, but not limited to, curves, cutouts, compartments and patterned shapes. In an embodiment, the mass is shaped to approximate a surface of an intact or damaged bone, such as to line a hip socket or the interior of a bone void.

In embodiments of the present invention, suitable molds may be composed of single or multiple types of material or combinations of materials. Such materials include, but are not limited to metals, glasses, plastics and ceramics. Suitable materials may either block UV radiation completely, partially transmit, or fully transmit UV radiation, allowing all or selected portions of the implant to be exposed to UV radiation. While most materials exhibit poor transmission of UV radiation, certain materials such as fused quartz or silica glass and plastics including, but not limited to, optical grade polystyrene and specialized PMMA acrylic (Plexiglas G-UVT, Solarcryl SUVT, Acrylite OP-4) allow for near full transmission of certain wavelengths of UV radiation. After molding the sample into its final shape, the implant may be left in the mold or removed from the mold before undergoing UV cross-linking. The implant may be lyophilized within or without the mold before undergoing UV cross-linking, or lyophilized and rehydrated again prior to UV cross-linking. The implant may also be further masked using materials that completely block or are partially transmissible to UV radiation to further control cross-linking in certain regions of the implant.

In embodiments of the present invention, the mold is a composite of various materials selected to provide variations in the degree of cross-linking across the implant. In an exemplary embodiment, the implant is formed with a cavity to receive an osteoinductive substances or other therapeutic material. In such an embodiment, it may be desirable that the bottom of the implant, opposite the cavity, may be more densely cross-linked to provide increased structural stability to the implant. In other embodiments, variations in cross-linking density may be used to allow certain sections of the implant to be remodeled at different rates than other sections during the bone remodeling process.

In an embodiment of the present invention, UV surface cross-linking is performed by placing the implant in a UV containment chamber and exposing the implant to UV radiation. The UV radiation alters the collagen molecules within the implant, resulting in additional bonds being formed between adjacent collagen molecules. This process of photopolymerization of collagen is believed to occur due to the generation of free radicals via photooxidation of sensitive amino acid residues by UV radiation. The free radicals generated allow the formation of covalent cross-links between the collagen polypeptides, resulting in stronger and stiffer collagen fibers. Aromatic amino acid residues are the predominant sites of free radical formation. Other amino acid residues may be the site of free radical generation under more energetic conditions. Further, the rate at which cross-linkages are formed may be increased by adding biologically-compatible free radical initiators to the DCBF mass. Riboflavin is an example of such an initiator. Other initiators may include other compounds with aromatic structures, or may include sugars.

The amount of liquid in the implant affects the rate and degree of cross-linking. Without being bound by theory, it is believed that the presence of liquid provides a medium for transport of free radicals between collagen fibers. While it is possible to cross-link dried or lyophilized fibers, the embodiments of cross-linking methods according to the present invention are most effective when used with rehydrated fibers. However, excess water may be added to the DCBF implant before cross-linking to swell the implant, thus increasing its porosity, and the exposure time increased, if necessary to achieve the desired amount of cross-linkage.

The rate and depth at which cross-linkages are formed may be controlled by altering the power of the UV radiation source, changing the distance of the implant from the UV radiation source, shifting the wavelength of the UV radiation, varying the exposure time, and by fully or partially blocking UV radiation transmission to certain areas of the implant. Multiple UV radiation sources may be used with a combined power rating ranging from a few watts to a few kilowatts. In high power or energy dense cross-linking implementations of the present invention, the UV containment chamber and implant may be cooled to temperatures ranging from physiological (e.g., about 37° C.) to freezing (e.g., about −80° C.) during the cross-linking process using any of a variety of cooling techniques to prevent heat-related degradation of the implant. Suitable cooling techniques include but are not limited to refrigerant-based cooling, active air cooling, thermoelectric devices, evaporative cooling, and phase-change cooling (e.g., the use of dry ice). The implant may also be placed under UV radiation for multiple short exposures instead of a single long exposure to reduce the amount of heat generated in the tissue. In some embodiments that involve UV cross-linking, it may be beneficial to heat the implant to a temperature that is higher than physiological temperatures (e.g., the implant may be heated to a temperature in a range of from about 37° C. to about 70° C.). Heat may be applied to the implant by the UV bulbs or an additional heating element. The implant may be placed on a heating platform and/or heated by UV bulbs placed around the implant. The addition of heat greater than about 37° C. but less than about 70° C. for lengths of time of from about 10 minutes to about 24 hours increases the cohesiveness of the implant and helps prevent dispersion of the implant when rehydrated or submerged in a rehydrating liquid (e.g., water, saline, blood). In some embodiments, the use of heat to improve the cohesiveness of the implant may be used without the addition of UV exposure.

In embodiments of a method according to the present invention, the intensity or irradiance of the UV radiation at the surface of the implant may be varied by the power of the radiation source and/or the distance between the implant and the UV radiation source. Suitable energy densities for use in a method according to an embodiment of the present invention range from about 100 $\mu W/cm^2$ to about 5,000 $mW/cm^2$ at the surface of the implant. The wavelength of the UV radiation can be shifted between various regions of the UV spectrum including but not limited to longwave UVA (e.g., about 400 to about 315 nm), midrange UVB (e.g., about 315 to about 280 nm), and shortwave UVC (e.g., about 280 to about 100 nm). Shifting the wavelength changes the penetration properties of UV radiation into the implant, with longer wavelengths allowing increased UV penetration and greater depth of cross-linking. For example, in an embodiment of the present invention, exposure to UVA radiation is used to create cross-linking to a depth of about 1 mm, which creates a stiff shell at the surface of the implant. Shifting wavelengths also changes the character of the cross-links, which affects the degree to which properties such as mechanical strength, shape memory retention, and hydrophobicity are modified. Concurrent exposure to UV radiation at differing wavelengths may be used to vary the changes in properties across the implant. Wavelengths in the UVC spectrum also have the added benefit of being germicidal, and thus can be used to sterilize the surfaces of the implant while it undergoes cross-linking.

The length of time that the implant is exposed to the UV radiation source also affects the degree and effectiveness of cross-link formation. In cross-linking methods according to embodiments of the present invention, suitable exposure times are in a range of a few seconds to a few hours depending on the desired properties of the implant. In some embodiments, exposure times of up to 720 minutes may be used, although typical exposure times of about 10 minutes or less may be used (e.g., for commercial production of implants). In some embodiments, even shorter exposure times (e.g., exposure times of about 10 seconds to about 300 seconds) may be used where only a small degree of cross-linking is desired, or where the UV radiation is particularly intense. For many embodiments, the practical exposure times would be in a range of about 10 minutes to about 60 minutes.

After the cross-linking process is completed, the implant may be stored in a wet state or dried using lyophilization, air drying, or other drying methods. The implant may be stored at various temperatures including but not limited to ambient room temperature (e.g., at about 23° C., or up to about 30° C.), refrigerated (e.g., at about 4° C.), frozen (e.g., at about −20° C.), or at cryogenic temperatures (e.g., at about −196° C.) where frozen or cryogenic freezing is achieved using controlled rate and/or uncontrolled rate freezing. By changing the variables discussed above before and during the cross-linking process, a broad range of implants with varying properties may be produced.

In an embodiment of the present invention, the cross-linking process is performed in a containment chamber that allows optimal UV irradiation while shielding an operator from potentially harmful UV irradiation. During the cross-linking process, the implant may be placed on a flat surface, an uneven surface with ridges and peaks, or elevated on a platform or by other means that would allow UV radiation to reflect onto all sides of the implant, including its underside. The surface or platform that the implant rests on could also be made of multiple types of materials that block UV radiation completely, partially transmit UV radiation, or fully transmit UV radiation. The walls of the UV containment chamber may be lined or coated with a reflective material to allow the radiation to scatter within the UV containment chamber, allowing all surfaces of the implant to be exposed to UV radiation. UV radiation sources may also be mounted on multiple walls of the UV containment chamber to allow for better coverage of the implant during the cross-linking process. The orientation of the implant may also be changed during the UV cross-linking process either manually or automated by the UV containment chamber for a more uniform exposure of all surfaces.

Embodiments of the UV cross-linking method of the present invention include the aforesaid containment chambers, which may be specially designed to meet the needs of specific embodiments of the UV cross-linking method. Containment chambers according to embodiments of the present invention may also be designed for use with energetic sources other than UV radiation sources, such as ozone, plasma, (e.g., RF plasma), coronal discharge, or other means that provide the energy needed to form cross-links between proteins. In an embodiment, the containment chamber includes means for positioning and/or moving the implant. In an embodiment, the containment chamber includes one or more sources of UV radiation.

In an embodiment of the present invention, the distance of an implant from a UV radiation source may be changed during the irradiation process using manually or automatically operated device to provide optimal UV irradiation for different types of implants. In an embodiment, the device includes a manual or automated moving platform upon which the implants rest. Such platforms can move along x-, y-, and z-axes. In an embodiment, the device includes single or multiple UV radiation sources that can move along x-, y-, and z-axes. In an embodiment, the UV radiation source is one or more UV lamps in a movable lamp fixture. In an embodiment, the device includes a rotating drum. In an embodiment, the device includes a rotating platform. In an embodiment, the device includes an orbiting platform.

The effectiveness of the irradiation process may be affected by the temperature of the implant and/or UV radiation source. In an embodiment of the present invention, the containment chamber includes a temperature control system for regulating the temperature of the implant during irradiation by heating or cooling the implant. In an embodiment of the present invention, the containment chamber includes a temperature control system for heating or cooling the radiation source. In an embodiment, the interior of the UV containment chamber is ventilated and/or cooled using one or more input and output ports to control heating of the implant during the UV irradiation process. In an embodiment, such ventilation and/or cooling is controlled by a controller that is operated manually or automatically in response to temperature measurements made at the implant or elsewhere in the interior of the containment chamber.

In an embodiment of the present invention, the UV radiation source includes one or more of a fluorescent lamp, a gas discharge lamp, a high-intensity discharge lamp, an electroluminescent lamp, a light-emitting diode, a laser, an incandescent lamp, an electron-stimulated lamp, and other devices that emit UV radiation at intensities suitable for cross-linking DCBF.

In an embodiment, a UV radiation controller is integrated in the containment chamber. The UV radiation controller includes one or more of means for opening and/or closing a shutter, means for turning one or more UV radiation sources on and/or off, means for controlling the brightness of the UV radiation source, and other means for controlling the intensity and/or duration of the irradiation of the implant. In an embodiment, a controller is provided, the controller having circuitry for controlling one or more of the aforesaid means. In an embodiment, the controller includes a computer. In an embodiment, the computer is programmable by an operator.

In an embodiment, the containment chamber includes one or more sensors to sense the intensity of UV radiation emitted by the UV radiation sources and/or the intensity of UV radiation at the surface of the implant. In an embodiment, a controller is provided, the controller having circuitry for controlling the intensity of the UV radiation source. In an embodiment, the controller controls the intensity of the UV radiation source in response to output from the one or more sensors. In an embodiment, the controller includes a computer. In an embodiment, the computer is programmable by an operator such that the UV radiation source provides UV radiation of a specified intensity and/or range or wavelengths. In an embodiment, the computer is programmable by an operator such that the UV radiation source provides a total irradiation energy to the implant.

In an embodiment, the UV containment chamber is designed to be used in one or both of a sterile and a non-sterile environment. In an embodiment where the environment is non-sterile, the implant is contained in a sterile interior of a separate UV-transmissive chamber that is placed in the UV containment chamber such that radiation from the UV radiation source is transmitted through the UV-transmissive chamber to the implant. In an embodiment, the interior of a UV containment chamber is maintained as a sterile environment by sealing the UV radiation source and controller circuitry in a separate compartment. In such an embodiment, the sealed compartment is UV transmissive such that UV radiation from the UV radiation source is transmitted from the sealed compartment into the interior of the UV containment chamber.

UV cross-linking of DCBF provides an implant with properties that an otherwise non-cross-linked implant would not possess. The current lyophilized formulations of demineralized cortical fibers have a few shortcomings that can be address by UV cross-linking. One such shortcoming is the initial resistance to rehydration of a lyophilized DCBF implant. When the implant has been lyophilized, the residual moisture level is typically no more than 6% w/w and this lack of moisture causes the implant to exhibit hydrophobic characteristics. When a liquid such as water, saline, or blood is applied to the surface of the implant, the liquid sits on the surface and is not immediately absorbed. Once the initial amount of liquid becomes absorbed into the implant, the rehydrated surface exhibits hydrophilic characteristics and any additional liquid added is immediately absorbed into the implant. Another shortcoming is the lack of mechanical strength and structural rigidity of a lyophilized DCBF implant after rehydration. In the lyophilized state, the implant holds its shape and is rather stiff, however, after the implant has been rehydrated, the implant becomes soft, the DCBF start to swell, and the implant cannot be handled without permanently losing its shape. In certain situations, it is preferable for the implant to retain its shape while also being compliant and flexible even after being saturated with liquid.

UV cross-linking allows the hydrophilicity and mechanical properties of a DCBF implant to be modified quickly and efficiently compared to other methods known in the art. However, an embodiment of the present invention include physical cross-linking by techniques such as those including dehydrothermal treatment (DHT). An embodiment of the present invention includes chemical cross-linking of DCBF by one or more known methods, or by a chemical cross-linking method yet to be discovered.

Known chemical cross-linking techniques include, but are not limited to, the use of glutaraldehyde, carbodiimide (e.g., 1-ethyl-3-(3-dimethylaminopropyl) carbodiimide, also known as EDC), EDC with NHS (i.e., N-hydroxysuccinamide), genipin, catechin, succinic acid, and tannic acid. While some chemical cross-linkers have been used in the past on various types of materials, including allograft tissue, chemical cross-linking can be a complicated and lengthy process, and is potentially hazardous to the patient if the residual chemicals are not completely removed. Natural chemical cross-linkers, such as genipin and catechin, are less cytotoxic than synthetic cross-linkers, but may also have disadvantages in some applications. In the case of genepin, the tissue is stained a dark blue as a result of the cross-linking process, and the stain is difficult to remove. Chemical cross-linking is also difficult to control and is more easily applied to the entire bulk of the implant rather than to specific areas or surfaces. Too much cross-linking of the implant may also impart properties that are unfavorable. One of the advantages of implants made from DCBF is that they are moldable and cohesive after rehydration. This property is diminished as the DCBF become more cross-linked, resulting in an implant that cannot be molded into a different shape or put together once it has been taken apart. Despite the aforesaid difficulties posed by chemical cross-linking techniques, their use in forming cross-linked implants, as well as the implants themselves, are useful embodiments of the present invention.

In contrast to the chemical cross-linking methods discussed above, cross-linking by UV radiation is easily controlled and can be implemented to prepare DCBF implants that have the advantages of both non-cross-linked and cross-linked DCBF, while eliminating the disadvantages of excessive stiffness and resistance to recombination of pieces of the implant. By using UV radiation to cross-link certain surfaces of the implant while leaving other areas uncross-linked, an implant is prepared that retains its shape after rehydration due to the increased stiffness of the cross-linked regions, while also retaining the moldable and cohesive properties of the uncross-linked regions. UV cross-linking also reduces the initial hydrophobicity encountered by the lyophilized demineralized cortical fibers allowing the implant to be rehydrated nearly instantaneously. Furthermore, UV cross-linking imparts some shape memory retention to the rehydrated implant. When an external force is applied, the cross-linked implant is temporarily deformed and some liquid is displaced. However, as soon as the force is removed, the cross-linked implant will return to its original shape and resorb the previously displaced liquid. Only when a sufficient amount of force is applied does the implant permanently deform and become moldable. Additionally, the increased rigidity of the cross-linked surfaces of the implant prevents the implant from breaking apart when an excess of liquid is applied, when the implant is irrigated, or when the implant is completely submerged in a liquid.

Embodiments of the cross-linking methods of the present invention can be used to produce hydrophilic and mechanically stable DCBF implants from fully demineralized, demineralized, or partially demineralized DCBF, but is most effective for cross-linking DCBF with calcium contents of less than 1% w/w. The UV cross-linking method of the present invention may be used with DCBF having thicknesses in a range of about 80 μm to about 150 μm, or at other thicknesses where the DCBF form a cohesive mass in the absence of cross-linkages. Further, embodiments of the energetic method of the present invention can be used to prepare DCBF implants in the presence of additives. Additives such as particles of non-demineralized cortical, cancellous, or corticocancellous bone, demineralized cortical, cancellous, or corticocancellous bone may be used as long as the implant contains sufficient DCBF to form a cohesive mass. Additives such as therapeutic factors, cytokines, growth factors, pharmaceuticals, antibiotics, free-radical scavengers, sugars, or other chemical or bioactive compounds will retain their effectiveness after exposure, since the energetic exposure, and thus cross-linking, occurs at and/or near the surfaces of the implant, and does not significantly affect the interior of the implant.

Although the exemplary embodiments of the energetic cross-linking process described herein discuss the use of UV radiation, one having ordinary skill in the art and possession of the present disclosure will recognize that other sources of energy may be used to cross-link protein-rich fibers. Besides UV radiation, suitable energetic sources include, but are not limited to, ozone, plasma, (e.g., RF plasma), coronal discharge, or other means that provide the energy needed to form cross-links between proteins. Suitable plasma media include, but are not limited to, air plasma, oxygen plasma, and ammonium plasma.

IV. Treatment of Tissue Types Other Than Demineralized Bone

Without being bound by theory, it is believed that the increased wettability and other effects observed in DCBF and masses of DCBF that have been treated as discussed herein result from interactions with the collagen and/or glycoproteins present in cortical demineralized bone matrix. Thus, one having ordinary skill in the art and possession of the present disclosure would reasonably expect that similar beneficial results may be obtained by applying such treatments to demineralized bone matrix from cancellous or corticocancellous bone. One having ordinary skill in the art and possession of the present disclosure would also reasonably expect that similar beneficial results may be obtained by applying such treatments to fibers or other particles of tissue types other than demineralized bone matrix. Such other tissue types may be derived from any suitable organ or other tissue source, whether autologous, allogeneic, or xenogeneic. Examples of suitable xenogeneic sources of tissues include, but are not necessarily limited to, warm-blooded vertebrates, including mammals, such mammalian sources including human, bovine, ovine, caprine, and porcine sources. Suitable tissue types may include, but are not necessarily limited to an adipose tissue, an amnion tissue, an artery tissue, a bone tissue, a cartilage tissue, a chorion tissue, a colon tissue, a dental tissue, a dermal tissue, a duodenal tissue, an endothelial tissue, an epithelial tissue, a fascial tissue, a gastrointestinal tissue, a growth plate tissue, an intervertebral disc tissue, an intestinal mucosal tissue, an intestinal serosal tissue, a ligament tissue, a liver tissue, a lung tissue, a mammary tissue, a meniscal tissue, a muscle tissue, a nerve tissue, an ovarian tissue, a parenchymal organ tissue, a pericardial tissue, a periosteal tissue, a peritoneal tissue, a placental tissue, a skin tissue, a spleen tissue, a stomach tissue, a synovial tissue, a tendon tissue, a testes tissue, an umbilical cord tissue, a urological tissue, a vascular tissue, a vein tissue, and a combination thereof. Other suitable tissue types may include, but are not necessarily limited to, submucosa, renal capsule membrane, dermal collagen, dura mater, serosa, or basement membrane layers, including liver basement membrane. Suitable submucosa materials for these purposes include, for instance, intestinal submucosa, including small intestinal submucosa, stomach submucosa, urinary bladder submucosa, and uterine submucosa. Source tissue (i.e., tissue incorporated into a final processed product, such as an implant) of the types disclosed above may be separated from other tissue types adjacent or connected to the source tissue, or the adjacent or connected tissue may remain with the source tissue and become incorporated in the implant. One or more source tissues may be included in the final processed product.

V. Examples

The following examples are set forth so as to provide those of ordinary skill in the art with an exemplary disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g., amounts, temperatures, etc.) but some experimental errors and deviations should be accounted for.

Example 1: Fabrication of Demineralized Cortical Bone Fibers

Human long bone is recovered aseptically from a deceased donor and stored at 4° C. until ready for processing. The bone is debrided to remove soft tissue elements and the shaft of the bone is cut into cross-sections. The cortical bone is then cleaned using detergents/surfactants to remove residual blood and lipids from the bone surface.

To create DCBF, the bone sections are first shaved across the shaft of the bone using a controlled advancement rate of a lathe bit having a width approximately equal to the desired length of the bone fibers. The shaft segment is secured in a vice with a sufficient portion of the shaft protruding such that the protruding portion may be shaved. On a milling machine, a straight flute end-mill is set up such that its axis is parallel with the axis of the shaft. Utilizing the required length of the of the broad edge of the lathe bit, fibers are shaved off of the shaft by running the end-mill back and forth along the shaft until substantially all of the bone has been shaved from the shaft. The resulting bone fibers are collected for demineralization.

The bone fibers are demineralized by agitating them in 0.6 N HCl for a sufficient period of time to remove the endogenous calcium minerals to a desired residual calcium content, after which the fibers are successively rinsed with water, soaked in water, soaked in a sodium phosphate dibasic buffer to achieve a physiological pH, rinsed in water, and soaked in water. The soaked fibers may then be dried, lyophilized, or left in a wet state for further processing.

Example 2: Treatment of DCBF with PBS

DCBF are prepared as described in Example 1. After completion of the second water soak, the DCBF are decanted into a vessel, and PBS is added at a ratio in a range of about 1:3 DCBF/PBS (g/ml) to about 1:15 DCBF/PBS (g/ml). After 5 to 15 minutes of a static soak, the DCBF are decanted from the PBS, and air-dried. Additional PBS is added to the DCBF at a ratio in a range of about 1:1 DCBF/PBS (g/ml) to about 1:5 DCBF/PBS (g/ml) in a plastic jar, and the wet DCBF are lyophilized.

Example 3: Preparation of Low-Density Pre-Formed Fiber Shapes Using DCBF and Saline Low-density pre-formed fiber shapes are lyophilized DCBF which are suspended in liquid prior to lyophilization to provide a fluffy texture and a high void volume. They are hydrated by a surgeon in the operating room to form a putty-like substance for use as a bone void filler.

Low-density pre-formed fiber shapes were prepared using water or different ratios of 0.9% sodium chloride in water ("saline", in particular 0.25× saline, 0.5× saline, 0.75× saline, and 1× saline) to examine the effect of salt concentration on hydration time and handling properties of the implants. The samples prepared with water were used as control samples; the samples prepared with saline solutions were examined as test samples.

Samples of air-dried DCBF prepared according to Example 1 were soaked in water or saline at selected concentrations at a ratio in a range of about 1:3 DCBF/liquid (g/ml) to about 1:15 DCBF/liquid (g/ml) for 5 to 15 minutes, after which they were air-dried on a vacuum sieve. The samples were then lyophilized. Some samples were lyophilized in open jars; others were lyophilized with a vented lid, the ventilation holes having been covered by a porous liner having a pore size of greater than 10 µm. The lyophilized samples were then tested for hydration time and handling properties.

Test samples prepared with PBS and lyophilized with a lid and porous liner hydrated more rapidly than the control samples prepared with water. There was no significant difference in the handling of any of the test samples in comparison to the control samples.

Example 4: Preparation of Low-Density Pre-Formed Fiber Shapes Using DCBF and PBS Samples of air-dried DCBF prepared according to Example 1 were soaked in PBS at a ratio in a range of about 1:1 DCBF/PBS (g/ml) to about 1:5 DCBF/PBS (g/ml) for 5 to 15 minutes. Sets of samples were prepared using PBS at concentrations of 0.5×, and 0.25× of a standard PBS, using water as the diluent. After the soak, the samples were air-dried on a vacuum sieve, then lyophilized in open jars. The samples were then hydrated with just enough saline to provide good handling properties, and tested for appearance and hydration.

Drops of saline deposited onto the top surface of a low-density pre-formed fiber shape prepared with 0.25×PBS were absorbed in less than one minute. Drops of saline deposited onto the top surface of a low-density pre-formed fiber shape prepared with 0.5×PBS were absorbed more quickly.

Example 5: Preparation of Low-Density Pre-Formed Fiber Shapes Using Various Ratios of DCBF and PBS Samples of wet DCBF were prepared according to Example 1 without the final drying step. Samples of various sizes were soaked in a standard PBS at a ratio in a range of about 1:2 DCBF/PBS (g/ml) to about 1:5 DCBF/PBS (g/ml) for 5 to 15 minutes. After the soak, the samples were air-dried on a vacuum sieve, deposited in open jars, frozen, then lyophilized. The lyophilized samples were then tested for appearance and hydration. All of the samples had a fluffy appearance.

Low-density pre-formed fiber shapes prepared as described above were hydrated with sheep's blood, and the rates of absorption were compared with those of fiber shapes that had been prepared at a lower DCBF/PBS ratio in a range of about 1:2 (g/ml) and 1:5 (g/ml). Fiber shapes prepared at the higher ratio absorbed the sheep's blood at much faster rates than had been observed for the fiber shapes prepared at the lower ratio. The absorption rate was fastest for fiber shapes prepared at the highest ratio.

Example 6: Comparison of Fiber Shapes Lyophilized with Water and Fiber Shapes Lyophilized with PBS Samples of wet DCBF were prepared according to Example 1 without the final drying step. Two portions of wet DCBF were subjected to a static soak in standard PBS at a ratio in a range of about 1:3 DCBF/PBS (g/ml) to about 1:15 DCBF/PBS (g/ml), and air-dried. PBS diluted to 0.5× was added to a first portion at a ratio in a range of about 1:1 DCBF/PBS (g/ml) to about 1:5 DCBF/PBS (g/ml), and the DCBF was lyophilized in a plastic jar. Water was added to the second portion at a ratio in a range of about 1:1 DCBF/PBS (g/ml) to about 1:5 DCBF/PBS (g/ml), and the DCBF was lyophilized in a plastic jar.

Equal amounts of sheep's blood were dropped onto the lyophilized first (PBS) and second (water) portions of DCBF. The blood was entirely absorbed by the first portion within less than one minute, at which time only about one-third (⅓) of the blood was absorbed by the second portion.

Example 7: Preparation of a DCBF Implant Containing Mineralized Granules of Cortical or Cancellous Bone Samples of wet DCBF are prepared according to Example 1 without the final drying step. Mineralized granules or chips of cortical or cancellous bone having sizes in a range of about 200 µm to about 5 mm are prepared by milling or cutting of bone tissue which has been cleaned of any soft tissue adhering to the bone and treated with detergents/surfactants to remove blood and lipids. Following separate air-drying steps on individual vacuum sieves, mineralized cortical or cancellous granules/chips and DCBF are mixed in standard PBS at a ratio in a range of about 1:3 DCBF/PBS (g/ml) to about 1:15 DCBF/PBS (g/ml). The ratio of cortical or cancellous granules/chips to DCBF is in a range of about 1:0.1 to about 0.1:1 (g/g, based on air-dried weight), depending on the properties desired for the implant.

After mixing to obtain an approximately homogenous mixture, the resulting tissue mixture is air-dried on a vacuum sieve and deposited in jars which are subsequently filled with a volume of 0.5×PBS to re-suspend the tissue in liquid. The jars are sealed using lids with openings covered by porous liners, then frozen and lyophilized. Alternatively, after mixing and air-drying, the semi-wet tissue is placed into molds and lyophilized.

The lyophilized tissue is readily rehydrated with blood or saline and yields a moldable mass of bone tissue in which the cortical fibers provide cohesiveness and depending on their density within the tissue mass, the cortical/cancellous granules provide the implant with properties of radiopacity and/or resistance to compression.

Example 8: Preparation of a DCBF Implant Having a Stiff Shell

Wet DCBF prepared as in Example 1 was placed into a rectangular mold and shaped into an implant having dimensions of approximately 10 cm×2.5 cm×7 mm. The fiber implant was removed from the mold and placed in a UV containment chamber where it was exposed to 315-400 nm UVA radiation for a period of about 30 minutes at an intensity in a range of about 4,000 µwatts/cm$^2$ to 20,000 µwatts/cm$^2$. The orientation of the implant was changed within the UV chamber during the irradiation process to expose all surfaces of the implant evenly to UV radiation, creating a stiff shell on all surfaces of the implant. The implant was then lyophilized for storage, and rehydrated prior to implantation.

Example 9: Preparation of a DCBF Implant Having Compartments

Wet DCBF prepared as in Example 1 is placed into a rectangular mold having silicone inserts to form two large compartments on one surface of the implant. The resulting implant has dimensions of approximately 10 cm×2.5 cm×1.2 mm. The implant is removed from the mold with the silicone inserts in place. The implant is placed in a UV containment chamber where the exposed surfaces are exposed to both 100-280 nm UVC radiation and 315-400 nm UVA radiation. The longer UVA wavelength penetrates deeper into the surfaces of the implant, which imparts additional stiffness allowing the implant to retain its shape when rehydrated and loaded with additional materials in the compartments whereas the shorter UVC wavelength sterilizes the surfaces of the implant. The silicone inserts block the UVC and UVA radiation from reaching the interior of the cavities so that cross-linking does not occur at those surfaces. The resulting "boat" configuration implant has two open compartments that allow the user to add other materials such as bone marrow aspirate and cancellous chips, or other additives such as those discussed in Section III of the present disclosure. The interior surfaces of the compartments are not cross-linked, so that a user can mix the additives (e.g., the bone marrow aspirate and cancellous chips) into the non-cross-linked DCBF. After mixing, the user can pick up the implant in a single piece and fold it so as to close the compartments such that the additives are enclosed within the implant.

Example 10: Preparation of a Thin DCBF Implant Having a Cross-Linked Interior Wet DCBF prepared according to Example 1 are placed in a shallow rectangular mold to produce a thin strip-like implant with dimensions of approximately 10 cm×2.5 cm×2 mm. The implant is removed from the mold, and placed in a UV containment chamber where the exposed surfaces are exposed to 315-400 nm UVA radiation. The implant is thin enough that penetration of the UV radiation cross-links the majority of the DCBF in the interior of the implant. The resulting cross-linked implant is a porous and flexible strip that is also strong enough to be placed in areas of the body that are subject to mechanical loads that would disrupt implants having only a cross-linked shell.

Example 11: Preparation of a Low-Density DCBF Implant

Wet DCBF prepared according to Example 1 are placed in a square mold to produce cube-shaped implants having dimensions ranging from about 5 mm to about 20 mm. Excess water is added to the mold to produce implants that are highly porous. The implants are then lyophilized and rehydrated carefully as to not disturb the porous structure. The implants are then placed into a UV containment chamber where the exterior surfaces are exposed to 315-400 nm UVA radiation. The implant is then lyophilized again. The resulting low density implant is highly porous yet is able to absorb liquids without swelling or deforming permanently.

Example 12: Comparison of a Cross-Linked Implant with Non-Crosslinked Implant Lyophilized DCBF prepared as in Example 1 was rehydrated and separated into portions. Each portion was placed into a customized cylindrical mold to produce puck-shaped implants. A first group of implants were irradiated with UVA radiation at an intensity in a range of about 4,000 µwatts/cm$^2$ to 20,000 µwatts/cm$^2$. The top and bottom of the first implant were irradiated for 15 minutes each, for a total exposure time of 30 minutes, for a total energy exposure in a range of about 180 Joules to about 900 Joules. The second group of implants were not irradiated, and served as comparison samples. The implants were then lyophilized. The implants had final dimensions of about 13 mm height and 29 mm diameter.

The implants were compared as follows:
1. Implants from the irradiated and non-irradiated groups were immersed in water or in saline solution. The implants from both groups remained intact. The implants from the irradiated group did not swell by any significant amount, but the implants from the non-irradiated group swelled by a considerable amount.
2. Implants from the irradiated and non-irradiated groups were compressed to a fraction of their initial size. Implants from the irradiated group showed better shape memory retention than implants from the non-irradiated group.
3. Rehydration of the lyophilized implants from both groups showed that the irradiated implants absorbed liquids more rapidly than the non-irradiated implants, and retained their shape better after rehydration even after being compressed significantly.
4. A moldability test showed that the irradiated implants became permanently deformed when sufficient pressure was applied to break the outer shell formed by cross-linking. The irradiated implants could then be molded into a variety of shapes.

Example 13: Preparation of an Implant from Cartilage Fibers

Lyophilized fibers of articular cartilage, obtained by grating larger cartilage pieces, are rehydrated and placed in a cylindrical mold to produce plug-shaped implants having diameters in a range of about 5 mm to about 40 mm and lengths in a range of about 5 mm-to about 20 mm. The implants are removed from the molds, and placed in a UV containment chamber where the surfaces of the plugs are exposed to 315-400 nm UVA. The implant is then lyophilized and rehydrated. The resulting implant is compressible, but retains its shape when subjected to cyclical loading. The implant also stays in one piece and does not disperse when subjected to a load, during irrigation, or when placed in an aqueous environment.

Example 14: Preparation of an Implant from Soft Tissue

Lyophilized tissues (e.g., fibers, flakes or powder) derived from placental (amnion, chorion, umbilical cord) or dermal tissue were rehydrated and compressed into thin sheets. The sheets were then trimmed or otherwise formed into a variety of shapes of varying sizes. The sheets were placed in a UV containment chamber where the surfaces of the sheets were exposed to 315-400 nm UVA radiation for about 20 minutes at a radiation intensity of about 20,000 μwatts/cm$^2$. The implant was then lyophilized and rehydrated prior to implantation. The resulting implant was a very thin sheet that retained its shape when flexed, perforated, irrigated, and placed in an aqueous environment.

Example 15: Preparation of a DCBF Implant by Chemical Cross-Linking

Wet DCBF prepared as in Example 1 are placed into a rectangular mold and shaped into an implant having dimensions of approximately 10 cm×2.5 cm×7 mm. The fiber implant is removed from the mold and placed in a sealed vapor chamber. A solution of glutaraldehyde is heated within the chamber to generate glutaraldehyde vapors which penetrate and cross-link DCBF throughout the entire implant. The implant is exposed to the vapors for a set amount of time in a range of about 5 minutes to about 24 hours). After cross-linking, the residual unreacted glutaraldehyde and any unbound cross-linking byproducts are rinsed out of the implant using water, solutions of neutralization salts, and/or buffer solutions. The implant is then lyophilized for storage, and rehydrated prior to implantation.

Example 16: Preparation of a DCBF Implant by Natural Cross-Linking

Wet DCBF prepared as in Example 1 are placed into a rectangular mold and shaped into an implant having dimensions of approximately 10 cm×2.5 cm×7 mm. A mesh is placed over the open surface of the mold to allow liquids access to the tissue while preventing the tissue from escaping the mold. The mold is submerged in a solution of genipin for a set amount of time in a range of about 5 minutes to about 24 hours. The genipin solution may remain static or can be stirred to increase the rate of cross-linking throughout the implant. After cross-linking, the residual genipin is rinsed out of the implant using water. Other rinses including detergents, salts, and/or buffers may be used to reduce residual staining of the tissue that occurs during the genipin cross-linking process. The implant is then lyophilized for storage, and rehydrated prior to implantation.

Example 17: Preparation of a Hydrated DCBF Implant

Three grams of lyophilized DCBF was weighed out in a jar and between about 5 to about 7.5 ml of PBS was added to the DCBF. The two components were mixed, capped and let stand for more than 15 minutes at room temperature to ensure full homogenous hydration. The equilibrated mixture was packed into a plastic syringe, which was then capped and sealed in a foil pouch to prevent moisture loss during long-term storage. The mixture was extruded from the syringe into a pan and examined. The mixture was observed to have a slight off-white color, and to have a smooth consistency that held together when manually manipulated.

Example 18: Preparation of a Shaped DCBF Implant with Enhanced Cohesiveness

Wet DCBF prepared as in Example 1 are rolled into a mass and kneaded to loosen any clumps of fibers and create more fiber entanglement throughout the mass. Once thoroughly kneaded, the whole mass is placed into the mold and the tissue is redistributed into the mold space by pressing with fingers or a spatula. The tissue is lyophilized in the mold, creating a shaped implant.

Molding DCBF in this manner results in an implant with enhanced cohesiveness when rehydrated, compared to an implant where tissue is placed into the mold in small chunks.

Figure 3A:
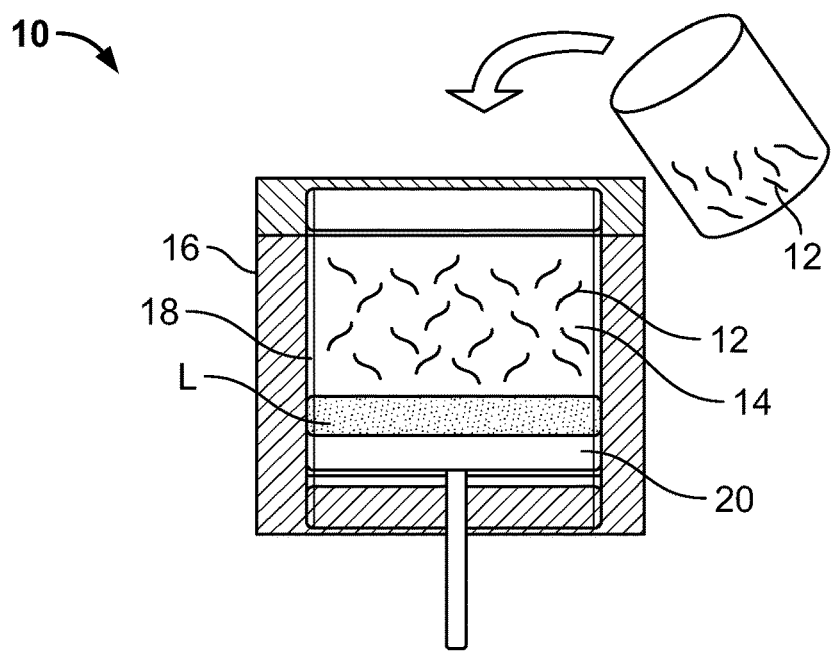
FIGS. 3A-3C are schematic partial cross-sectional views of a rectangular syringe mold as used in one exemplary embodiment of a process for making implants from demineralized cortical bone fiber.

Example 19: Preparation of a Shaped DCBF Implant with Enhanced Cohesiveness Using Syringe Mold Use of a syringe mold to shape the DCBF is shown schematically in FIGS. 3A-3C and will now be described. As shown in FIG. 3A, wet DCBF (comprising DCBF fibers 12) prepared as in Example 1 are placed into a custom rectangular syringe mold 10, with an excess amount of liquid L (e.g., saline) so that the DCBF fibers 12 are homogenously suspended in solution 14. More particularly, the custom syringe mold 10 includes a housing 16, the walls of which form a chamber 18, within which is a reciprocatingly movable plunger 20 that defines the bottom of the chamber 18. The wet DCBF and liquid are placed into the chamber 18 of the mold 10. When the plunger 20 is in its undepressed position (see FIG. 3A), the inner dimensions of the chamber 18 may be, for example without limitation, approximately 10 cm(L)×2.5 cm(W)×127 mm(H). In some embodiments, the cross-section of the chamber 18 is in the shape of a rectangle with rounded edges. In such embodiments, the plunger 20 has dimensions of approximately 10 cm(L)×2.5 cm(W)×20 mm(H) and is also in the shape of a rectangle with rounded edges to match the cross-sectional opening of the chamber 18. An o-ring (not shown per se) seals the interface between the plunger 20 and the chamber 18.

Figure 3B:
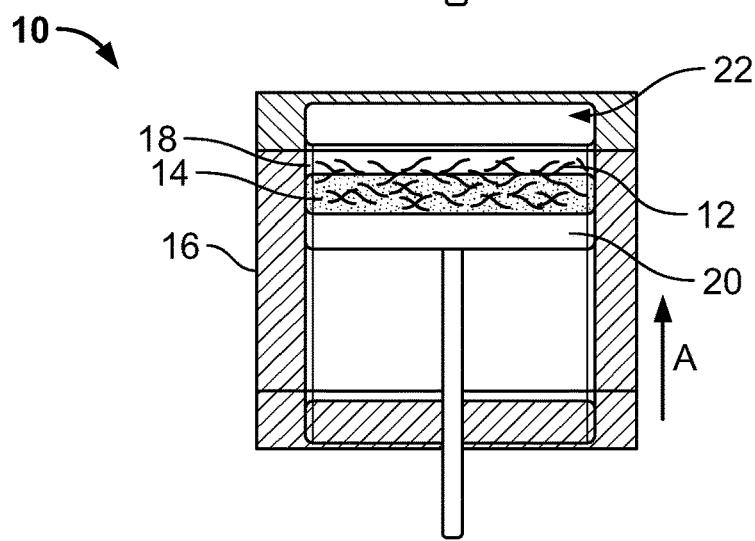
Figure 3C:
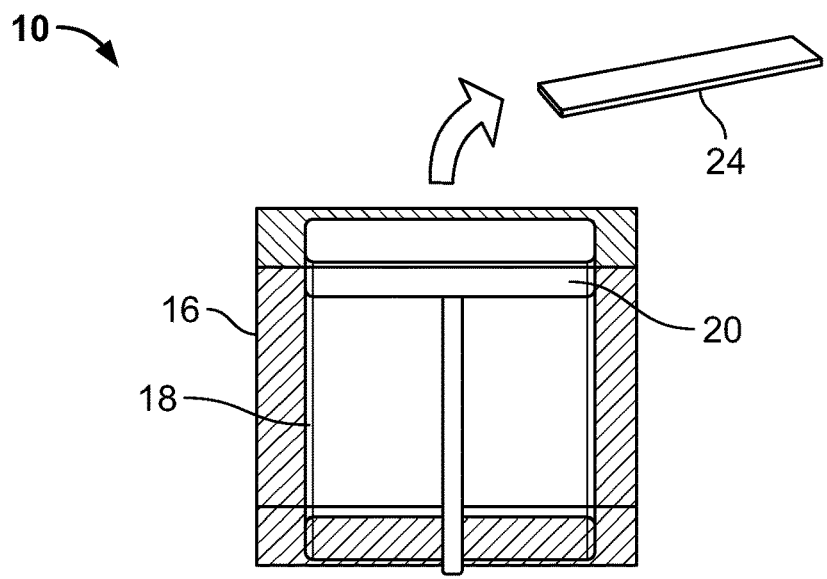
Figure 4:
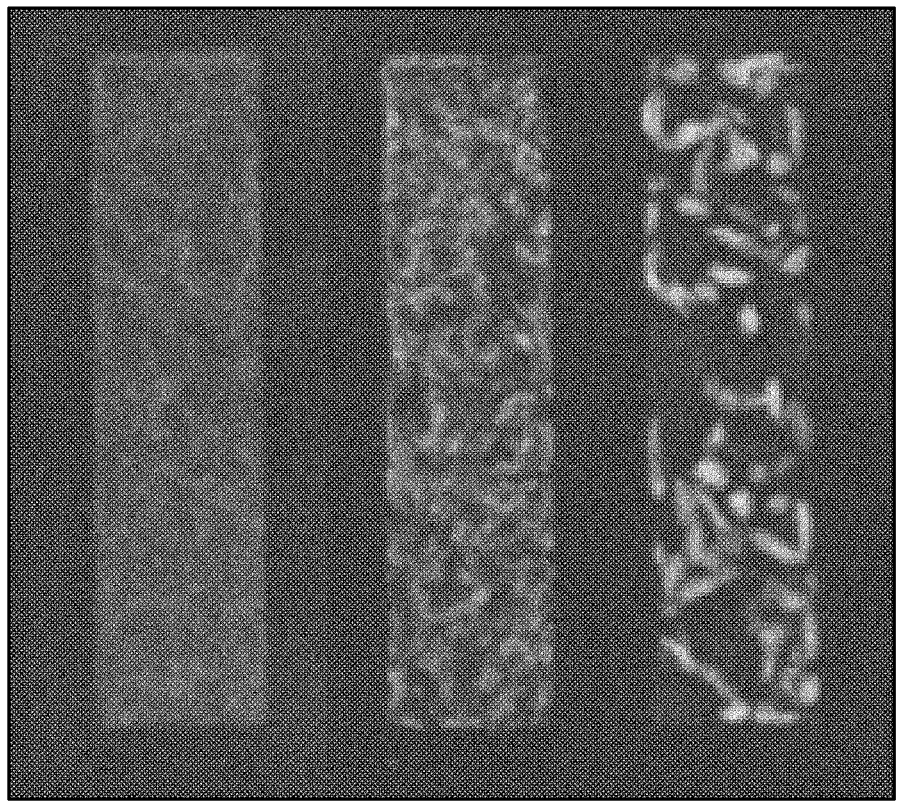
FIG. 4 is an image showing demineralized cortical bone fiber implants with varying degrees of radio-opacity imparted by the addition of mineralized cortical bone

As shown in FIG. 3B, a detachable filter 22, which is liquid permeable, fits across the top of the housing 16 to enclose the top of the chamber 18. After the DCBF fibers 12 and liquid L are placed into the chamber 18, the detachable filter 22 is placed over the open surface of the chamber such that when the plunger 20 is depressed (in the direction of arrow A), excess liquid is able to escape from the chamber 18 through the filter 22, while the DCBF fibers 12 are retained within. With reference to FIG. 3C, the filter 22 may then be detached and the implant 24 comprising the DCBF fibers (not shown in the densely packed implant of FIG. 3C) is pushed out of the chamber. The implant 24 is then lyophilized for storage and rehydrated prior to implantation. The density of the implant 24 may be altered by changing the distance that the plunger 20 is pushed toward the filter 22. Implants molded in this manner have enhanced cohesiveness and better shape retention due to the more homogenous distribution and enhanced entanglement of DCBF fibers in the implants.

Example 20: Preparation of a Radio-Opaque Shaped DCBF Implant with Mineralized Bone Wet DCBF prepared as in Example 1 is combined with mineralized cortical or cancellous granules/powder, placed into a rectangular mold, and shaped into an implant having dimensions of approximately 10 cm(L)×2.5 cm(W)×7 mm(H). The implant is removed from the mold and placed in a UV containment chamber where it is exposed to 315-400 nm UVA radiation for a period of about 30 minutes at an intensity in a range of from about 4,000 μwatts/cm$^2$ to about 20,000 μwatts/cm$^2$ before being removed and lyophilized. The inclusion of mineralized cortical or cancellous in the implant imparts additional radio-opacity due to the added mineral content. This allows for improved visualization of the graft by certain imaging methodologies (e.g. x-ray) during or after implantation of the graft material.

Example 21: Preparation of a Radio-Opaque Shaped DCBF Implant with Selective Remineralization Wet DCBF prepared as in Example 1 are placed into a custom cylindrical syringe mold yielding an implant with final dimensions of approximately 13 mm in height and 29 mm in diameter. The implant is removed from the mold and placed in a UV containment chamber where it was exposed to 315-400 nm UVA radiation for a period of about 30 minutes at an intensity in a range of from about 4,000 μwatts/cm$^2$ to about 20,000 μwatts/cm$^2$. The UV irradiation cross-links the outer surface of the implant allowing the implant to retain its shape when submerged in a liquid solution.

To remineralize the implant, two solutions are prepared as follows. The first solution is composed of 0.55M calcium chloride in DI water and the second solution is composed of 0.5M sodium phosphate in DI water. The irradiated implant is fully submerged in an aliquot of the first solution for 30 minutes under gentle agitation. After 30 minutes, the first solution is removed and the implant is submerged in an aliquot of the second solution for 30 minutes under gentle agitation. This process of alternating solutions is repeated until a hard mineralized shell develops on the surface of the implant that imparts radio-opacity that is comparable to normal mineralized human bone and increased mechanical strength of the implant through the remineralization of DCBF. The bulk/interior of the implant may also be mineralized in a similar fashion of alternating soaks of calcium chloride and sodium phosphate by the use of increased agitation and forcing the solutions through the bulk of the implant using positive or negative pressure. The implant is then lyophilized for storage and rehydrated prior to implantation.

Example 22: Preparation of a Shaped DCBF Implant with Enhanced Cohesiveness and Biological Properties Wet DCBF prepared as in Example 1 are combined with minced, powdered, or fibrous periosteum, placed into a rectangular mold, and shaped into an implant having dimensions of approximately 10 cm(L)×2.5 cm(W)×7 mm(H). The implant is removed from the mold and placed in a UV containment chamber where it was exposed to 315-400 nm UVA radiation for a period of about 30 minutes at an intensity in a range of from about 4,000 μwatts/cm$^2$ to about 20,000 μwatts/cm$^2$ before being removed and lyophilized. The inclusion of periosteum in the implant imparts enhanced cohesiveness and irrigation resistance due to the putty-like nature of periosteum and enhanced biological properties due to the addition of growth factors endogenous to the periosteum membrane.

Example 23: Preparation of a Shaped DCBF Implant with Enhanced Cohesiveness by Heating Wet DCBF prepared and molded into a shaped implant as in Examples 18 and 19 are placed in a heated chamber (e.g., lyophilizer, incubator, gravity oven), with or without UV exposure, at temperatures of from about 24° C. to about 70° C., and allowed to incubate for a period of time of from about 10 minutes to about 24 hours. The heating process improves the cohesiveness of the implant and prevents the implant from dispersing when placed in a rehydrating solution (e.g., water, saline, blood). After heating, the implant is lyophilized for storage and rehydrated prior to implantation.

Figure 6A:
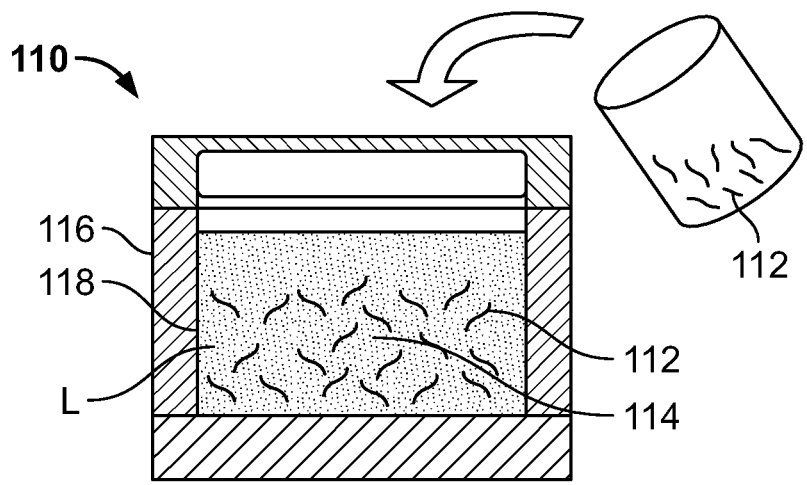
FIGS. 6A-6C are schematic partial cross-sectional views of a rectangular syringe mold having a plunger with perforation which is used in one exemplary embodiment of a process for making implants from demineralized cortical bone fiber.
Figure 6B:
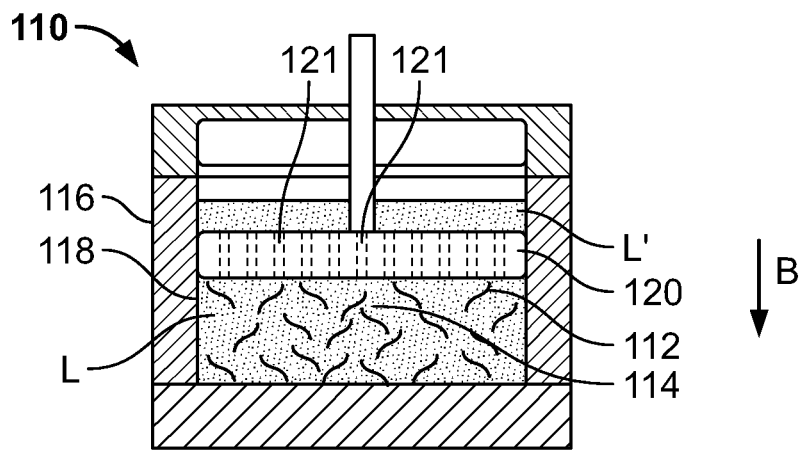

Example 24: Preparation of a Shaped DCBF Implant with Enhanced Cohesiveness Using Syringe Mold Having a Perforated Plunger A different syringe mold than that used for Example 19 was used to shape DCBF fiber and is shown schematically in FIGS. 6A-6C. As shown in FIG. 6A, wet DCBF (comprising DCBF fibers 12) prepared as in Example 1 are placed into a custom rectangular syringe mold 110, with an excess amount of liquid L (e.g., saline) so that the DCBF fibers 112 are homogenously suspended in solution 114. More particularly, the custom syringe mold 110 includes a housing 116, the walls and bottom of which form a chamber 118 and within which is a reciprocatingly movable plunger 120 which is operated from the top of the mold and fits within the open cross section of the chamber 118. The wet DCBF 112 and liquid L are placed into the chamber 118 of the mold 110. Before the plunger 120 is depressed into the chamber 118 (see FIG. 6B), the inner dimensions of the chamber 118 may be, for example without limitation, approximately 10 cm(L)×2.5 cm(W)×127 mm(H). In some embodiments, the cross-section of the chamber 118 is in the shape of a rectangle with rounded edges. In such embodiments, as shown in FIG. 6B, the plunger 120 has dimensions of approximately 10 cm(L)×2.5 cm(W)×20 mm(H) and also has a cross sectional shape of a rectangle with rounded edges to match the cross-sectional opening of the chamber 118. An o-ring (not shown per se) seals the interface between the plunger 120 and the chamber 118. (The steps of the foregoing method are shown schematically in FIG. 5.)

Figure 6C:
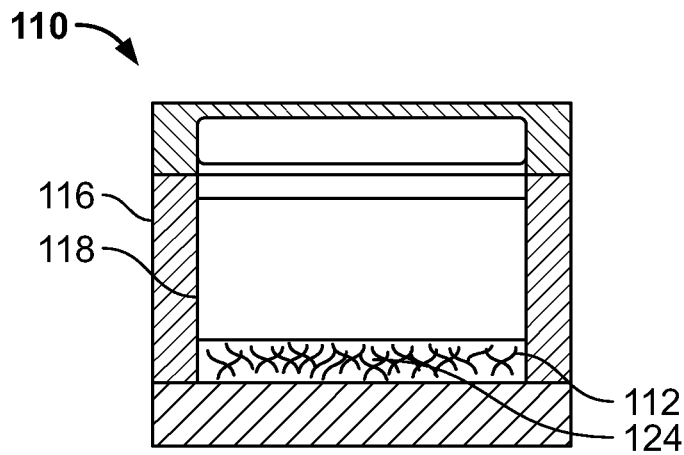

As shown in FIG. 6B, the plunger has a plurality of perforations 121 for the movement of liquid L through the plunger, such that when the plunger is depressed within the chamber 118 in the direction shown by the arrow B, the plunger fits across the top of the housing 116, enclosing the chamber 118 and compressing the DCBF fibers 112. More particularly, after the DCBF fibers 112 and liquid L are placed into the chamber 118, the plunger 120 is depressed (in the direction of arrow B), excess liquid L' is able to escape from the chamber 118 through the perforations 121, while the DCBF fibers 112 are retained and compressed within to form an implant. Each of the perforations 121 may be any suitable size and shape that will allow excess liquid to escape from the chamber 118, while retaining the DCBF fibers 112. For example, in some embodiments, without limitation, each perforation may have a circular shape with a diameter of about 1 millimeter, or about 1.5 millimeters, or even 2 millimeters. With reference to FIG. 6C, after the DCBF fibers have been compressed to the desired degree within the chamber 118, the excess liquid is poured out of the mold 110 and the plunger 120 removed. The height and density of the implant 124 may be altered by changing the distance that the plunger 120 is depressed in the chamber 118. In an embodiment, the implant 124 (still in the mold 110) is then frozen in a freezer at from about −80° C. to about 0° C. for up to 48 hours. The implant 124 (still in the mold 110) is then cured by warming using a warming plate or warm air at about 40° C. for about 8 hours. The implant 124 comprising the compressed treated DCBF fibers 112 (still in the mold 110) is lyophilized, after which the implant is easily removed from the chamber 118. After lyophilizing, the implant 124 may be stored and is rehydrated prior to implantation. Implants produced in this manner have enhanced cohesiveness and retain their shape better upon rehydration prior to use.

Example 25: Determining the Wettability of the Shaped DCBF Implant Produced Using Syringe Molds Having a Perforated Plunger Various implants produced by according to Example 24 were tested for wettability as follows and the results are provided below in Table 1. Differently shaped implants were tested where "bricks" were implants having a generally rectangular cross section, and "half pipes" were implants having a generally "C" shaped cross section.
1. Wettability Evaluation: A drop of 0.9% saline solution (roughly 0.3 cc) is added to the top or bottom surface of the implant and the length of time it takes for each droplet to absorb into the implant is recorded.
2. Rehydration Evaluation: The implant is placed into a basin containing excess 0.9% saline solution to completely submerge the implant. The length of time it takes for the implant to absorb enough liquid to sink to the bottom of the basin is recorded.
3. Wettability/rehydration times utilizing the droplet test range from a few seconds (0:07) to a few minutes (4:00) whereas complete rehydration of the implant varies from 24 seconds to 20 minutes.
4. Preferred/suitable wettability/rehydration times for DCBF implants may be tailored to the end user/application and could range anywhere from near instantaneous wettability/rehydration (1-2 seconds) to much longer rehydration times of upwards of 20-30 min (preferably within 5 min).

TABLE 1

| Implant Type | Wettability time - top surface (mm:ss) | Wettability time- bottom surface (mm:ss) | Complete rehydration - submerged (mm:ss) |
| --- | --- | --- | --- |
| Brick - A | 1:15 | 1:02 | 2:50 |
| Brick - B | 0:15 | 0:15 | 0:24 |
| Brick - C | 1:18 | 1:16 | 2:40 |
| Brick - D | 0:45 | 0:07 | 1:15 |
| Brick - E | 2:00 | 3:00 | 20:00 |
| Brick - F | 0:38 | 0:31 | 2:15 |
| Brick - G | 0:24 | 1:03 | 3:20 |
| Brick - H | 0:29 | 1:05 | 13:00 |

TABLE 1-continued

| Implant Type | Wettability time - top surface (mm:ss) | Wettability time- bottom surface (mm:ss) | Complete rehydration - submerged (mm:ss) |
| --- | --- | --- | --- |
| Half Pipe -A | 1:45 | 4:00 | 4:00 |
| Half Pipe -B | 0:45 | 1:09 | 2:50 |

Example 26: Testing Shaped DCBF Implant Produced Using Syringe Molds Having a Perforated Plunger for Uniform Density Various implants produced by according to Example 24 were tested for uniform densitys follows and the results are provided below in Table 2. Differently shaped implants were tested where a "disc" was an implant having a generally circular cross section, and "strips" were implants having a generally rectangular shaped cross section.
1. The weight of a DCBF implant was measured using an analytical balance.
2. Calipers were used to measure the dimensions of the implant, and the volume of the implant was calculated.
3. The density of the entire implant was calculated by dividing the weight recorded in step 1 by the volume calculated in step 2.
4. The implant was then cut into four equally sized pieces (quarters Q1, Q2, Q3 and Q4) using a scalpel. Steps 1-3 were repeated for each piece of the implant.
5. The relative standard deviation of the densities was calculated by dividing the standard deviation of the densities by the average. An implant can be said to have uniform density if the relative standard deviation of the measured densities is less than about 30%.

TABLE 2

| Shape | Weight (g) | Length (mm) | Width (mm) | Height (mm) | Volume (cc) | Density (g/cc) |
| --- | --- | --- | --- | --- | --- | --- |
| 5 cc disc | 1.317 | 44.81 | | 9.18 | 14.470 | 0.091 |
| Q1 | 0.349 | | | | 3.617 | 0.096 |
| Q2 | 0.319 | | | | 3.617 | 0.088 |
| Q3 | 0.308 | | | | 3.617 | 0.085 |
| Q4 | 0.292 | | | | 3.617 | 0.081 |
| | | | | | Average | 0.088 |
| | | | | | Std Dev | 0.005 |
| | | | | | % RSD | 6.028 |
| 20 cm strip | 2.823 | 192 | 9.16 | 7.25 | 12.751 | 0.221 |
| Q1 | 0.749 | 47.53 | 9.05 | 7.32 | 3.149 | 0.238 |
| Q2 | 0.582 | 47.15 | 9.17 | 6.29 | 2.720 | 0.214 |
| Q3 | 0.753 | 50.3 | 9.16 | 6.89 | 3.175 | 0.237 |
| Q4 | 0.754 | 48.94 | 9.18 | 7.05 | 3.167 | 0.238 |
| | | | | | Average | 0.230 |
| | | | | | Std Dev | 0.010 |
| | | | | | % RSD | 4.389 |
| 10 cm strip | 1.63 | 95.32 | 9.01 | 7.54 | 6.476 | 0.252 |
| Q1 | 0.386 | 24.05 | 9.03 | 7.65 | 1.661 | 0.232 |
| Q2 | 0.432 | 23.84 | 8.98 | 8.84 | 1.892 | 0.228 |
| Q3 | 0.386 | 25.06 | 8.92 | 6.77 | 1.513 | 0.255 |
| Q4 | 0.416 | 23.72 | 9.12 | 7.44 | 1.609 | 0.258 |
| | | | | | Average | 0.245 |
| | | | | | Std Dev | 0.012 |
| | | | | | % RSD | 5.055 |

While the disclosed invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the described invention.

We claim:

1. A method for producing an implant from modified demineralized cortical bone fibers, said method comprising the steps of:
    contacting the demineralized cortical bone fibers with a salt solution prior to lyophilizing; and
    shaping a mass of demineralized cortical bone fibers to form an implant having a desired shape; and
    lyophilizing the implant to produce a lyophilized implant that has a residual moisture content of less than about 6% by weight, based on the total weight of the implant, and a complete rehydration time of less than about 30 minutes, and wherein said lyophilized implant remains cohesive and retains its shape upon complete hydration.

2. The method of claim 1, wherein the implant has a wettability time of less than about 5 minutes and a complete rehydration time of less than about 30 minutes.

3. The method of claim 1, further comprising contacting the demineralized cortical bone fibers with a chemical solution, which may or may not be combined with the salt solution prior to shaping and is selected from: a biocompatible polar molecule, a buffer solution, and combinations thereof.

4. The method of claim 3, wherein the chemical solution is a buffered saline solution.

5. The method of claim 1, further comprising the step of curing the implant at a temperature of from about 20° C. to about 50° C. for a period of up to about 48 hours by one or more techniques selected from air drying, heat drying and applying energy to the implant, said curing step being performed prior to said lyophilizing step.

6. The method of claim 1, further comprising the step of crosslinking at least a portion of the implant by one or more techniques selected from: exposing the implant to energy, chemical crosslinking and heating, said crosslinking step being performed prior to said lyophilizing step.

7. The method of claim 6, wherein said crosslinking step is performed by exposing the implant to energy and the energy is selected from ultraviolet light or microwave energy.

8. The method of claim 1, wherein the step of shaping comprises:
    providing to an implant forming container a solution comprising demineralized cortical bone fibers and a liquid;
    separating the liquid from the demineralized cortical bone fibers; and
    removing the liquid from the container.

9. The method of claim 8, wherein the step of shaping further comprises agitating the solution in the implant forming container to homogenously distribute the demineralized cortical bone fibers in the liquid.

10. The method of claim 9, wherein the implant forming container is a press mold comprising a reservoir for holding the solution therein and a plunger which is reciprocatingly movable in and out of the reservoir, wherein the step of separating is performed by pressing the plunger into the reservoir, thereby compressing the demineralized cortical bone fibers and causing the liquid to separate from the demineralized cortical bone fibers by either flowing through a filter at an end of the reservoir that is opposite the plunger, or by flowing through a plurality of perforations provided in the plunger.

11. A method for producing an implant from modified demineralized cortical bone fibers, said method comprising the steps of:
    contacting the demineralized cortical bone fibers with a salt solution prior to lyophilizing;
    shaping a mass of demineralized cortical bone fibers to form an implant having a desired shape;
    curing the implant at a temperature of from about 20° C. to about 50° C. for a period of up to about 48 hours by one or more techniques selected from air drying, heat drying and applying energy to the implant, said curing step being performed prior to said lyophilizing step; and
    lyophilizing the implant to produce a lyophilized implant that has a residual moisture content of less than about 6% by weight, based on the total weight of the implant, and a complete rehydration time of less than about 30 minutes, and wherein said lyophilized implant remains cohesive and retains its shape upon complete hydration.

12. The method of claim 11, wherein the step of shaping comprises:
    providing to an implant forming container a solution comprising demineralized cortical bone fibers and a liquid;
    separating the liquid from the demineralized cortical bone fibers; and
    removing the liquid from the container.

13. The method of claim 12, wherein the implant forming container is a press mold comprising a reservoir for holding the solution therein and a plunger which is reciprocatingly movable in and out of the reservoir, wherein the step of separating is performed by pressing the plunger into the reservoir, thereby compressing the demineralized cortical bone fibers and causing the liquid to separate from the demineralized cortical bone fibers by either flowing through a filter at an end of the reservoir that is opposite the plunger, or by flowing through a plurality of perforations provided in the plunger.

14. The method of claim 11, further comprising the step of contacting the demineralized cortical bone fibers with a chemical solution, either prior to or after they are shaped to form the implant.

15. The method of claim 14, wherein the chemical solution is selected from: a biocompatible polar molecule, a salt solution, a buffer solution and combinations thereof.

16. The method of claim 11, further comprising the step of crosslinking at least a portion of the implant by one or more techniques selected from: exposing the implant to energy, chemical crosslinking and heating, said crosslinking step being performed prior to said lyophilizing step.

* * * * *